(12) United States Patent
Emerson, Jr. et al.

(10) Patent No.: US 9,260,755 B2
(45) Date of Patent: Feb. 16, 2016

(54) COMPOSITIONS AND METHODS FOR CHARACTERIZING AND TREATING MUSCULAR DYSTROPHY

(71) Applicant: University of Massachusetts, Boston, MA (US)

(72) Inventors: Charles P. Emerson, Jr., Lyndon, MA (US); Jennifer Chen, Watertown, MA (US); Oliver D. King, Cambridge, MA (US)

(73) Assignee: University of Massachusetts, Boston, MA (US)

( * ) Notice: Subject to any disclaimer, the term of this patent is extended or adjusted under 35 U.S.C. 154(b) by 169 days.

(21) Appl. No.: 13/861,227

(22) Filed: Apr. 11, 2013

(65) Prior Publication Data

US 2013/0347136 A1  Dec. 26, 2013

Related U.S. Application Data

(60) Provisional application No. 61/622,942, filed on Apr. 11, 2012.

(51) Int. Cl.

| | |
|---|---|
| *A01K 67/00* | (2006.01) |
| *C12Q 1/68* | (2006.01) |
| *C12N 15/113* | (2010.01) |
| *C12N 15/11* | (2006.01) |
| *A01K 67/027* | (2006.01) |
| *C12N 5/077* | (2010.01) |

(52) U.S. Cl.
CPC .......... *C12Q 1/6883* (2013.01); *A01K 67/0271* (2013.01); *C12N 5/0658* (2013.01); *C12N 15/111* (2013.01); *C12N 15/113* (2013.01); *C12N 2310/11* (2013.01); *C12N 2310/315* (2013.01); *C12N 2310/322* (2013.01); *C12N 2310/3233* (2013.01); *C12N 2310/341* (2013.01); *C12N 2310/346* (2013.01); *C12N 2320/12* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2013/0347136 A1*  12/2013  Emerson, Jr. ........ C12N 15/111
                                                        800/9

FOREIGN PATENT DOCUMENTS

| WO | WO 2005/037231 | 4/2005 | |
|---|---|---|---|
| WO | WO 2012/024535 | 2/2012 | ............... C12Q 1/68 |

OTHER PUBLICATIONS

International Search Report and The Written Opinion of the International Searching Authority for International Application No. PCT/US2013/036215 dated Aug. 8, 2013 (12 pages).
Cheli et al., "Expression Profiling of FSHD-1 and FSHD-2 Cells during Myogenic Differentiation Evidences Common and Distinctive Gene Dysregulation Patters," PLoS One, vol. 6, Issue 6, pp. 1-11 (Jun. 2011).
Eisenberg et al., "Distinctive patterns of microRNA expression in primary muscular disorders," PNAS, vol. 104, No. 43, pp. 17016-17021 (Oct. 23, 2007).
Sachico Homma et al., "A unique library of myogenic cells from facioscapulohumeral muscular dystrophy subjects and unaffected relatives: family, disease and cell function", *European Journal of Human Genetics*, vol. 20, pp. 404-410 (2012).
Peter S. Masny et al., "Analysis of allele-specific RNA transcription in FSHD by RNA-DNA FISH in single myonuclei", *European Journal of Human Genetics*, vol. 18, pp. 448-456 (2010).
Osborne et al., "Expression profile of FSHD supports a link between retinal vasculopathy and muscular dystrophy," *Neurology*, vol. 68, pp. 569-577 (2007).
Wallace et al., "RNA Interference Improves Myopathic Phenotypes in Mice Over-expressing FSHD Region Gene 1 (FRG1)," The American Society of Gene and Cell Therapy, vol. 19, No. 11, pp. 2048-2054 (Nov. 2011).
Sara T. Winokur et al., "Expression profiling of FSHD muscle supports a defect in specific stages of myogenic differentiation", *Human Molecular Genetics*, vol. 12, No. 22, pp. 2895-2907 (2003).
Bécamel, Philippe, Notification Concerning Transmittal of International Preliminary Report on Patentability (Chapter I of the Patent Cooperation Treaty), Int. Appl. No. PCT/US2013/036215, mailed Oct. 23, 2014, 8 pages.

\* cited by examiner

*Primary Examiner* — Michael Burkhart
(74) *Attorney, Agent, or Firm* — Fish & Richardson P.C.

(57) ABSTRACT

Compositions and methods for identifying new treatments for Facioscapulohumeral muscular dystrophy (FSHD), and uses thereof.

16 Claims, 1 Drawing Sheet

| COHORT | BICEPS | | DELTOID | |
|---|---|---|---|---|
| | FSHD | CONTROL | FSHD | CONTROL |
| 01* | 01Abic 01Bbic | 01Ubic | 01Adel 01Bdel | 01Udel |
| 3 | 03Abic | 03Ubic | 03Adel | 03Udel |
| 5 | 05Abic 05Cbic | 05Vbic | 05Adel 05Bdel 05Cdel | 05Vdel |
| 7 | 07Abic | 07Ubic | 07Adel | 07Udel |
| 9 | 09Abic | 09Ubic | 09Adel | 09Udel |
| 10 | 10Abic | In progress | 10Adel | In progress |
| 12 | 12Abic 12Bbic | 12Ubic 12Vbic | 12Adel 12Bdel | 12Ubic 12Vdel |
| 13 | 13Bbic | 13Ubic | 13Bdel | 13Udel |
| 14 | 14Abic 14Bbic | 14Vbic 14Wbic | 14Adel 14Bdel | 14Vdel 14Wdel |
| 15* | 15Abic 15Bbic | 15Vbic | 15Adel 15Bdel | 15Vdel |
| 16 | 16Abic | 16Ubic | 16Adel | 16Udel |
| 17 | 17Abic | 17Ubic 17Vbic | 17Adel | 17Udel 17Vdel |
| 18 | 18Abic | 18Ubic | 18Adel | 18Udel |
| 19 | 19Abic | 19Ubic | 19Adel | 19Udel |
| 20 | 20Abic | 20Ubic | 20Adel | 20Udel |
| 21 | 21Abic 21Bbic | 21Ubic | 21Adel 21Bdel | 21Udel |
| 22 | 22Abic | 22Ubic | 22Adel | 22Udel |
| 23 | Not available | Not available | 23Adel | 23Udel |
| 26 | 26Abic | In progress | 26Adel | In progress |
| 27 | 27Abic 27Bbic | In progress | 27Adel 27Bdel | In progress |
| COHORT | BICEPS | | DELTOID | |
| | FSHD | CONTROL | FSHD | CONTROL |
| 28 | 28Abic 28Bbic | In progress | 28Adel 28Bdel | In progress |
| 29 | 29Abic 29Bbic | In progress | 29Adel 29Bdel | In progress |
| 30 | 30Abic 30Bbic | 30Wbic | 30Adel 30Bdel | 30Wdel |
| 31 | 31Abic | 31Ubic | 31Adel | 31Udel |
| 32 | 32Abic | 32Ubic | 32Adel | 32Udel |
| 33 | 33Abic 33Cbic | 33Ubic | 33Adel 33Cdel | 33Udel |
| 34 | 34Abic | 34Ubic | 34Adel 34Bdel | 34Udel |
| 35 | Not available | 35Ubic | 35Adel | 35Udel |
| 36 | 36Abic | 36Ubic | 36Adel | 36Udel |

SEQUENCE LISTING

```
<160> NUMBER OF SEQ ID NOS: 41

<210> SEQ ID NO 1
<211> LENGTH: 88
<212> TYPE: DNA
<213> ORGANISM: Homo sapiens

<400> SEQUENCE: 1
accaagtttc agttcatgta aacatcctac actcagctgt aatacatgga ttggctggga      60
ggtggatgtt tacttcagct gacttgga                                         88

<210> SEQ ID NO 2
<211> LENGTH: 5904
<212> TYPE: DNA
<213> ORGANISM: Homo sapiens

<400> SEQUENCE: 2
aggcagaagc cggcggcgcg cggacagcca gtcggcgccg cgcggagctg gccgctggat      60
tggctgcaac actcgcgtgt caggcggttg ctaggctccg gccgcgcgcc ccgcccttgc     120
gctcagcgcc ctctcaccgc ccggtacgtg ctcgcgcgaa ggctgcggcg cggcgctcgc     180
gcctcttagg cttggcggtg gcggcggcgg cagcttcgcg ccgaatcccc ggggagcggc     240
ggtggcggcg tcctggggcc aggaggagcg aacacctgcc gcggtcctcc cgccggcgct     300
gggcacacga ctgtctatcc cagatggctg cactggccta ggacagacgg ttcttccccc     360
agtacgtcaa gaccctggag ggtgcaagct acagaacagc tgggctcctg cattcctccc     420
agaccctgtc ttcagtagga caacaggcaa caaacttaaa tttgggtcaa gcgattcccc     480
tgcctcagct tcctgagtag ctgggattac agatagccct gggatctcct gaatttccag     540
gttgggctac tcaggcatgg attgactcct acagttcagg cggatggaga tcccaccaac     600
ccacagctta attcttcaga tgctttatct tcatttctca tgtatcttca gttggcttct     660
aatgctctgt gtgctccggg atggagcagg tgtgcagagg gtgagaaccc agctctggga     720
ccaagtcact tgcttcctta cttagcaaga ctatcgactt gagcaaactt ggacctggga     780
tgaggatgtc tgtgggcctc tcgctgctgc tgcccctctg ggggaggacc tttctcctcc     840
tgctctctgt ggttatggct cagtcccact ggcccagtga accctcagag gctgtcaggg     900
actgggaaaa ccagcttgag gcatccatgc actcagtgct ctcagacctc cacgaggctg     960
ttcccacagt ggttggcatt cctgatggca cggctgtcgt cgggcgctca tttcgagtga    1020
ccattccaac agatttgatt gcctccagtg gagatatcat caaggtatca gcggcaggga    1080
aggaggcttt gccatcttgg ctgcactggg actcacagag ccacaccctg gagggcctcc    1140
cccttgacac tgataagggt gtgcattaca tttcagtgag cgctacacgg ctggggcca    1200 acgggagcca catcccccag acctccagtg tgttctccat cgaggtctac cctgaagacc    1260
acagtgagct gcagtcggtg aggacagcct ccccagaccc tggtgaggtg gtatcatctg    1320
```

```
cctgtgctgc ggatgaacct gtgactgttt tgacggtgat tttgatgcc gacctcacca   1380
agatgacccc aaagcaaagg attgacctcc tgcacaggat gcggagcttc tcagaagtag   1440
agcttcacaa catgaaatta gtgccggtgg tgaataacag actatttgac atgtcggcct   1500
tcatggctgg cccgggaaat gcaaaaaagg tggtggagaa tggggccctt ctctcctgga   1560
agctgggctg ctccctgaac cagaacagtg tgcctgacat tcatggtgta gaggcccctg   1620
ccagggaggg cgcaatgtct gctcagcttg gctaccctgt ggtgggttgg cacatcgcca   1680
ataagaagcc ccctcttccc aaacgcgtcc ggaggcagat ccatgctaca cccacacctg   1740
tcactgccat tgggccccca accacggcta tccaggagcc cccatccagg atcgtgccaa   1800
cccccacatc tccagccatt gctcctccaa cagagaccat ggctcctcca gtcagggatc   1860
ctgttcctgg gaaacccacg gtcaccatcc ggactcgagg cgccattatt caaaccccaa   1920
ccctaggccc catccagcct actcgggtgt cagaagctgg caccacagtt cctggccaga   1980
ttcgcccaac gatgaccatt cctggctatg tggagcctac tgcagttgct accctctcca   2040
caaccaccac caagaagcca cgagtatcca caccaaaacc agcaacgcct tcaactgact   2100
ccaccaccac cacgactcgc aggccaacca agaaaccacg gacaccccgg ccagtgcccc   2160
gggtcaccac caaagtttcc atcaccagat ggaaactgc ctcaccgcct actcgtattc   2220
gcaccaccac cagtggagtg cccgtggcg gagaacccaa ccagcgccca gagctcaaga   2280
accatattga cagggtagat gcctggggttg gcacctactt tgaggtgaag atcccgtcag   2340
acactttcta tgaccatgag gacaccacca ctgacaagct gaagctgacc ctgaaactgc   2400
gggagcagca gctggtgggc gagaagtcct gggtacagtt caacagcaac agccagctca   2460
tgtatggcct tcccgacagc agccacgtgg gcaaacacga gtatttcatg catgccacag   2520
acaaggggggg cctgtcggct gtggatgcct tcgagatcca cgtccacagg cgcccccaag   2580
gggatagggc tcctgcaagg ttcaaggcca agtttgtggg tgaccggca ctggtgttga   2640
atgacatcca caagaagatt gccttggtaa agaaactggc cttcgccttt ggagaccgaa   2700
actgtagcac catcaccctg cagaatatca cccgggggctc catcgtggtg aatggacca   2760
acaacacact gcccttggag ccctgcccca aggagcagat cgctgggctg agccgccgga   2820
tcgctgagga tgatggaaaa cctcggcctg ccttctccaa cgccctagag cctgactttta   2880
aggccacaag catcactgtg acgggctctg gcagttgtcg gcacctacag tttatccctg   2940
tggtaccacc caggagagtg ccctcagagg cgccgcccac agaagtgcct gacagggacc   3000
ctgagaagag cagtgaggat gatgtctacc tgcacacagt cattccggcc gtggtggtcg   3060
cagccatcct gctcattgct ggcatcattg ccatgatctg ctaccgcaag aagcggaagg   3120
gcaagcttac ccttgaggac caggccacct tcatcaagaa ggggggtgcct atcatctttg   3180
cagacgaact ggacgactcc aagccccccac cctcctccag catgccactc attctgcagg   3240
aggagaaggc tcccctaccc cctcctgagt accccaacca gagtgtgccc gagaccactc   3300
ctctgaacca ggacaccatg ggagagtaca cgcccctgcg ggatgaggat cccaatgcgc   3360
ctccctacca gccccaccg cccttcacag cacccatgga gggcaagggc tcccgtccca   3420
agaacatgac cccataccgg tcacctcctc cctatgtccc accttaaccc gcaagcgcct   3480
gggtggaggc agggtagggc aggggctgg agacgacatg gtgttgtctg tggagaccgg   3540
tggcctgcag accattgccc accgggagcc gacacctgac ctagcacaca ctgacacagg   3600
ggcctggaca agcccgccct ctctggtcct cccaaacccc aaagcagctg gagagacttt   3660
```

| | |
|---|---|
| gggggactttt ttatttttat tttttgccta acagcttttg gtttgttcat agagaattct | 3720 |
| tcgcttcatt tttgatggct ggctctgaaa gcaccatgtg gagtggaggt ggagggagcg | 3780 |
| aggaaccatg aatgaactcg caggcagtgc cgggcggccc cctggctctc tgcgttttgc | 3840 |
| ctttaacact aactgtactg ttttttctat tcacgtgtgt ctagctgcag gatgtaacat | 3900 |
| ggaaaacagt aactaaagat taaattcaaa ggactttcag aagttaaggt taagttttta | 3960 |
| cgtttaatct gctgtttacc taaacttgta tgtataattt ttgggtgggt atggggaatt | 4020 |
| gctttgctaa aaataagctc ccagggtgtt tcaaacttag agaagaccaa gggacagtat | 4080 |
| tttttatcaa aggaatacta ttttttcaca ctacgtcaac ttggttgctc tgatacccca | 4140 |
| gagcctgatt gggggcctcc cggccctggc tcacgccaag tccctggtgc tgggtttgct | 4200 |
| ctcccgctgt tgccaggggc tggaagctgg aggggtctct tgggccatgg acatccccac | 4260 |
| ttccagccca tgtacactag tggcccacga ccaagggtc ttcatttcca tgaaaaaggg | 4320 |
| actccaagag gcagtggtgg ctgtggcccc caactttggt gctccagggt gggccagctg | 4380 |
| cttgtggggg cacctgggag gtcaaaggtc tccaccacat caacctattt tgttttaccc | 4440 |
| tttttctgtg cattgttttt tttttcctc ctaaaaggaa tatcacggtt ttttgaaaca | 4500 |
| ctcagtgggg gacattttgg tgaagatgca atatttttat gtcatgtgat gctcttccct | 4560 |
| cacttgacct tggccgcttt gtcctaacag tccacagtcc tgccccgacc caccccatcc | 4620 |
| cttttctctg gcactccagt cccaggcctt gggcctgaac tactgaaaaa ggtctggcgg | 4680 |
| ctggggagga gtgccagcaa tagttcataa taaaaatctg ttagctctca aagctaattt | 4740 |
| tttactaaag ttttatata gcctcaaatt gttttattaa aaaaaagatt taaaatggtg | 4800 |
| atgcttacag cagtttgtac gagctcttaa gtgttgattc catggaactg acggctttgc | 4860 |
| ttgttttgat tcttttcccc ctactttttcc taatggttta aattctggaa ttacactggg | 4920 |
| gttcttttgc ctttttagc agaacatccg tccgtccatc tgcatctctg tcccatgact | 4980 |
| caggggcgcc cactctgctt cgattctcct cctgtggaag aaaccatttt gagcatgact | 5040 |
| tttcttgatg tctgaagcgt tattttgggt acttttaagg gaggaatgcc tttcgcaata | 5100 |
| atgtatccat tccctgattg agggtgggtg ggtggaccca ggctcccttt gcacacagag | 5160 |
| cagctacttc taagccatat cgactgtttt gcagaggatt tgtgtgtgct gcctcaggag | 5220 |
| gggagggctg gtaggagggg gggagaggtc tctgtcctac tgctctccag agggcatttc | 5280 |
| cccttgcgcc ttctcccaca gggcccagcc cctctcccct gccccagtcc caggggta | 5340 |
| ctctggagtg agcagtgccc ctgtggggga gcctgtaaat gcgggctcag tggaccactg | 5400 |
| gtgactgggc tcatgcctcc aagtcagagt ttccctggtg ccccagagac aggagcacaa | 5460 |
| gtgggatctg acctggtgag attatttctg atgacctcat caaaaaataa acaattccca | 5520 |
| atgttccagg tgagggcttt gaaaggcctt ccaaacagct ccgtcgcccc tagcaactcc | 5580 |
| accattgggc actgccatgc agagacgtgg ctggcccaga atggcctgtt gccatagcaa | 5640 |
| ctggaggcga tggggcagtg aacagaataa aacagcaac aatgcctttg caggcagcct | 5700 |
| gctcccctga gcgctgggct ggtgatggcc gttggactct gtgagatgga gagccaatct | 5760 |
| cacattcaag tgttcaccaa ccactgatgt gttttatttt ccttctatat gattttaaga | 5820 |
| tgtgttttct gcattctgta aagaaacata tcaaactaaa taaaagcagt gtctttatta | 5880 |
| caacgcaaaa aaaaaaaaaa aaaa | 5904 |

<210> SEQ ID NO 3
<211> LENGTH: 2229

<212> TYPE: DNA
<213> ORGANISM: Homo sapiens

<400> SEQUENCE: 3

```
tccggcgccc cgcgccgcct ccgctgcggg tcgggagcgc gcgtctccgc cgcacctcgg      60
atctaggagc tactcgcccg gccctgggcg gtgggaggcg gcggcggcgg cggcgctcgc     120
gcacctcgga ggagccagga gccggaacca gggccgagcc cgcgggccgg ggctagccag     180
ccggtcggag atgtccgccc agaggttaat ttctaacaga acctcccagc aatcggcatc     240
taattctgat tacacctggg aatatgaata ttatgagatt ggaccagttt cctttgaagg     300
actgaaggct cataaatatt ccattgtgat tggattttgg gttggtcttg cagtcttcgt     360
gattttatg tttttgtgc tgaccttgct gaccaagaca ggagccccac accaagacaa      420
tgcagagtcc tcagagaaga gattcagaat gaacagcttt gtgtcagact ttggaagacc     480
tctggagcca gataaagtat tttctcgcca aggcaacgag gagtccaggt ctctctttca     540
ctgctacatc aatgaggtgg aacgcttgga cagagccaaa gcttgtcacc agaccacagc     600
ccttgacagt gacgtccaac tccaggaagc catcagaagc agtgggcagc cagaggagga     660
gctgaacagg ctcatgaagt ttgacatccc caactttgtg aacacagacc agaactactt     720
tgggaggat gatcttctga tttctgaacc acctattgtt ctggaaacta gccactttc      780
ccagacctca cacaaagacc tggattgaga aacatgctct gtaaagggtc ttcctgaaga     840
tgtggattct atctttatgt agcaagaaat ctacatccac caaaattgtg tgtgtttggg     900
ggagagagag acatagagat agagacagag aggcagagaa gagacccctt tagaagagag     960
ctgagctgat taagctgagt ggttttttgt tttgttttgt ttttgctttt taatacattt    1020
ggagctttgg gagtattaaa gtatttacac caagcttgtc caacccgtgg catgtgtccc    1080
aggacagctt tgaatgtggc ccaatacaaa ttttaaactt tattaaaaca tgagttttgt    1140
tttttttttt gctatttttt ttaaagctcg tcagctatcg ttagtgttag tgtactttat    1200
gtgtggccca agacaactct tcttccagtg tggcacaggg aagctaaaag attggacacc    1260
tctgatttat actagctcgt tttgcttgtt gaaaaatttg gccaaatacc tattgtcagc    1320
attcttgggt gaggattagc ctaccatgtt ctaatctggc cctgccacta ctatgctcta    1380
cctttggtga gttgctttac ctctctgggc tgccccattt ttaactgtag gttgacaggt    1440
ctagagtgat ccatcccacc tctaatattt tgtgaattta tgacttttgcc ttcagatgag   1500
gctgagctat acataaaaca gtataaacta gggtactgcc tcgtatctct tgtaggctct    1560
ctcaaatctc tgtaccttcc acttaaccct aattgagcca agctttagtc aggggatctg    1620
gttgtctacc agaatgtcag gagactcatc ttacacagtc atggtggcca atgtttctgg    1680
tgggttgtgc tgaaacagct cttctgagaa cttccaacca cccatgctct aacctggaga    1740
cagccatccc ctgcctcaga ataagtacca attcgtagta catgtatggt actcttgtcc    1800
ccaagaaatg ttaggaagct tgtcagctga atgagaggag gtgccttctg ggtatctctg    1860
tgttggtgta tctgtgccat ggctacagaa caagaaaaa tactatttgc catgctatta     1920
ccttggcaga tgtgtaggtg atagtcatct ggctttgagc tgagatggtc agtgggttgt    1980
aaattcccca ctagcagata ttcagggtgg cctgagttat gtaaacaagt gagcaacaca    2040
gctttaattt catggaggaa tcaaagctgc acactggtat taaaacaact tgattttgcg    2100
cacacagttg catgcatggc aagctgttaa cctctgggtg gcattttcat tatgaatttg    2160
ttcaccacct gtcttgctta agctacaaaa taaatgcatt tgactgcaca gaaaaaaaaa    2220
``` aaaaaaaaa                                                             2229

<210> SEQ ID NO 4
<211> LENGTH: 409
<212> TYPE: DNA
<213> ORGANISM: Homo sapiens

<400> SEQUENCE: 4

| | | | | | |
|---|---|---|---|---|---|
| gtgcagagac | tcaagacaga | tatgaccacg | tgaagagaca | actgtaaaac | aagtggaatt |  60 |
| agagaataaa | atcccagcac | gatgttcctc | actggagaca | ccagtccagc | tgaggacaat | 120 |
| agagaagcca | cccttcctca | atgttcactt | ccagaattat | atgcatgtat | tgagaatttt | 180 |
| aataaggaga | gcaagaaatc | aaatcttcta | aaaatgcatg | gtatttcact | taacgaagca | 240 |
| caggaagtac | ttgctagaaa | cctgaatgtc | atgtcattca | ccaggggcgc | tgatgtgaga | 300 |
| ggagatctcc | aacctgttat | cagtgtcaat | aaaatgaaca | agcctggaaa | acatagaaag | 360 |
| accccatctc | caaaaataaa | taaataaata | aataaataaa | taaaaatta | | 409 |

<210> SEQ ID NO 5
<211> LENGTH: 3570
<212> TYPE: DNA
<213> ORGANISM: Homo sapiens

<400> SEQUENCE: 5

| | | | | | |
|---|---|---|---|---|---|
| ggccggctgc | tcaagtggga | cgggggtcag | agctttgtgg | agggaagaaa | aacctggagg |  60 |
| gggcaggaga | gtaaaagaa  | gaaacccagg | cagacaggca | gttggacaca | ctgaggaaga | 120 |
| ccccccacga | gtgggaaccc | cctggaagga | acacaccggc | cccggccccc | aggaagggag | 180 |
| cacaatggag | gccgctcatg | ctaaaaccac | ggaggaatgt | ttggcctatt | tgggggtgag | 240 |
| tgagaccacg | ggcctcaccc | cggaccaagt | taagcggaat | ctggagaaat | acggcctcaa | 300 |
| tgagctccct | gctgaggaag | ggaagaccct | gtgggagctg | gtgatagagc | agtttgaaga | 360 |
| cctcctggtg | cggattctcc | tcctggccgc | atgcatttcc | ttcgtgctgg | cctggtttga | 420 |
| ggaaggtgaa | gagaccatca | ctgcctttgt | tgaacccttt | gtcatcctct | tgatcctcat | 480 |
| tgccaatgcc | atcgtggggg | tttggcagga | gcggaacgca | gagaacgcca | tcgaggccct | 540 |
| gaaggagtat | gagccagaga | tggggaaggt | ctaccgggct | gaccgcaagt | cagtgcaaag | 600 |
| gatcaaggct | cgggacatcg | tccctgggga | catcgtggag | gtggctgtgg | gggacaaagt | 660 |
| ccctgcagac | atccgaatcc | tcgccatcaa | atccaccacg | ctgcgggttg | accagtccat | 720 |
| cctgacaggc | gagtctgtat | ctgtcatcaa | acacacggag | cccgttcctg | acccccgagc | 780 |
| tgtcaaccag | gacaagaaga | acatgctttt | ctcgggcacc | aacattgcag | ccggcaaggc | 840 |
| cttgggcatc | gtggccacca | ctggtgtggg | caccagagatt | gggaagatcc | gagaccaaat | 900 |
| ggctgccaca | gaacaggaca | agaccccctt | gcagcagaag | ctggatgagt | tggggagca  | 960 |
| gctctccaag | gtcatctccc | tcatctgtgt | ggctgtctgg | cttatcaaca | ttggccactt | 1020 |
| caacgacccc | gtccatgggg | gctcctggtt | ccgcggggcc | atctactact | ttaagattgc | 1080 |
| cgtggccttg | gctgtggctg | ccatccccga | aggtcttcct | gcagtcatca | ccacctgcct | 1140 |
| ggccctgggt | accgtcgga  | tggcaaagaa | gaatgccatt | gtaagaagct | tgccctccgt | 1200 |
| agagaccctg | ggctgcacct | ctgtcatctg | ttccgacaag | acaggcaccc | tcaccaccaa | 1260 |
| ccagatgtct | gtctgcaaga | tgtttatcat | tgacaaggtg | gatgggggaca | tctgcctcct | 1320 |
| gaatgagttc | tccatcaccg | gctccactta | cgctccagag | ggagaggtct | tgaagaatga | 1380 |
| taagccagtc | cggccagggc | agtatgacgg | gctggtggag | ctggccacca | tctgtgccct | 1440 |

```
ctgcaatgac tcctccttgg acttcaacga ggccaaaggt gtctatgaga aggtcggcga    1500
ggccaccgag acagcactca ccaccctggt ggagaagatg aatgtgttca acacggatgt    1560
gagaagcctc tcgaaggtgg agagagccaa cgcctgcaac tcggtgatcc gccagctaat    1620
gaagaaggaa ttcaccctgg agttctcccg agacagaaag tccatgtctg tctattgctc    1680
cccagccaaa tcttcccggg ctgctgtggg caacaagatg tttgtcaagg gtgccctga    1740 gggcgtcatc gaccgctgta actatgtgcg agttggcacc accgggtgc cactgacggg     1800 gccggtgaag gaaaagatca tggcggtgat caaggagtgg ggcactggcc gggacaccct    1860
gcgctgcttg gccctggcca cccgggacac ccccccgaag cgagaggaaa tggtcctgga    1920
tgactctgcc aggttcctgg agtatgagac ggacctgaca ttcgtgggtg tagtgggcat    1980
gctggaccct ccgcgcaagg aggtcacggg ctccatccag ctgtgccgtg acgccgggat    2040
ccgggtgatc atgatcactg gggacaacaa gggcacagcc attgccatct gccggcgaat    2100
tggcatcttt ggggagaacg aggaggtggc cgatcgcgcc tacacgggcc gagagttcga    2160
cgacctgccc ctggctgaac agcgggaagc ctgccgacgt gcctgctgct cgcccgtgt    2220 ggagccctcg cacaagtcca agattgtgga gtacctgcag tcctacgatg agatcacagc    2280
catgacaggt gatggcgtca atgacgcccc tgccctgaag aaggctgaga ttggcattgc    2340
catgggatct ggcactgccg tggccaagac tgcctctgag atggtgctgg ctgacgacaa    2400
cttctccacc atcgtagctg ctgtggagga gggccgcgcc atctacaaca acatgaagca    2460
gttcatccgc tacctcattt cctccaacgt gggcgaggtg gtctgtatct tcctgaccgc    2520
tgccctgggg ctgcctgagg ccctgatccc ggtgcagctg ctatgggtga acttggtgac    2580
cgacgggctc ccagccacag ccctgggctt caacccacca gacctggaca tcatggaccg    2640
ccccccccgg agccccaagg agcccctcat cagtggctgg ctcttcttcc gctacatggc    2700 aatcggggc tatgtgggtg cagccaccgt gggagcagct gcctggtggt tcctgtacgc    2760
tgaggatggg cctcatgtca actacagcca gctgactcac ttcatgcagt gcaccgagga    2820
caacacccac tttgagggca tagactgtga ggtcttcgag gccccgagc ccatgaccat    2880 ggccctgtcc gtgctggtga ccatcgagat gtgcaatgca ctgaacagcc tgtccgagaa    2940
ccagtccctg ctgcggatgc caccctgggt gaacatctgg ctgctgggct ccatctgcct    3000
ctccatgtcc ctgcacttcc tcatcctcta tgttgacccc ctgccgatga tcttcaagct    3060
ccgggccctg gacctcaccc agtggctcat ggtcctcaag atctcactgc agtcattgg    3120 gctcgacgaa atcctcaagt tcgttgctcg gaactaccta gagggataac tgttccccct    3180
cctccatctc tgagcccgtg tcacagatcc agaagatgaa agaaggaagt gagcatcctt    3240
ttgctctgtc ctccccaccc cgatagtgac acatcttcag gcagagctgt ggcacagacc    3300
cccgtcctgt cccccacacc cgtgtcatgt gtctgtttat aaacatgtcc ccttccctt     3360 ccttcccct cggccacccg cctccctctc aaccttgtaa attccccttc caacccga      3420 ggggcttgca gggacaaggc gaccgactgc gctgagctgc ttatttattg aaaataaacg    3480
acggaaaagt ctggccttgc ctctgtgcaa gcttggaggc ctgggtcgcc gctgtgaaaa    3540
aaaaaaaaaa aaaaaaaaaa aaaaaaaaa                                      3570

<210> SEQ ID NO 6
<211> LENGTH: 5779
<212> TYPE: DNA
<213> ORGANISM: Homo sapiens
```

<400> SEQUENCE: 6

```
aggcaaaggg cggggcgcgc gcgtcgggaa gatggcgcta cgtctgctgc ggagggcggc      60
gcgcggagct gcggcggcgg cgctgctgag gctgaaagcg tctctagcag ctgatatccc     120
cagacttgga tatagttcct catcccatca caagtacatc ccccggaggg cagtgcttta     180
tgtacctgga aatgatgaaa agaaaataaa gaagattcca tccctgaatg tagattgtgc     240
agtgctcgac tgtgaggatg gagtggctgc aaacaaaaag aatgaagctc gactgagaat     300
tgtaaaaact cttgaagaca ttgatctggg ccctactgaa aaatgtgtga gagtcaactc     360
agtttccagt ggtctggcgg aagaagacct agagacccett ttgcaatccc gggtccttcc     420
ttccagcctg atgctaccaa aggtggaaag tcctgaagaa atccagtggt ttgcagacaa     480
attttcattc cacttaaaag gccgaaaact tgaacaacca atgaatttaa tccctttgt     540
ggaaactgca atgggtttgc tcaattttaa ggcagtgtgt gaagaaaccc tgaaggtcgg     600
gcctcaagta ggtctctttc tagatgcagt cgttttggga ggagaagact ttcgagccag     660
cataggtgca acaagtagta agaaaaccct ggatattctc tacgcccggc aaaagattgt     720
tgtcatagcg aaagcctttg gtctccaagc catagatctg gtgtacattg actttcgaga     780
tggagctggg ctgcttagac agtcacgaga aggagccgcc atgggcttca ctggtaagca     840
ggtgattcac cctaaccaaa ttgccgtggt ccaggagcag ttttctcctt ccctgaaaa     900
aattaagtgg gctgaagaac tgattgctgc ctttaaagaa catcaacaat taggaaaggg     960
ggcctttact ttccaaggga gtatgatcga catgccatta ctgaagcagg cccagaacac    1020
tgttacgctt gccacctcca tcaaggaaaa atgatctgtt aaatgaagct gtcatcaggc    1080
taaagggtat tgaagctgca gagggatcaa cttgtgcttg ccagaggacg ccaatgaagt    1140
ttgaaacacc aacaatcaga gattttgttt ctgttcctca ttaaatcatg agcttttgtg    1200
ccgagactct ggacgactgt tccttaagaa attaacagaa tgggaagttt taaactctac    1260
accaaccttt tcatgaccta cacagcagca acgctgctac tcttagacaa acaccgcggg    1320
gaaggctgtt ctgtttattt aaatttgtaa atagaaaaca gttgttttt actttcattt    1380
ttcacctcct cctacgccct tttggattat ttcctctgcg gccccctagca tgagccccaa    1440
ccaggcctcc ccttttcccc acttctctca attcccacag gaagcccgag aggtgaggag    1500
ctgaggttag acaccaggag aggcaccatc acacaaaagc gcggccgcag agtcccaccg    1560
ccaccaggcg accccaccc agagagggac agacatgcgg ggagccagca ccgggcaaga    1620
tggctctggg gatcctcatt ctgtgaagac accaactcat ttctcaaaca caggatccag    1680
gagacagata gctcctaaat ggagatggca catgctccgt ggggtccctc atagaggagt    1740
gccacccctcc acactggcca cgctgggctg ccccagagcg ccagaaagg aaggtgggag    1800
ctagccccat cctcactcag aggccggaag gaggaagatg gcatctcgcc aacttcagag    1860
ccgaatggcc tctagccaca ctgcttccag accccagacg gggcagcagc agcagttccc    1920
agaggagcac ccattgttgc agctaggacc caccaaggat gggactcctg gagtcaggtg    1980
cacaccaggt aacccaggac cacgctgtgc accccccagtc tgcccctctg ctcagaacac    2040
agagggatgg gaggatggct tggcagtggg aaggcaaaag aaggcctctc tcactctgcc    2100
cctgccatac gcacccgctg agggtgttag aagcagtgga ggcagagctg ccctaagca    2160
aaagaagaaa ataaacctca ccttgtcctt cctatgggca gccctcaccc caatctaact    2220
aaccttccca tcctccagcc taatccaaag aagcccttgg cttgagggga tgaagggctt    2280
gcgttctagt ctccaccca gccccacagg cagccagcca gccagcccca cacagagggg    2340
```

```
cctcctcaag gcctcactgg gagcctcctg tccccagcca aggagcccta cagacctggg   2400
gaaaagcagg cccctccgca aggccctgg gtggtgcgga ggccggaccg gctaggcctc    2460
ccgctgctgg ccactcccag gccacgggtt cctaggtccc aaccacattg gactgctcgc   2520
cacgccactg ccctcatccc aaactgcttt gttcaaacaa aaccaccttg tttcagtctc   2580
cccaaatgtc cagttcatta tcttcctcat aacccatggt ccctattagg gtaggatcat   2640
gagactaaga cctatgagag ccacaaatct ggaccaaagt cccattccct gaacagagac   2700
ccaaacgacg agggtcccag aagagagttc agtcctgatc agaaacccat ggtgccttag   2760
tccttgaaga acaaaactct aggaagaaga tgctggaagg caaagggtat tcccctctt    2820 tccccacccg cgtctctgtg gtgccatggg tgggcccagg taccctggga aggtgggag    2880 agcagtcaag ggtgggtgtg tgatctccac tgggctcact gggcaccccc gacacgggga   2940
agtgagagct gcccgactcc tgagccaggc gtgggtgaca ggaagaggac cttgcagcta   3000
atctgattca ttagaaacca tacctgttta tgttttgtgt agctcatcac aagccgctta   3060
gccatatcac ccccgttatt aattcttggg gtctaaatta tgggtaacac tattaaaaca   3120
ttatcagaac taatgagaaa caattactta gaaaatgagc cgggacaaga ctgagttggg   3180
aacatcagtg gtgatcactg tagattagtt taataaatca tcaggtgcaa ggcaagactg   3240
actgtatgta tgcaaagccc cgtcacggga aaatgaaatt gagattttt ttttttgcat    3300 aattttttca ttaatctcaa taggacccgt gtggtgtaga ttgctttatt cccctaatac   3360
cttgcctgag gcggggggg ggggggtgc ccaataatgt cttcattgtt ttactgaggt     3420
cttaatgaca atctgtgaca acctcatttt aatgtataga ggattatatc aatacagtca   3480
tgttttattg aaatggtgaa gggaactcca gtcagagtca ggcagtgtct gtgagcacaa   3540
gttaggaagt ttctcggcat ccgggagcgt tcccgtctga tgtcccagtg ttagtcctcc   3600
cggccgccct cccctcctct cctccaggga cggctgggaa acagtcctg cgggatgaag    3660 acttcaccgc ctccgatttg aatttgaaag taactccttc cgtggcatat ttcgctgggc   3720
agatagaaca aaccatgtcg ttttcccccg tctctaaaat agacatatta ttatcattca   3780
cacttttgca cccggtcgtt ttgcgggagt tcgggaaact gactttcttc attgggaca    3840 ttgtaatttt ctgatgatgc cacgaggaga aaaaaatac gggtttgttt taattggaag    3900
gaccttccgc ttttatgatt tcggtttacc ttggaaaact gaatcttctg tgttttattt   3960
ctttcctcta gtactagaaa agcaatgaat taattgcaca aaacaggttc tgagacggcc   4020
cgcaggcccc gagctcgtgg acgcggccga gggtcgggtg tgacccgcgg agccgctgcc   4080
aggcttccca gctcgtcttc gcggggaggc gggaggcagg accagacccc agcatttcag   4140
cgtgaaagtc ttcgcctttc tttccgcgct gtctttcccg cgggcggagc ggcgtacctg   4200
agcgcggtcc ccacggagga tcagtgactt tcccagaccc cgcgggcgag cccgcgcttg   4260
ggacccggca gctctgcgcg ggctggtttt ggaggggtg gtgttcgttt gtttaaattc    4320
cagttgttat ttggcagcat atcgccttcc gagtcagtaa gaattgccca cgacgtaaag   4380
agcgacttgc aggaagggc cgaagccgtc gttagcgccc gggcggcggc ggccactcga    4440
accccgtttc cgccaagcgc gctgcaacct gcggggcgag ttcgttttgt tttgccaaaa   4500
tcatttgggg acttctttgt cattcatgcc cttccttta aatgattttt attttttcc    4560 actgtaagtg accggctggg tttgactttt gcttcttccg acggaagggc accgcgagcc   4620
ggggtgggcg gccccgcggg caggaggagc gcggggtaca cgcggtggcc gcagacgccg   4680
```

| | |
|---|---|
| agccctgcgg agccccgagg cctcgtcgcc cgcgccccg gtgcgcgcgg agccggggcc | 4740 |
| gaggccgggc caggaggagt gtggcggccc aggaggcctg gactgtgggc cctgctcgcc | 4800 |
| cgcccgccgc gggccgcccg gagcccgcgc gcctgtcgcg cagcccggct gtaatggtgg | 4860 |
| cagatcaaag gcgcccccgt gtcccgcgg agcccgggac aatcccgcgc ctttgtgcgc | 4920 |
| tgttgctagg agcccgagaa actaagagaa agtgtcagga gcatgttaat cagactcgtt | 4980 |
| acactgtaac aataacgtct ctctcgggtc tcccaggccc cagtacccc gcgcaccctg | 5040 |
| cgcgcaggcc ggacacctgc gcagggccct tgcgcccgcc ctggggtccc gccggccctg | 5100 |
| gggtccctgc agccccgaat ccgcacccga gccacgcgga acgactagcc ccgaggggcc | 5160 |
| ccgcaggctc ccggtgcagc tccctggtcg tggtctcctt gaccgaagcc ccggcctcac | 5220 |
| accgcctggc cgcgagcccg agggacgcag ggacgatccc ggtcccctgc ttttcagtcc | 5280 |
| tccagtcgaa tcgcccactt tgttcaatca cagtattcga atcaagagga aaatgaacat | 5340 |
| tccctttatg gtagcttttt ggttatgagt tttggcaaaa ctgttaaatc aactttgccg | 5400 |
| atttcccttg ggaatccctg gaggccactc taagtggtaa tcccaagttt aagaaggaaa | 5460 |
| tggggaaatt ttgctgagag taaagatgtc gccgaacttt ttgaagggat ttgcttcatt | 5520 |
| cattcattta gtcattcaac agacacctgt tgaacccgac tgggtgccag aggggccagt | 5580 |
| cacaggactt attccagatg aactttttctt ttgaaattag aatgcccttg tggaagccaa | 5640 |
| aggaggagca gaggcctaaa ataatgtcaa gtgtcaaagc aaaaagaagt gccattggct | 5700 |
| actacagtgt gtgatgataa caagagaggt gcgaattagg aattaaaaac gtttgaaaaa | 5760 |
| ctacaggcca aaaaaaaaa | 5779 |

<210> SEQ ID NO 7
<211> LENGTH: 5006
<212> TYPE: DNA
<213> ORGANISM: Homo sapiens

<400> SEQUENCE: 7

| | |
|---|---|
| gctgctgatc acttacaatc tgacaacact tacaatctac tcagaacaac ctctctctct | 60 |
| ccagcagaga gtgtcacctc ctgctttagg accatcaagc tctgctaact gaatctcatc | 120 |
| ctaattgcag gatcacattg caaagctttc actctttccc accttgcttg tgggtaaatc | 180 |
| tcttctgcgg aatctcagaa agtaaagttc catcctgaga atatttcaca agaatttcc | 240 |
| ttaagagctg gactgggtct tgaccccctga atttaagaaa ttcttaaaga caatgtcaaa | 300 |
| tatgatccaa gagaaaatgt gatttgagac tggagacaat tgtgcatatc gtctaataat | 360 |
| aaaaacccat actagcctat agaaaacaat atttgaaaga ttgctaccac taaaaagaaa | 420 |
| actactacaa cttgacaaga ctgctgcaaa cttcaatttg tcaaccacaa cttgacaagg | 480 |
| ttgctataaa acaagattgc tacaacttct agtttatgtt atacagcata tttcattttg | 540 |
| gcttaatgat ggagaaaaag tgtaccctgt atttttctggt tctcttgcct ttttttatga | 600 |
| ttcttgttac agcagaatta gaagagagtc ctgaggactc aattcagttg ggagttacta | 660 |
| gaaataaaat catgacagct caatatgaat gttaccaaaa gattatgcaa gaccccattc | 720 |
| aacaagcaga aggcgtttac tgcaacgaaa cctgggatgg atggctctgc tggaacgatg | 780 |
| ttgcagcagg aactgaatca atgcagctct gccctgatta ctttcaggac tttgatccat | 840 |
| cagaaaagt tacaaagatc tgtgaccaag atggaaactg gtttagacat ccagcaagca | 900 |
| acagaacatg gacaaattat acccagtgta atgttaacac ccacgagaaa gtgaagactg | 960 |
| cactaaattt gttttaccctg accataattg gacacggatt gtctattgca tcactgctta | 1020 |

```
tctcgcttgg catattcttt tatttcaaga gcctaagttg ccaaaggatt accttacaca    1080
aaaatctgtt cttctcattt gtttgtaact ctgttgtaac aatcattcac ctcactgcag    1140
tggccaacaa ccaggcctta gtagccacaa atcctgttag ttgcaaagtg tcccagttca    1200
ttcatcttta cctgatgggc tgtaattact tttggatgct ctgtgaaggc atttacctac    1260
acacactcat tgtggtggcc gtgtttgcag agaagcaaca tttaatgtgg tattattttc    1320
ttggctgggg atttccactg attcctgctt gtatacatgc cattgctaga agcttatatt    1380
acaatgacaa ttgctggatc agttctgata cccatctcct ctacattatc catggcccaa    1440
tttgtgctgc tttactggtg aatctttttt tcttgttaaa tattgtacgc gttctcatca    1500
ccaagttaaa agttacacac caagcggaat ccaatctgta catgaaagct gtgagagcta    1560
ctcttatctt ggtgccattg cttggcattg aatttgtgct gattccatgg cgacctgaag    1620
gaaagattgc agaggaggta tatgactaca tcatgcacat ccttatgcac ttccagggtc    1680
ttttggtctc taccattttc tgcttcttta atggagaggt tcaagcaatt ctgagaagaa    1740
actggaatca atacaaaatc caatttggaa acagcttttc caactcagaa gctcttcgta    1800
gtgcgtctta cacagtgtca acaatcagtg atggtccagg ttatagtcat gactgtccta    1860
gtgaacactt aaatggaaaa agcatccatg atattgaaaa tgttctctta aaaccagaaa    1920
atttatataa ttgaaaatag aaggatggtt gtctcactgt tttgtgcttc tcctaactca    1980
aggacttgga cccatgactc tgtagccaga agacttcaat attaaatgac tttttgaatg    2040
tcataaagaa gagccttcac atgaaattag tagtgtgttg ataagagtgt aacatccagc    2100
tctatgtggg aaaaagaaa tcctggtttg taatgtttgt cagtaaatac tcccactatg    2160
cctgatgtga cgctactaac ctgacatcac caagtgtgga attggagaaa agcacaatca    2220
acttttctga gctggtgtaa gccagttcca gcacaccatt gcatgaattc acaaacaaat    2280
ggctgtaaaa ctaaacatac atgttgggca tgattctacc cttattgccc caagagacct    2340
agctaaggtc tataaacatg aagggaaaat tagcttttag ttttaaaact ctttatccca    2400
tcttgattgg ggcagttgac tttttttttg cccagagtgc cgtagtcctt tttgtaacta    2460
ccctctcaaa tggacaatac cagaagtgaa ttatccctgc tggctttctt ttctctatga    2520
aaagcaactg agtacaattg ttatgatcta ctcatttgct gacacatcag ttatatcttg    2580
tggcatatcc attgtggaaa ctggatgaac aggatgtata atatgcaatc ctacttctat    2640
atcattagga aaacatctta gttgatgcta caaaacacct tgtcaacctc ttcctgtctt    2700
accaaacagt ggggagggaat tcctagctgt aaatataaat tttgtccctt ccatttctac    2760
tgtataaaca aattagcaat cattttatat aaagaaaatc aatgaaggat ttcttatttt    2820
cttgaatttt tgtaaaaaga aattgtgaaa atgagcttg taaatactcc attatttat    2880
tttatagtct caaatcaaat acatacaacc tatgtaattt ttaaagcaaa tatataatgc    2940
aacaatgtgt gtatgttaat atctgatact gtatctgggc tgattttta aataaaatag    3000
agtctggaat gctatatttg gtaaatattt taaagacaac cagatgccag catcagaagt    3060
ctgtttgaga actaagagaa cagaaacatc tatcataaga tatatttatt ttaaaaacac    3120
aaggtcacta ttttattgaa tatatttgtt ttgataactc ataccttaat aataggtgtg    3180
tttgacatat ttctttttc attttgacaa tgaactcaca ttctaatcca gaaattttaa    3240
acaactactg tgataaatac caatctgcta cttttataga ttttacccca ttaaaatatt    3300
actttactga cttttactat gtgaagatat atagctttgg aaatgtccca ggctattcaa    3360
```

```
gaaatataaa aaactagaag gatactatat ataccatata caatgcttta atattttaat    3420
agagctactg tatataatac aaattaggga aatacttgaa tatatcattg agaaaaaatt    3480
attgtcagat cttactgaat tattgtcaga ctttattaaa taaagataga agaaaacctt    3540
gctaatgaat taaagtgaaa tttgcatggg attcagtttc tctaatgtta ttttccgctg    3600
aaatctctaa agaacaagaa tgacttcaat tagtaaaagt caattttggg aaaagtcatg    3660
ggtatctgtt ttttaagtgt gtcaatctga ttaaaatgga tgaaacaaat tactcatcat    3720
aagttgtttc ttaagctgtc aatatgtcaa tagatggtga gttcagaact tatttcaaat    3780
tgctaagaca aattatctaa attcgtaaga attaacatat agaatggtct ggtcagtaca    3840
tttataattt atctatgcat gaaaaagtat tgttttgttt gaaacatgaa tttcatagca    3900
agctgccata gaaggaacg caggctgttc tagaccttca actgcctaaa ttatacaaaa     3960
attcatttta ataaactcaa ttattagcta tttattattc aaagacccat atttaaatcc    4020
tttgctgacc atgttgacat atatcagcct tcttctagac aaactgtcaa ctctcaacca    4080
tcttgacagt agaagtgaca gtaaaaaatg ttgaatgatc agagattata ttaaaaataaa   4140 catgtaattt tcaagtattt ttgttgtgct tttataatat taattctaga tcagatttat    4200
tttatagcca gggtttgtct gttgtagagt cttgaggcgt agcagtcatt catgattaat    4260
cactgttagt tttgtaccca tatatttta gaatagtttt aaatgttaga tttctcaaaa     4320
gctaaatgct acttaatatc tttgtatcat actcataaag caaagtaaat ctgacacttt    4380
ttttaaagca aacttctttg ctgtcaaaaa aataaatttg gggaaatttc tagcttttaa    4440
aatgtagatc tgcattttac tgtgattact tgtgaaagtc atattttaat tttctaaatt    4500
ctaatttgtc atttatttc ctaaagttaa tttccaatgc atttattcat aaaatattca     4560
ttctggaatg cagtgtttgt ttaaatgtaa tccaatgtat atagaattag tggtggctgt    4620
agtgctgtat ttattgctta taatttttt taaatgtgaa cttactttta attttctctt     4680
ggttttaatc tgctagtaga aaccactagt tatctgtaaa aatatattca agatattctg    4740
atcaattata acaatttatg ttatgcctag agtatatctc tatttttga ttgtatgaaa     4800 atattaaagt tatgagttaa agtttatttt cactgatatt tactacagtg ccaaataatc    4860
taatttataa acataattct tacagtaatc aatgggatac ttctcaaaat taacaaatct    4920
cttaacaaaa tatatctttt gccctctttta aagtcttcag taaaccagta aatgaattca    4980
ataaaccaat taagaaaaaa aaaaaa                                         5006

<210> SEQ ID NO 8
<211> LENGTH: 2288
<212> TYPE: DNA
<213> ORGANISM: Homo sapiens

<400> SEQUENCE: 8
gaagtggagg tgggagggag cgacaatgga aaaatcacct gaaaactggg acagaggaag      60
gaagctacag ttacgaagga gagctgcaaa agttgcagca gaaaggttgg gagtcccgac     120
aggttccgta gcccacagaa aagaagcaag ggacggcagg actgtttcac acttttctgc    180
ttctggaagg tgctggacaa aaacatgaaa ctaatttccc caacagtgat tataatcctg    240
ggttgccttg ctctgttctt actccttcag cggaagaatt tgcgtagacc cccgtgcatc    300
aagggctgga ttccttggat tggagttgga tttgagtttg ggaaagcccc tctagaattt    360
atagagaaag caagaatcaa gtatggacca atatttacag tctttgctat gggaaaccga    420
atgacctttg ttactgaaga agaaggaatt aatgtgtttc taaaatccaa aaaagtagat    480
```

```
tttgaactag cagtgcaaaa tatcgtttat cgtacagcat caattccaaa gaatgtcttt      540
ttagcactgc atgaaaaact ctatattatg ttgaaaggga aaatgggac tgtcaatctc      600 catcagttta ctgggcaact gactgaagaa ttacatgaac aactggagaa tttaggcact     660
catgggacaa tggacctgaa caacttagta agacatctcc tttatccagt cacagtgaat    720
atgctcttta ataaaagttt gttttccaca aacaagaaaa aaatcaagga gttccatcag    780
tattttcaag tttatgatga agattttgag tatgggtccc agttgccaga gtgtcttcta    840
agaaactggt caaaatccaa aaagtggttc ctggaactgt ttgagaaaaa cattccagat    900
ataaaagcat gtaaatctgc aaaagataat tccatgacat tattgcaagc tacgctggat    960
attgtagaga cggaaacaag taaggaaaac tcacccaatt atgggctctt actgctttgg   1020
gcttctctgt ctaatgctgt tcctgttgca ttttggacac ttgcatacgt cctttctcat   1080
cctgatatcc acaaggccat tatggaaggc atatcttctg tgtttggcaa agcaggcaaa   1140
gataagatta agtgtctga ggatgacctg gagaatctcc ttctaattaa atggtgtgtt    1200
ttggaaacca ttcgtttaaa agctcctggt gtcattacta gaaaagtggt gaagcctgtg   1260
gaaattttga attacatcat tccttctggt gacttgttga tgttgtctcc attttggctg   1320
catagaaatc caaagtatt tcctgagcct gaattgttca aacctgaacg ttggaaaaag   1380
gcaaatttag agaagcactc tttcttggac tgcttcatgg catttggaag cgggaagttc   1440
cagtgtcctg caaggtggtt tgctctgtta gaggttcaga tgtgtattat tttaatactt   1500
tataaatatg actgtagtct tctggaccca ttacccaaac agagttatct ccatttggtg   1560
ggtgtccccc agccggaagg gcaatgccga attgaatata acaaagaat atgacatctg   1620 tgggcctca caaggaccag ggccttctgg aggagtggca ctaccccacc tggcagcacc    1680
tagacctgag ctctacaaaa acacactgct tcactttgtt ttaggactta gttcaagaac    1740
acattcaaat ggtgcatgtg tttggtatct tcaacagtag accaagaatc taacatcact    1800
ctcagtaata tagagaccgg aatacatggt ttataggaaa tgatcaaatg atccaaaaaa    1860
actccacatt ttttaagaag ttggaatttg atttcatgca taactgtatt aaaacattaa    1920
atagaaataa tgtcatttga atgaaaatct tatcacatta aattcactgt gaaggcagca    1980
tacttaaatt tttattttga aaagtctaaa aggcttagat tttaaaatt taataattat    2040 ttctacaaat tttctattt tcttgaggtg attctcaact agcaattgga actcctaggc    2100
tctattaaca taattcttta ttgtaaacgt atctaatgct aaaagtaata aaatggtagt    2160
tttctgagac ctgtgaggac aggaatggtg tcttacattc atttctacac tttattatgc    2220
tcaggattgc accttcttta cagagtatat tcaataaatg tatgttgatt gaaaaaaaaa    2280
aaaaaaaa                                                             2288
```

<210> SEQ ID NO 9
<211> LENGTH: 7086
<212> TYPE: DNA
<213> ORGANISM: Homo sapiens

<400> SEQUENCE: 9

```
agcagcggcg gcagcggcag cccagccgag cgttaggtgc tgctctctgc gcggcgtttt     60
gcaaaggact tcaccgatct acttttgcag tcgcctcgga ctgtccatgt gtttacttcc    120
cccagcccga ggattcgata tctaggttcc tgtgaaatgc aactgagcag ccaaagtact    180
ttgagaacac ggggcggcat aaacaccaaa acttttttgt ggaaggaaaa tgcaataagc    240
```

-continued

```
aagcttgccg tttteegatg cggtgtggag tgagtgtgtg tegegegtgt cegcactgga    300 ggcatatget tgtgtgtgta catggggtgt gttttteggt atgtagggag aaaatgettg    360 ccaaccaccg gaaatetect ggaatttatt agaaaataat ggattataaa aagaaggcaa    420
gcaaggagcg gatctcccct tgagttgcaa cccgatttgc tgctggctca gtttgttgtg    480 attettttg ttgataggtg tctgatggta ttccgataac gttccccct tttcttcccc      540 ttgagctttt acagtttaaa aaaggaaac aaaaaccacc ccaaaatctc cccccccgtt     600
tttttcgccc cgtcgggatc gccgtttcca tccatgtgct tgcgtctccc ccgcgttcca    660
cttaaactat tttaatcctt ggacccaagg aggaggctga taggggggtg gataaaaaaa    720
gttcttccaa aatagtgtgc ccggggagca ggatggggga tttcgcagcc cccgctgctg    780
ccgcgaatgg cagtagtatt tgcatcaaca gtagcctgaa cagcagcctc ggcggggccg    840
ggatcggtgt gaataatact cccaatagta ctcccgctgc tccgagtagc aatcacccgg    900
cagccggtgg atgcggcggc tccggggcc ccggcggcgg ttcggcggcc gttcccaagc     960
acagcaccgt ggtggagcgg ctccgccagc gcatcgaggg ctgccgtcgg caccacgtca   1020
actgcgagaa caggtaccag caggctcagg tggagcagct ggagctggag cgccgggaca   1080
ccgtgagcct ctaccagcgg accctggagc agagggccaa gaaatcgggc gccggcaccg   1140
gcaaacagca gcacccgagc aaaccccagc aagatgcgga ggctgcctcg gcggagcaga   1200
ggaaccacac gctgatcatg ctacaagaga ctgtgaaaag gaagttggaa ggagctcgat   1260
caccacttaa tggagaccag cagaatggtg cttgtgatgg gaattttct ccgactagca    1320 aacgaattcg aaaggacatt tctgcgggga tggaagccat caacaatttg cccagtaaca   1380
tgccactgcc ttcagcttct cctcttcacc aacttgacct gaaaccttct ttgcccttgc   1440
agaacagtgg aactcacact cctgggcttc tagaagatct aagtaagaat ggtaggctcc   1500
ctgagattaa acttcctgtc aacggttgca gtgacctgga ggatagcttc accatcttgc   1560
agagcaaaga cctcaaacaa gaacctctcg atgaccctac ttgcatagac acatcagaaa   1620
catctctttc aaatcagaac aagctgttct cagacattaa tctgaatgat caggagtggc   1680
aagaattaat agatgaattg gccaacacgg ttcctgagga tgacatacag gacctgttca   1740
acgaagactt tgaagagaag aaggagccag aattctcgca gccagcaact gagacccctc   1800
tctcccagga gagtgcgagc gtgaagagcg accctctca ctctcccttc gcacatgtct     1860
ccatgggatc tccccaggcg aggccttctt cttctggtcc tccctttct actgtctcca     1920 cggccactag tttaccttct gttgccagca ctcccgcagc tccaaaccct gcaagctcac   1980
cagcaaactg tgctgtccag tcccctcaaa ctccaaacca agcccacact ccaggccaag   2040
ctccacctcg gcctggaaat ggttatctcc tgaatccggc agcagtgaca gtggccggtt   2100
cagcgtcagg gcctgtggct gtgcccagct ctgacatgtc tccagcagaa cagctcaaac   2160
agatggctgc acagcagcaa caaagggcca aactcatgca gcagaaacag caacagcaac   2220
agcagcagca gcagcagcag cagcagcagc agcagcagca gcaacagcag cactcaaatc   2280
agacttcaaa ttggtctccc ttaggacctc cctctagtcc atatggagca gcttttactg   2340
cagaaaaacc aaatagccca atgatgtacc cccaagcctt taacaaccaa acccctatag   2400
tgcctccaat ggcaaacaac ctgcagaaga caacaatgaa taactacctc cctcagaatc   2460
acatgaatat gatcaatcag cagccaaata acttgggtac aaaactcctta aacaaacagc   2520 acaatattct gacttatggc aacactaaac ccctgaccca cttcaatgca gacctgagtc   2580
agaggatgac accaccagtg gccaaccccca acaaaaaccc cttgatgccg tatatccagc   2640
```

```
agcagcaaca gcagcagcaa cagcaacagc agcagcagca gcagcagcag ccgccacctc   2700
cacagctcca ggcccccagg gcacacctga gcgaagacca gaaacgcctg cttctcatga   2760
agcagaaagg agtgatgaat cagcccatgg cttacgctgc acttccatcc cacggtcagg   2820
agcagcatcc agttggactt ccccgaacca caggccccat gcagtcctcc gtgccccag    2880 gctcaggtgg catggtctca ggagccagtc ccgcaggccc cggcttcctg ggcagccagc   2940
cccaagcagc catcatgaag cagatgctca ttgatcagcg ggcccagttg atagagcagc   3000
agaagcaaca gttcctgcgg gagcaaaggc agcagcagca gcagcagcag cagattttgg   3060
cggaacagca gttgcagcaa tcacatctac cccggcagca cctccagcca cagcggaatc   3120
catacccagt gcagcaggtc aatcagtttc aaggttctcc ccaggatata gcagccgtaa   3180
gaagccaagc agccctccag agcatgcgaa cgtcacggct gatggcacag aacgcaggca   3240
tgatgggaat aggaccctcc cagaaccctg ggacgatggc caccgcagct gcgcagtcgg   3300
agatgggact ggccccttat agcaccacgc ctaccagcca accaggaatg tacaatatga   3360
gcacaggcat gacccaaatg ttgcagcatc aaaccaaag tggcatgagc atcacacata    3420
accaagccca gggaccgagg caacctgcct ctgggcaggg ggttggaatg gtgagtggct   3480
ttggtcagag catgctggtg aactcagcca ttacccagca acatccacag atgaaagggc   3540
cagtaggcca ggccttgcct aggccccaag cccctccaag gctgcagagc cttatgggaa   3600
cagtccagca aggagcacaa agctggcaac agaggagctt gcagggcatg cctgggagga   3660
ctagtggaga attgggacca ttcaacaatg gcgccagcta ccctcttcaa gctgggcagc   3720
cgagactgac caagcagcac ttcccacagg gactgagcca gtcagtcgtg gatgctaaca   3780
cgggcacagt gaggaccctc aacccagctg ccatgggtcg gcagatgatg ccatcgctcc   3840
cggggcagca aggcaccagc caggcgaggc caatggtcat gtctggcctg agccagggag   3900
tcccaggcat gccagcgttc agccagcccc cagcacagca gcagataccc agtggcagct   3960
ttgctccaag cagccagagc caagcctatg agcggaatgc ccctcaggac gtgtcataca   4020
attacagtgg cgacggagct gggggttcct ccctggcct cccggacggt gcagaccttg    4080
tggactccat catcaaaggc gggccagggg acgagtggat gcaggagctt gatgaattgt   4140
ttggtaaccc ctaatcaaga gaggcccaa gatccacaac tcgagtggtt aaagcttaaa    4200
aagtgaaaaa gaaacaggat gttgacccat ccttgttttt tgttttttg acccacgtaa    4260 actgagcaaa actgcagctg gctgacaatg gaagatccag gtgccaatcc acagccccac   4320
caggcctcat ttcacctgat tttcacacag caatcgagat gagacgccat gcagatcccg   4380
gctgcgagag agggagacac ccggaggagc aggtgggaag atgaagccgg ccagagcccc   4440
tctgcccagc atgcctgtg atcgcctggc ccagcaggag ctgcttcagc cgagagggac    4500
tattacccaa gagaggtatc ctcagcccct cctgccccag gtcgggagac agcagctttg   4560
gagacacaaa agagacagag cctcagccag ggagagtgag tccccagaa gaggctgggt    4620 ggttgcacag gccaggtgca caggttggaa atgcactgaa ctctgggtgc cgagagatgt   4680
aaggctttga acatgctac tgaatttgga gggcaggcac gaagaacagt gagattgtca    4740
aaaggagaca accacagatc ctacaggact gtctgtctcc tgccccatga tgaccctcag   4800
gaattgcaaa ggctctgctg tcacaaggag agcaggctga gtttggagca gggtccatcc   4860
ggcagtcctg ggacggcttc cctctgctgg tgccctggt ggcagtccct ccaggtgggg    4920
ctggagcctg ctggcgccca atacaaaacc catacatcca ggtgggtcac atctacttct   4980
```

```
ggcggccgca gggcagggaa acccctactg gaccctgtgt gtctgccagc ctggagcctt    5040
tgtctccagc cctgccttta ttcctccttg cctccacacc agcctcccct tgcttctcct    5100
tacagactat ccaagaagtg aagcttatgt ctttagggag ccttgggcag agtccacata    5160
aatgcaggaa gaacttagac aatgcctgaa atgcaaaggc gacactggag tcttcttcct    5220
ctaacgtgta gcgttgaatg aatatctgcc tggaaccaag agggctgctc tgatgtttgg    5280
gagtcggttt tttgtgagcc acatctgata tttctgatat ccccaggaag gagtggcctg    5340
gaggtcactg gttcaggctc cctttgggcg aaatcctggg agtgatgctc taaaaatcca    5400
cctttcccat catccctact catcagaaag acaaatataa aatcccagag aggtggagga    5460
gctaaaaaag caattgctcc accttacaaa tttggataga aaggagatgt agtttatttc    5520
atatgggcaa agtagtcctc ttccaaagtc ctgtacagtt gttctctgca attgacgcac    5580
atctgcccta agcgaaatct gtcagaagga atcaacaagg ctccttgcct ccctcccaa     5640
tccccctttt ggaggacttg tggcttcggt gtcgtcctaa gtgagagtgg cgtgtgcttt    5700
tttcctgtcc cctcctccct ccgtgtccta gacgctggct gccttctgtg cactcccagg    5760
cagatcacta cggaagagtc ggagcctgtg gggttggact ggccacactc agtcctgaga    5820
aggcgagttg ccatggaaag ctgggggcag aggtgttttt ggagaggagg cggcaggcaa    5880
acattgcctt tgacttgctc tccgcgtacc cggggttgta gagctgctca ggaaggggca    5940
ggatgtaagg ccagaggtgc ctggtgggtg agaagcccag gcaggggctg ggcgccctct    6000
ccgaagaggt ggcagcaggg tgaccctgaa ctccccaaat ggggagtgat gccactgggg    6060
aaactgagtg gatcaaagag atgaaaccaa aaaaaagcaa acaaacaaat gagaagacac    6120
aaaacataat tacctttttcc tgaaaggtac aggaaataaa tatataagca atgatgagaa    6180
actggaggtg gctaatggaa gtgagacaga caggggtggg gggctccatt atcttttaaa    6240
agcttcctcc aaatgctcag tactgggacc aactaatagg tagattttaa tatggtggtt    6300
ttgttttggt tttgttttta ctacggtgct gatgtatatg taatgtctaa aaaaagttat    6360
ttgtacataa gttttacaa tactgcagat atcactgggt ctactatctg taaaaaatat     6420
acatataaat atatatatac tgtttgttta aaatagagta tttttatttc attccttaac    6480
tcatcatcac agcagtggta ttgcacttca gatgacatct aattactaat ttgtactgta    6540
tgacctctgg caacttgctc cattttattc agattttct agttttctgt ttttactttg     6600
tacattgagc attgcttatt cccttttaag aaatgtacag aacgctgaaa tgtagaaatg    6660
aagtgatgtt gacataccac ttttaaagaa aacaaaaaca aaaataaaag attatctgaa    6720
tcaatccaaa gtatagttta ttttaagatc ctcactggag ctccaatctt aattaagcag    6780
acatattatt cctgggtttt aattaactgc agttcttttc tcaaaatttt gatatcattc    6840
tttaaacatt tatttaatgg gagagatcaa tcattcccag cctttgcatt caactgcaca    6900
actgatgata ctttctgaat ttactgccgc actctgaagg atgtggcaaa gggaagggag    6960
gaaagtcaac tttgcatgga acatagtgca atccatttgt agattcagta ccataacaat    7020
tccatttcca actagttcat ctggaggtag ggaggctcca ctggaaaaat aaatatttt     7080
gtcaaa                                                                7086

<210> SEQ ID NO 10
<211> LENGTH: 9068
<212> TYPE: DNA
<213> ORGANISM: Homo sapiens

<400> SEQUENCE: 10
```

```
cggcgcgcgc gcggggcggg ggcgcgcgga gggggggggct gccccggggc ggccccccca      60
ggtcggggcg cggcggcgg cggcggcggg cgcgcgtccc gtccaggtcc ggagtaaccg       120
ccgccgccgc cgccaaagct cgccaacatg gcggacctgg aggctgtgct ggccgatgtc     180
agttacctga tggccatgga gaagagcaag gcgaccccgg ccgcccgcgc cagcaagagg     240
atcgtcctgc cggagcccag tatccggagt gtgatgcaga agtaccttgc agagagaaat    300
gaaataacct tgacaagat tttcaatcag aaaattggtt tcttgctatt taaagatttt    360
tgtttgaatg aaattaatga agctgtacct caggtgaagt tttatgaaga gataaggaaa   420
tatgaaaaac ttgataatga ggaagaccgc ctttgcagaa gtcgacaaat ttatgatgcc    480
tacatcatga aggaacttct ttcctgttca catcctttct caaagcaagc tgtagaacac    540
gtacaaagtc atttatccaa gaaacaagtg acatcaactc tttttcagcc atacatagaa    600
gaaatttgtg aaagccttcg aggtgacatt tttcaaaaat ttatggaaag tgacaagttc    660
actagatttt gtcagtggaa aaacgttgaa ttaaatatcc atttgaccat gaatgagttc    720
agtgtgcata ggattattgg acgaggagga ttcggggaag tttatggttg caggaaagca    780
gacactggaa aaatgtatgc aatgaaatgc ttagataaga gaggatcaa aatgaaacaa    840
ggagaaacat tagccttaaa tgaaagaatc atgttgtctc ttgtcagcac aggagactgt    900
cctttcattg tatgtatgac ctatgccttc cataccccag ataaactctg cttcatcctg    960
gatctgatga acggggcga tttgcactac acctttcac aacacggtgt gttctctgag     1020
aaggagatgc ggttttatgc cactgaaatc attctgggtc tggaacacat gcacaatcgg   1080
tttgttgtct acagagattt gaagccagca atattctct tggatgaaca tggacacgca    1140
agaatatcag atcttggtct tgcctgcgat ttttccaaaa agaagcctca tgcgagtgtt   1200
ggcacccatg gtacatggc tcccgaggtg ctgcagaagg ggacggccta tgacagcagt   1260
gccgactggt tctccctggg ctgcatgctt ttcaaacttc tgagaggtca cagccctttc    1320
agacaacata aaaccaaaga caagcatgaa attgaccgaa tgacactcac cgtgaatgtg    1380
gaacttccag acaccttctc tcctgaactg aagtcccttt tggagggctt gcttcagcga   1440
gacgttagca agcggctggg ctgtcacgga ggcggctcac aggaagtaaa agagcacagc   1500
tttttcaaag gtgttgactg gcagcatgtc tacttacaaa agtacccacc cccttgatt    1560
cctccccggg gagaagtcaa tgctgctgat gcctttgata ttggctcatt tgatgaagag   1620
gataccaaag ggattaagct acttgattgc gaccaagaac tctacaagaa cttcccttg    1680
gtcatctctg aacgctggca gcaagaagta acggaaacag tttatgaagc agtaaatgca    1740
gacacagata aaatcgaggc caggaagaga gctaaaaata gcaacttgg ccacgaagaa    1800
gattacgctc tggggaagga ctgtattatg cacgggtaca tgctgaaact gggaaaccca    1860
tttctgactc agtggcagcg tcgctatttt tacctctttc caaatagact tgaatggaga    1920
ggagagggag agtcccggca aaatttactg acaatggaac agattctctc tgtgaaagaa   1980
actcaaatta aagacaaaaa atgcatttg ttcagaataa aaggagggaa acaatttgtc   2040
ttgcaatgtg agagtgatcc agagtttgtg cagtggaaga aagagttgaa cgaaaccttc   2100
aaggaggccc agcggctatt gcgtcgtgcc ccgaagttcc tcaacaaacc tcggtcaggt    2160
actgtggagc tcccaaagcc atccctctgt cacagaaaca gcaacggcct ctagcaccca   2220
gaaacaggga gggtcctcga ggaggacaca ccagggtctc agccttttgg ggtgaacgag    2280
gatgaggcat ctgatctatt cgctaccggg actcctccag gctcccgaga ggagtcggga   2340
```

```
cccttcggct tggggtcagc tcagctccct gccttgtcac atttgtctgc attagaaact    2400
actgaagaaa taaaagttct ttttctttgc tacacacttt ggtacctatg aacctagaac    2460
ttgaagtgac tcctacttat cacgtaaatt tttatgtctg atatcaaaca catcttagac    2520
tccccagaat ggaatttaaa gatgttcagt gttgggtaac agattgccct aagcattgcc    2580
acatattctg tctagtcact gctgattttc tatgtctttg ctccatactg ctgggggatg    2640
ggagagccac agtgtgtttc ttttgtgcac ttcgcaactg acttcttgtc ctggggttaa    2700
aagttgaaga tattttctga tgatattaaa agttgaagat atttctgcac ttgggccctc    2760
ctctgggagc cgcacccaca tgactgccct gcctctgacc agtctgttcc ggggccccct    2820
cagccaggtg ggaatgacgg acacgtacta tccaagtgta tgggattaac taatcattga    2880
aggcattcat ccgtccatca ttggaaagat ttacagtgat tctgaaggac aggccgtgga    2940
gttttaggtt tcagggcaa gagcagtttt caaaagtctt tgagtccagt gtgcacgagt     3000
cgacaagcag tacctggcat gcaggagcac tcatgggtga gtccgtctca ggtctcgaca    3060
attagcagtt gtgtgacagt cattctggtt ccttctgcct gaccctggga gacatatcag    3120
taatggatgt acaaaagcag gtctgtttta tgtcttagta taatttcaga tgaattgtat    3180
tgaaaaaatg ctgaggaatg aatgtgtcaa atgggttaa ctgtgtatat tgactttcat     3240
gtcgtcatgc atctgtcatg aatgaatgat actttgcact gggctgtacg acagtgagga    3300
ccttagggca tgaagccttt ttcctggtcc cagcagcatc tgccctgtga gtttgttttt    3360
ctcccactgc ctccaggccc cactgatacc cccaaataga tgctgggtta tgagaaccag    3420
cgaaatcccc catgtcatca gtcttaaaaa aaaaatttta caaatccacg tatttgtccc    3480
attcttggag tagttttagt gtatgtcttt acattaacta ctaacagtat aaataacttg    3540
acatcgtaat tgtctgcatc ctgtccttga tattttagc agttccaaat ctttgttttt     3600
gtatttgttt gctgtgttca tgggcaaagt aagtactttt taatgcagtt attttgagag    3660
tttggaagat aattaccaaa agggtccatt atttcataag agttactttg caaaaaaaaa    3720
aatgtgggtt ttttttttg tctatctcaa ctactagttg gggtttaaat taacatacat     3780
tttctactat ctgttatttc cagtgtggga ggagggatgt actacttaca tgcattctcc    3840
ttatttaaaa aggaagaata gtattcaaat tctgttgaaa cacacacaca cacacacaca    3900
cacacacaca cacactccag aagcagaaaa gccattgttc ttaaagagtg aatgtcttcc    3960
cagccctggt taattatagc tgtgactgat gccgttcccg tctgcatctc aagctcatag    4020
gttctcagca tgtgcagttg aggatgcgct gggcctcatg cctgttctag atctccagga    4080
taaagggcct gctgttgact ccaccagggt ctgggcttag cgtctaatat ctcgtaccta    4140
gggcgtgagc tgcacaaacg tgttcagaaa gattattcaa cttttcccata cttgttctaa   4200 aattgagctg atccgcatct ctttcaaaaa ctagaatttc tgctctaaga atagaacata    4260
aggctccact cccttttaga aaagatatat gaattggaaa atgctctgaa agtccttttg    4320
cttcaaacaa aagtgtaaac ttttacactt ccccaactca catttgattt gtaatgatat    4380
ggttgagaag tacatctaga tgtcatttat taaaagtgct ttgtaagact agattgagct    4440
gtttctgagg gcggtcacca gttgtgttgg ggtctggttt gagtgccttc tgccaaaatg    4500
ttgtgatgga ggtgtttctg cgaccagaca caggataccg ctgtgtctgc acccggttgc    4560
ctgcatggcc agaggaaaag tcagttggat taaacatcat ggtatacttg gctgttgttt    4620 tttttaatt ttttaatttt ttgggatagg gcctcgctct gtcacccagg ctggagaaca     4680
gtgggatgat catggctcac tgcagccttg aattcctagg ttcaagcaat cctcccacgt    4740
```

```
cagcctcctg agtagctagg actacaggtg catgccacct ttcctggcta atttattttt    4800
tgggtagaga tggggtcttg aactcttagg ctcaagtgat cctccttcct tggcctccca    4860
aaatgctgga attagagatg taagccacca tgcccagcca tagtacttgg atgttttaga    4920
aggttttcca agtattacat aattcctaga tgttcaccct tattacactc caactattaa    4980
aaaggtcaaa attcagccta ttttttttca ttattttaga ttcctgtggt tgggatattt    5040
taacattgat gagaaaaata attgaggttg atattttttac aaaatcatgc ggtaataagt    5100
cttgatttca tgattcaaaa gaatcaataa agcctaaaaa taatagatta ctttaagctg    5160
ctatgtaaga tatatatgga ataaattaaa aacctttgtg aattcaggtt tattatttt     5220 aacctaaaac attctctttg gttcattcat cccctcatgt catgggggct cattggtttt    5280
ccttctttgt catatttaag tatgattttt caacaaaact tctagaagtc agcttattat    5340
gtcaccattc atgcaaagtg ctcatgcctc tgattggtcc attcactgac gtgacaattt    5400
caggtcctat gtttaaaaag aaggggctgg ccgggcacga tggctcacgc ctataatccc    5460
agcactttgg gaggccgaga ggggcggttc acgaggtcag gagattgaga ccatcctggt    5520
tagcagagtg aaaccccgtc tctactaaaa atacaaataa aaattagccg ggcgtggtgg    5580
cgggcgcctg tagtcccagc tacttgggag gctgaggcag gagaatggca tgaacccggg    5640
aggcagagct tgcagtgagc cgagattgcg ccactgcact ccagcctggg cgacagagcg    5700
agactctgtc tcaaaaaaaa aaaggagggg ggctaaatat ccagtgagat gcactgagga    5760
aaggaagcat tttgctgaag acagcagcag caacaaacaa tggtctgttt gttgcaaaca    5820
agatgtagct tgatttctgg tctgacatat gccatataca gatattagaa acgactgttt    5880
gaaggccaca ctggtcatct acaaagtaat gtttaccaat tgacgacagg gatttaacta    5940
gattaaaaag atcaaagtgt ggttttctc tgcttttaa aatttcactc ggaatttgta     6000
gctgggccaa ttcaacacat tttacttttc agtggaattg attttttctaa tgtttcagaa    6060 ttttaacata tcaagaagaa aacaacgttc tcaaagtctg gcctctttag catgatgtaa    6120
acctatagaa atgctttgaa atgtgctggt gtaagataag agttatcttg tatgatttaa    6180
tcatatgcag tgttgtctca gttacgttca gggaaatgtt tctgtgtcat tcagagatgc    6240
ttgatgaatt aacacctccc accctgagtg aggggttgac ttgttgggag atgatttggg    6300
cttcactggg atctgtgaca ggtggggct gggctgggtg tcacaaagag aatagtggta    6360
gaaatcgggc gaaggaagaa agaagttact ggtaaaaatc attacaccat aaagcaccaa    6420
ggaaataact gagttaaaat aggtgaagtt tcttttttcc cccctgtaac aggagagttt    6480
tccttatgat aattattctg agacttggtc actttgtttt tgaatgtgga gctgctgaac    6540
tcattcagaa gccatttgct gcctatcagg actttctgaa gaagttcttt tgcctctgcc    6600
taccctctgg caccctccca tggaggcaca ggggacccag agctaaagca ttaccaggcc    6660
atctccaaaa caccccgtgt gtgtgtgtgt gtgtgtgtgt gtgtgtgtgt gtgtgtgtgt    6720
gcactttgca gcccccgagg tggagaggca gtgtctggat cactgtgaat gcattgcccc    6780
attggtcagt tggggacact gttacaaatc cactgaagtc ctggtaaaac tgtcaagagt    6840
aacaggcctc ttctgttcta ccctgctcac ttccacggtg agttaccagc ctgggcaaca    6900
cagcaagacc ccatctctac aaaaaaaatt ttttaagta attaaccgtt taaatttttt    6960
cctaaagatt taacatgatt tttccctcct atgtaaagtt tactgagagag acttgaatta    7020 cttaaattca tgttaatatg attttttttt aatccaggtc acattttaac aaagtttatt    7080
```

```
atgaaacaaa tgaaatttga actctaaaat ggtactcctt ggcttcctca agtcacaatg      7140
aactttatat tttctttgtc cttaaggact aagatagttg ttttatttca gccgaatcac      7200
agagataacc actcctgcag gcccccacag ctggcccaaa ggggctgtct ttctgacctg      7260
gctgtgttag cactgattga gaaacgcagg ctcccaaatt ttaaattgcc tttattaaaa      7320
acacaaacta cagaaaatgg gttaagagta tacgcatttc atcaaacaca tatagggaa       7380
aaaatccttc aatttagagt taaataactc agctttgtat agtagagtta gcgctccagt      7440
atctaacaat ctcagaatca tctctgaaaa ctggtaacta tgcttccatt tttaattttg      7500
tcctaaatat cagatgtctt tgatgtaagg gtagggaatg gagaaatatt tcaattgtg       7560
tatttgtatt acaaagaact tgaaatttac tttcttagtt gattatatta aatgatgtat      7620
atattatatg tggtttataa gctcaacact ggccatttt ttagttttat tgttaaatgg       7680
tattttctcta tgtttaatta aatagatct ggcttttct ggatagcata aagatcactg       7740
aactatatat ataagaaa caagagttct attttagcac aaaggcattt tatattattt       7800
attgaatcca taagtttgtt ttcgtcaaaa acattccata ttatttctgc tccttttat       7860
ttgtatagtt tgttatttaa agaaatggca gtccttcctg ttcttaatac aataaaattg      7920
aaataatgca cctagtaatg tggccgacat ctcttctcac caccatggac tgttttcaac      7980
aacagttgat cttctggtct gtgctgagag gcgcatgcat gtctttcgtc acgtcgggca      8040
gcacacctgc tgtgaaatac tgctttcatc tacctcttca gaaggcttct tgcttgttga      8100
caagtaccgc aaaggcttta ttctggactg gctatctcat aaaaggatt ctgtaagact       8160
ttgcagtgtc attccctcag aacctaggtt tgtttctaaa gccacggtat tgtccaggag      8220
cccctgtgtg tggggcaggt agctatccct cccatgtcat tagtaatcct ttaggattta     8280
aggtacaact ggacagcatc attccttccc cttattgtgc caaatcccca ccatcagcct     8340
tgccattgcc ttaagatttg attattgcac ccaattacct aaccactaaa cagaaaggcc      8400
accttcactc tttgaaaaag gcaagctgtg cttagaaaca ctgcttttaa gagtagcaca      8460
tttgagtgtg actttttccc cccttcacta tttcaaaatg gttttgaaat ggggtcttaa      8520
aggtaagcgc cctcatacat gactgaaact ttgtgagagg tcttatattt gaatggaccc      8580
ttaatgattt atgtgaaata gaatgaagtc ctgtctctgt gagagaacgt gcctcctcac      8640
tcatttgtct ctgtctgttt tcatagccat caatatagta acatatttac tatattcttg      8700
aataccctg aagaaagaaa tccgttttct attgtgcatt gctatacgaa gtgaagccag       8760
taaactagat actgtaaatc tagatattgt acctagacaa aatatcattg gttctatctc      8820
tttttgtatc tgttgtgcca gggaaggttt ataatcctt ctcagtatac actcactagt       8880
gcacgtctga aatagtatcc cacggggagat gctgctccac gtctgaggtc acctgccctg     8940
tgtgggcac accaccgtca gcaccaccgt ttttacagtt actttggagc tgctagactg      9000
gttttctgtg ttggtaaatt gcctatataa atctgaataa aaaggatctg tacaaaaaaa      9060
aaaaaaaa                                                              9068
```

<210> SEQ ID NO 11
<211> LENGTH: 5069
<212> TYPE: DNA
<213> ORGANISM: Homo sapiens

<400> SEQUENCE: 11

```
aaaaagggt gaggagaagc agcggctgag cgggttggca tctggggcag cgggctcgct        60
ccaggccgtc gggggccgct cgccagcgtc gcccgctgtg ttgggagcgc gggccgtggg      120
```

```
cgtcgctcgg ccttgtccgc ggcgtccccg ctgccggcca cggcgctcag cgcttgtgct    180
ctgtattgca ggtctacccc gagccccgga gcgagagcga gtgcctgagc aacatccgcg    240
agttcctgcg cggctgcggg gcttccctgc ggctggagac gtttgatgca aatgatttgt    300
atcaggggca gaattttaac aaggtcctca gttccttagt gactctaaat aaagtaacag    360
cagacatcgg gctggggagt gactccgtgt gtgcccggcc ctcgtctcac cgcataaagt    420
cttttgactc ccttggatca cagtctttgc acactcggac ttcaaaactg ttccagggcc    480
agtatcggag tttggacatg accgataata gcaacaatca actggtagta agagcaaagt    540
ttaacttcca gcagaccaat gaggacgagc tttccttctc aaaaggagac gtcatccatg    600
tcacccgtgt ggaagaggga ggctggtggg agggcacact caacggccgg accggctggt    660
tccccagcaa ctacgtgcgc gaggtcaagg ccagcgagaa gcctgtgtct cccaaatcag    720
gaacactgaa gagccctccc aaaggatttg atacgactgc cataaacaaa agctattaca    780
atgtggtgct acagaatatt ttagaaacag aaaatgaata ttctaaagaa cttcagactg    840
tgctttcaac gtacctacgg ccattgcaga ccagtgagaa gttaagttca gcaaacattt    900
catatttaat gggaaatcta gaagaaatat gttctttcca gcaaatgctc gtacagtctt    960
tagaagaatg caccaagttg cccgaagctc agcagagagt cggaggctgc ttttttaaacc   1020 tgatgccaca gatgaaaacc ctgtacctca cgtattgtgc caatcaccct tctgcagtga   1080
atgtcctcac ggaacacagt gaggagttgg gggagttcat ggagaccaaa ggtgccagca   1140
gccctgggat tctcgtgctg accacgggcc tgagcaaacc cttcatgcgc ctggataaat   1200
accctacgct gctcaaagag ctcgagagac acatggagga ttatcataca gatagacaag   1260
atattcaaaa atccatggct gccttcaaaa acctttcagc ccaatgtcaa gaagtccgga   1320
agaggaaaga gcttgagctg cagatcctga cggaagccat ccggaactgg gagggcgatg   1380 acattaaaaac tctgggcaac gtcacttaca tgtcccaggt cctgattcag tgtgccggaa   1440
gtgaggaaaa gaatgaaaga tatcttctac tcttcccaaa tgttttgcta atgttgtctg   1500
ccagtcctag gatgagtggc tttatctatc agggaaagct tccaacgaca ggaatgacaa   1560
tcacaaagct tgaggacagt gaaaatcata gaaatgcatt tgaaatatca gggagcatga   1620
ttgagcggat attagtgtcg tgcaacaacc agcaggatct gcaggaatgg gtggagcacc   1680
tacagaagca aacgaaggtc acgtctgtgg gaaaccccac cataaagcct cattcagtgc   1740
catctcatac cctcccctcc cacccggtca ctccgtccag caagcacgca gacagcaagc   1800
ccgcgccgct gacgccgcc taccacacgc tgccccaccc ctcccaccac ggcaccccgc   1860
acaccaccat caactgggga ccctggagc ctccgaaaac acccaagccc tggagcctga   1920
gctgcctgcg gcccgcgcct cccctccggc cctcagctgc tctctgctac aaggaggatc   1980
ttagtaagag ccctaagacc atgaaaaagc tgctgcccaa gcgcaaacct gaacggaagc   2040
cttcagatga ggagttcgcg tcccggaaaa gcacagctgc tttggaagaa gatgctcaga   2100
ttctgaaagt cattgaagct tactgcacca gcgccaaaac aaggcaaaca ctcaattcaa   2160
gttcacgcaa agaatctgct ccacaagttt tgcttccaga agaagagaaa attatagtgg   2220
aagaaactaa agtaatggt cagacagtga tagaagaaaa gagtcttgtg gataccgtat   2280
atgcattaaa ggatgaagtt caagaattaa gacaggacaa caaaaagatg aagaaatctc   2340
tagaggaaga acagagagcc cgcaaagacc tggagaagct ggtgaggaaa gtcctgaaga   2400
acatgaatga tcctgcctgg gatgagacca atctataagg gatgtcctca gttctttctg   2460
```

```
ttgaagacca gttctgaggt gaagctgggc acccctgacc caagtcgggg tgcactcagg    2520
accacagggc agggctgggt ggggcgccac cttgctctct gtatatagaa aagctggagc    2580
ttattctgcg aatggagacg atcaaaccat gactgatgaa tccagacagg agggattgac    2640
tctgaggacc tgagctacat caatccactc tgtgaacatc tcagttacct cattctgcaa    2700
taagttcagt gactgactaa aagtcttgtt tttccagact ttgaattgaa tatataaata    2760
ttatatatac atgtttcttg taaatatccc attttgaatg catacctgtg gtggttctgt    2820
ccgggctaat ccccatgcta gaatgtcctt tccagctacg tgaataagaa gtcccatgcc    2880
cgcatccacc ggaagcagaa gcctggtgga tgcctggttc gttccgcagc accagggcct    2940
ccaccgtgct gtggcagcac cccccatgtc ggtatttcta ataaccctta tttatacctg    3000
cagagataca cttcagtccc attcagaagt cttctcttaa agcagcatta cagtcccaga    3060
cctgcgggtt tctgagggca acttgctggc tgacagactc agtcttgacc tcaaggaagg    3120
cccatacggc actgccgcat ccacctagag gtgtttgctc ttgtccgctg tctgagtact    3180
gtgattctca gatgagtttg ctgcgttttg ggaggacaca gacggttctg tataggctag    3240
ttcagtaaca acaaaataca ctgttttgtc ttccctcaaa gagagatctt actagaacct    3300
gtaaatagaa tgtattattt attataagtc actgcagctg atgaaaacag atggaggcca    3360
tgctgcaggc tgatactgat gggtggagtt ttgtcatcag gccagcctca tcccgaggtc    3420
tcctccacca ttggccgtag ccagcaggct tcagtgctca ccgaaagtaa aatcccctcc    3480
ttcagcaaga ataaagcaat atacacctta ggttccacta agtaacatag gcataagcag    3540
ggaacgtttc ccccactgtg ttccagtgca gaggagacga agcctgtcct caccgcggct    3600
cgctgggccc aggctggctc tggaaagcct gtgcggtcct gggcaggaag cccggcccgt    3660
ggagcaggtt ttcgttctgc ttcagcaata aataagggtg accacaggga ctttgctttt    3720
ggtttccttt cctgtgaaaa ggttggtttt aaagtgagat acacttttcc gtagaacaag    3780
tgttctatct ttaaaaaccc aaattgcagc accgtggatt actggtctca gaacaactca    3840
ttgcgcatca gatttgactc tctgattttc tgtctattgg ccaaattgcc ctttaactgc    3900
acctgaatcc tttgtgtact gatgcctttg agctgggcac cttgggagag tgttgtgttg    3960
ctgtttacgg ttcttccttg cccttgctaa ttacagtctc tggtgcccag caagcccctt    4020
tggcttcctt ccgtgactgg tcacgttgtc tgcctgggct cagcgtggac ctgccccatg    4080
ctgcagaacc tggcctcacc tggacttttc actagaattg ccagcttcct caacttagca    4140
gatcattcac tcatgcgggc acaagcaaag atcaacactt tcttttttgg taagcttgag    4200
ttttacaagt tattttttgg tgatgcgtaa gacattgcag tgggaaacca ttcaacttga    4260
gtttattgga gtttgctgtt gtagcaggtt ttaactcagg aacaactctt gtctgatctc    4320
tccgcccctc tgccgggagg cgacattaac tgtcctctcg gagccggtag cgttgctgtc    4380
cgagtcccca ggacggatct cctgcagacc tgccttaatg ctcagatcga agtatttcac    4440
aagaatactt gtgtttttaa cagcccttcc cctggacggt gcggccatga gggcctcatg    4500
ttacggcatt gccttttctt tctgtggatc cagtatcttc ctcggctttt tagggagcag    4560
gaaaaatgcg tctgagagca actcttttta aaaacctgcc ctgttgtata taactgtgtc    4620
tgtttcaccg tgtgacctcc caaggggtg ggaacttgat ataaacgttt aaggggcca    4680 cgatttgccc gagggttact cctttgctct caccttgtat ggatgaggag atgaagccat    4740
ttcttatcct gtagatgtga agcactttca gttttcagcg atgttggaat gtagcatcag    4800
aagctcgttc cttcacactc agtggcgtct gtgcttgtcc acatgcgctg ggcgtctggg    4860
```

```
accttgaatg cctgccctgg ttgtgtggac tccttaatgc caatcatttc ttcacttctc    4920
tgggacaccc agggcgcctg ttgacaagtg tggagaaact cctaatttaa atgtcacaga    4980
caatgtccta gtgttgacta ctacaatgtt gatgctacac tgttgtaatt attaaactga    5040
ttatttttct tatgtcacaa aaaaaaaaa                                      5069

<210> SEQ ID NO 12
<211> LENGTH: 81
<212> TYPE: DNA
<213> ORGANISM: Homo sapiens

<400> SEQUENCE: 12
aacacagtgg gcactcaata atgtctgtt gaattgaaat gcgttacatt caacgggtat     60
ttattgagca cccactctgt g                                              81

<210> SEQ ID NO 13
<211> LENGTH: 1251
<212> TYPE: DNA
<213> ORGANISM: Homo sapiens

<400> SEQUENCE: 13
agttgtaaac ccaaggccaa gagaccatgg ccacgttagc ccggctgcaa gctaggtcgt     60
cgactgtagg aaatcagtac tactttagga acagtgttgt agatccattt agaaaaaagg    120
agaatgatgc agcagttaaa atccaaagct ggtttcgagg atgtcaagtt cgggcatata    180
tcaggcattt aaacaggatt gtaacaatta ttcaaaaatg gtggagaagt ttcttaggca    240
gaaagcaata tcaactaact gtgcaggtag catattatac tatgatgatg aatctctaca    300
atgcaatggc tgtcaggatt cagagacgat ggcgaggcta tagggttcgg aagtaccttct   360 ttaattatta ttatttgaaa gagtacctga aagtcgtttc agagaccaat gatgcaatta    420
ggaaggcact ggaggagttt gcagaaatga agaaagaga agagaagaag ctaaccctcg     480
aaagggaaga gaagaaaaga gattaccaag cccgaaagat gcattacctc ctcagcacaa    540
agcagattcc aggaatatac aattcaccct tcagaaaaga gcctgatcca tgggagctgc    600
aattacaaaa ggcaaagcct ttaacacacc gaagacctaa agttaagcag aaggactcca    660
ccagccttac tgattggcta gcttgtacaa gcgcccgttc ttttcctcgg tctgaaattc    720
taccacctat taatagaaag caatgtcagg ggcccttccg agatatcacc gaagtattag    780
aacaacgcta caggcctttg gagccaacgt tgcgggtggc agaaccaatc gatgagttaa    840
agttggccag agaggagctc agaagagagg aatggctgca aatgtaaat gacaatatgt     900 ttttgccatt ttcttcatac cataaaaatg aaaagtacat cccatcaatg catttatcaa    960
gcaagtatgg tcctatttct tacaaagaac aattccgaag tgaaaatcct aagaaatgga    1020
tctgtgacaa ggatttccag actgtattac catcatttga gctcttctca agtatggaa    1080 aattatattc aaaagctgga cagattgtat aaaggcgtca gaagaagaaa ctgaagccat    1140
ctgcatttta aaacttaaca gttctgaaag gaaaacacag atgaagatcc tgtaggaaat    1200
atacttgcta tgattcaata aactataaaa ttttgaaaaa aaaaaaaaa a              1251

<210> SEQ ID NO 14
<211> LENGTH: 7996
<212> TYPE: DNA
<213> ORGANISM: Homo sapiens

<400> SEQUENCE: 14
```

```
gcgacccgag gaggcggaag agcggcgccg gcgacgtact gtaagacgat attactttaa    60
tcatcttcac atcagtattt atggaatagc cacaggtgcc tcatcctttta gtaggagtta  120 attatacatt tactggccga gtaaacatct ccgaatgtca ctccatggat tcctttgggc  180
aacccagacc agaagataat cagtcagtag tcagaagaat gcaaagaaa tactggaaaa    240 ctaaacaggt ctttatcaaa gcaacaggaa aaaagagga tgagcacttg gtggcgtctg    300
atgctgaact ggatgctaaa cttgaggttt tcactctgt tcaagagaca tgcactgaac    360
ttctgaagat aatcgagaaa taccagctaa gactcaatgt tatatcagag aagaaaatg    420 agctagggct cttttttaaaa tttcaagcag aacgggatgc aactcaagct ggcaaaatga   480
tggatgccac tggcaaggca ctttgttctt cagccaagca aagattggcc ctgtgtactc   540
ctctgtctcg tctgaagcaa gaagtagcaa cattcagtca aagggcagta tctgatacct   600
tgatgacaat taatcggatg gagcaggcac gcacagaata cagaggagct ctactgtgga   660
tgaaagatgt atcccaagag ctggaccag acaccttaaa gcaaatggaa agtttagaa    720 aagtacagat gcaagtgaga aatagcaaag cttcttttga caagttaaag atggatgttt   780
gtcagaaagt ggatttactt ggagctagtc gctgcaatat gctatctcat tcgctcacta   840
cctaccagag aacactgctt ggattctgga agaaaacagc tcgaatgatg tcccaaattc   900
atgaagcctg tattggcttt catccgtatg attttgtagc tctcaagcaa ctacaagaca   960
cgccaagcaa gattagtgaa gacaataaag atgaacaaat aggcggtttt cttactgaac  1020
agctcaataa gctagttttg tctgatgagg aagcaagctt tgagagtgaa caagcaaaca  1080
aagatcacaa tgaaaaacat tctcaaatga gagaatttgg agcacctcag ttttctaact  1140
ctgaaaatgt tgcaaaagat ctacctgtag attcattgga aggagaagat tttgagaagg  1200
aattctcatt tctgaacaac ctcctaagtt ctggttcttc aagtactagt gaatttaccc  1260
aagaatgcca gactgccttt gggagcccca gtgccagtct cacatcccag gagccttcca  1320
tggggtctga gcccctcgct cattcttctc gattccttcc ttcacaactc tttgaccttg  1380
gctttcatgt ggctggagcg ttcaacaact gggtctccca agaggaatca gaactttgtc  1440
tttcacacac tgataaccag ccagtgcctt cacagagtcc aaagaaatta acaagatccc  1500
ccaacaatgg caaccaagac atgtcagcct ggttcaatct gtttgcagac ttggatccac  1560
tttcaaaccc agatgctatt ggacactcag atgatgaact tcttaatgct tgactgaagt  1620
tataatgtca cttcagtggc cttgagacat caattttgca acgtatttcc ttcgtggaaa  1680
ggatttagat tgtaacccgc acacaaaagc acggtgtttg tgaatataac acctgtcagc  1740
caactttaga cagatggtaa agaccacatt tgaataagta cacatctttc atatcttgga  1800
tttgcagctg ttggtactat gtggaaaata ttagaaactt ctatgtggaa atattagaa    1860 actacagagt ttgcgatatt tagatactga aatttatgtc aaaataacgg ctaggaataa   1920
ttctgtcaat atggagttga gcttatttct ttggaaaccc ttttaagttg ccttgctggc   1980
tgtgagaatt ttatatgtgg ataacaaaga tagatagata gcatgtaaat tgggttgtgg   2040
tttggggtca gttttttaaat gaaatagtag cgaggaggat tttctgtttt ggaaaacacc  2100
attagaacca gaccagcttt gttttgggtt agagagagta agatttgaga actcagtttg   2160
ctttaatgaa atcacagaga aacttggtac ttgttttttct tcatttggag gctaaaatgt   2220 aatgttttttt cattcataca aaataatgga cactccctaa ttccattatt aaatcttgaa  2280
ggggaagtag caggataatt aatttgctaa gcccatcctc tgcagaaaca gaaaaatcta   2340
tcttcccatc tcctaaaact cagaatgcac agtaatactt aaggcttgta caagtgtctt   2400
```

```
cagacccact ttttcataca cttgctatat agtagtatgc agtatttata ttattcctga    2460
aaataaaatg aggggagaat attccctaag caactggcaa tagtattcct gaaataccta    2520
gaaatttcta tctgaatgag ggagacactt atgaacacct tatccttaca tatatttgca    2580
tacttatctc atattttgtg acataattat ttaacccaga atactttctg gcagacatac    2640
agaaagctct gtgtgatcaa taagggagtg tctcattttt ctacttccct ctttctgtgg    2700
gtgacatgat ctgaggttct atttgattac taagcaaaat ctgttacccc tacagggttt    2760
agaacctaag tattagagag aaggctatt taatggaagt tagtgtaagc tgataaaaac    2820
gtagctaccg tacacacaca tcaatcactc aatttcctgt ccttttaaat tgcccaccct    2880
ttaattttga agcaatttcc caagtgtgtg tttgttttat atttgtcatc cagtccattg    2940
catttccata agaagacatt ttgactggct gggtgcggtg gctcacgctt gtaatcccag    3000
cactttggga ggctgaggca ggcggatcac gaggtcagga gatggagacc atcctggcta    3060
acatggtgaa accccgtctc tactaaaaat acaaaaaatt agccaggcgt ggtggcacgt    3120
gcctgtagtc ccagctactc cggaggctga ggcaggagaa tggcgtgaac ccgggaggcg    3180
gagcttgcag tgagctgaga tggcgccact gcactccagc ctaggcaaca gagcaagact    3240
ccgtctcaaa aaaaaaaaa aaaaaaaag acattttaac taagttattc acagtagctt    3300
ccatgtgctc ttagttctat tctaaacagg cttatttaga aaaggattgc ttgtaatgtt    3360
tgtcatggta catagaaaac attggaccag agtaggtaaa atgcagtcca tgtcccatcc    3420
atagccatct acaatagtaa ctgcccacag gctctccaga aaactactac aatggccaag    3480
tacagtatag gctggaaaga ccttatctga aggtcagaaa cattgactca gaaaaaaggt    3540
atgaagtctt tccataaaat cttttcacaa tattactcct atttcttta gattttaatg     3600 agccattact tatctcttca gaagacttaa gtcttccttt atactcagtg aaatttccca    3660
gaatgtaata ctgtcactgt tctgccaagt tccaatcacc aagatcatga ttacgaatcc    3720
caatctgaat tctataccca tggtgactct gatgctctca acttttgagt gcctcaaaaa    3780
atgctaaaac tttggctggg catggtggct cacgcctgta atcccagcac tttgggaggc    3840
catggcgggt ggaacatttg agggcatgag ttcgagacca gcctggccaa catggtgaaa    3900
ccctgtctct actaaaaata caaaaattag ccaggtgtgg aggtacatgc ctgtaatccc    3960
agctactcag gaggctgagg cagaagaatt gcttgaaccc aggcggcaga ggttgcagtg    4020
agtcgagatt gcaccactac actccagcct gggcaacaga gagcgactct ctcaaaaaaa    4080
aaaaaaaaaa aaaaaaaaaa agctaacttt atgtcttgag agtttgtacc attttctttt    4140
gtagtggtca ccttgctaat gcattagttc tgagatattt atctccctca catgtgtgca    4200
aggaagtccc tgttatcgaa tacagatact ttaacaagca gacaaagcag aaacccaaag    4260
tccatactag gaacacccta aattttccaa aagcaaaagt tctcccgaaa tggagacata    4320
caagggactt ttattattct gttactagtt tctataacat ttcttctttc aacagagtat    4380
atgtttccca tttaacccag agcaacatta acttccttag caagtccagt tctaacttcc    4440
aacaagtcca accactgttt ttgaagagca tatcagtaac tatattaaga tgaaggtaac    4500
cacattcgta ttttctcaag attagttatt tgaagctcag cagttttttgt ggtcagaaag    4560 aaattttgct ctattaaacc aatactgcta atataaaaaa ccaccacact gaagaaacga    4620
gggaaaggac gggataagca cagaacgagag aatgactggt tgcttttttgt ctcaatctag    4680 ataatccatt caataagaag taaattaatt atccttaacc aatggtaggc tgagaacaac    4740
```

```
cctcaaaata gatattttt atgttaaatg gggagaaata tctatacttt atgttatact      4800
ggataaaaat gtgttttaag tctaaaaaaa accagacgag ctaaactttg cctagtgtgt      4860
ctacaaccat tttttaggag acgcaggaat accagggcat aataagatca gattggtgta      4920
attttgtatg ttttttgaaat ccttcattaa ttgtagaacc ttgatatgat tagaaacaaa      4980
ctgtatttca acaaacaggt ttcagtattt gcacactgaa aaagtgtttt gtattttaac      5040
tataaatatt tcacgtatct gtatagacca tctagaaatg tagaggtctt acagcattag      5100
aacgaaggaa gtttacatgt gctctatcta tttttctgag cctcttttaa taaagattgc      5160
aagaaggcat aaaacaagag tttgtttcct gaagttttta gtacaattat tgttttccta      5220
ttcaaaaact tgggttttac ctcaagatca tagtattagg aaagtacatt gagttgatac      5280
ggacatggga gaacgaaaat aaaaccaggg caattaatat ccttgtaagg ccaggcgcgg      5340
tagctcacgc ctatataaca gcactttggg aggccaaggc aggcagatca cttgaagttg      5400
ggagtttgag accaccctgg ccaacatggt gaaaccccat ctctatgaaa aatataaaaa      5460
ttagctgggc atggtggcag atgcctgtaa tcccagctac ttgggaggct gaggcaggag      5520
aatcgcttga acccgggagg tggaggttgc agtgagctga gatcaggcca tgcactccag      5580
cctgggtgac agagtgagac tccgtctcaa aagaaaatcc ttgtgagatg aattcgttct      5640
tatttcatat acaaggggac tatgtaagat atgggaaata atataatgta cgttatttat      5700
gtaaatactt tcagtaacaa aaactaacaa atatcaaaaa tctgagccta gacacaaaca      5760
attaaatata agccatagta tgtaacctga cttattgaag gcaggaataa aaagaagaga      5820
gccagaattg attcagttat ttttgtcttc catagtgttg gcagggccct gcatttctct      5880
accttgagca atgaagcagt cccagaattt tggaatatag aaattaggaa ggaaaaacga      5940
actttaaaat attaatttag tagaactgaa agtaatgcat ttcatgcaac agtaaagtgc      6000
ttaaacatgg caaagaaaac taagggacaa gataagaaaa atggttggta agatgggtc       6060 acatccagaa gcccaacata agctattttt ccatcttttt ctgtaccatt taaaagacta      6120
ctaaagagtt caaaacaaac tgtccttggc atttaaagtc aaaacatggt tcttcactca      6180
gtggtgtaaa ttaactactc attggccaaa gagtaaatac aaaaaggaga tgaagttctg      6240
actggtgttg tgggtgagat tttgcagtgt atgtttttac atttgtagtg tacgttttaa      6300
acttccggtt tccttgctgc ctcaacatct ccacaaacag gctgtgagca cctgccccag      6360
tgtgatatgg gtggcccctg ccacaagttt cccttgctac cttgcccatg acctagtaac      6420
atttaaatgc accagtgaaa ttctcttttt cttgtgtgct tctccctgac ccaaaggctc      6480
ctgcccatgt cttaggcctc tccgctcccc acctgcttgg ctgagccccc tcccatgtga      6540 cccctctca gcatgcagtg actggtctct ctaggacctg tgagtatatt acaactttt        6600 ttcctgtgtc tctcctgtga tatctcttgt ggctaaacct cactgaccat aacctaaaaa      6660
aacacataca aaaacatga aagaaaaagt tgtttcttga gctggcctgg acgaacgggg       6720 agccagggc tcgaccctgg ctgttggagg cgcagtgagg cctggtctcc ggctgccaga       6780
ccacgctgag cggagcgcgc ggcaggctcg cctcagcgct gcgggaacg cgcgcgccgc       6840 cgtccgcggt cgcccgtagg tgcctgcacg cgtcggggtc acggcctttg ccgacagga       6900 gcgagaagac tcaggagccg ccccgcgcct tcgatccggc gctgctggag ttcctggtgt      6960
gcccgctctc caagaagccg ctcagatatg aagcatcaac aaatgaattg attaatgaag      7020
agttgagaat agcttatcca atcattgatg ggattcctaa tattatcata ttaggcagct      7080
aggatgacac atcaaagaag caagaagtgg agcagcgcta gttcataatt taaaaaaata      7140
```

```
aaacagccaa ctcttcttag taccatatac ctttaaaac acagtggcaa gtaataagcg    7200
gaagagaaga atctttctgt ctctttctac gttgactgtt cttattccac tggtttattt    7260
agcaggactg ttccactcag cctctgtaga agaaaacttc ccacagggct gcacttgcac    7320
agctagcctt tgcttttaca gcctgctctt gcctattacc ataccggtgt atgtattctt    7380
ccacctttgg acctggatgg ttattaaact cttcatgcat aactgatgca actagagtca    7440
atatgctgta tatattaatg atagctcttg ggcatctatc tctgaaagct caaatggatg    7500
gaatttagtt tgtgggaaag aggctttgct ttgagcatat caggcttagg actgtggacg    7560
gcttaagttg cagacgcttc ttttattgta ctcttgttct gcccgtgttt tttgaaggct    7620
ctgacataac tgcttatca gaagaaacat tttgacagtg tcttgttgga gataaacatc    7680
cctaattgac atgtgatgac tacttcttat tccattcatc taagagtcat tgaaattttg    7740
ttttctttgt tgtttagct tcaaggtctt tggtagtcac atgttaggga tgactgaaat    7800
aattccaaag gagtgatgtt ggaatagtcc ctctaaggga aagaaatgca tttgaacgaa    7860
tgtgatataa aaccacataa tcaaatagaa atttcatgta cttacaaaaa tttagtttgt    7920
aaaattacct tcatttcttt gacattaaat gcttatatta gcaataaaga tgttgacact    7980
ttctcataaa aaattt                                                    7996

<210> SEQ ID NO 15
<211> LENGTH: 3174
<212> TYPE: DNA
<213> ORGANISM: Homo sapiens

<400> SEQUENCE: 15
taataatggc cgtaagctta aaatagatcc agggaggagc tcattaacgt gaacatagaa      60
agcagttccg cacctctggc cttactcctc ttggaaattg ctttggtcca ttttacttc     120 cttttattcg acgcaccaga aaataagact tttaccaaca tttttactgc atttgacgat    180
gaactaattt agaccggcta aaataattgt tccactggga cacaggaatt caacctcagt    240
tcagaaaatc cctgacatct gacgtaggag gatttatagg tttagtggaa attgcttct    300 cctgctctcc agattgcatc ctgtgggttg attttttttt tgcatgagta acatccttc    360 taataatgaa cagaccaata atgtcttaag agagaaaaag aacaatcttt tccttttgc    420 tgtttctgga gagagctgtt tgaatttgga aacccatgtt ggctgtccca aatatggagat   480 ttggcatctt tcttttgtgg tggggatggg ttttggccac tgaaagcaga atgcactggc    540
ccggaagaga agtccacgag atgtctaaga aggcaggcc ccaaagacaa agacgagaag     600
tacatgaaga tgcccacaag caagtcagcc caattctgag acgaagtcct gacatcacca    660
aatcgcctct gacaaagtca gaacagcttc tgaggataga tgaccatgat ttcagcatga    720
ggcctggctt tggaggccct gccattcctg ttggtgtgga tgtgcaggtg gagagtttgg    780
atagcatctc agaggttgac atggacttta cgatgaccct ctacctgagg cactactgga    840
aggacgagag gctgtcttt ccaagcacca acaacctcag catgacgttt gacggccggc    900
tggtcaagaa gatctgggtc cctgacatgt ttttcgtgca ctccaaacgc tccttcatcc    960
acgacaccac cacagacaac gtcatgttgc gggtccagcc tgatgggaaa gtgctctata   1020
gtctcagggt tacagtaact gcaatgtgca acatggactt cagccgattt ccccttggaca   1080 cacaaacgtg ctctcttgaa attgaaagct atgcctatac agaagatgac ctcatgctgt    1140
actggaaaaa gggcaatgac tccttaaaga cagatgaacg gatctcactc tcccagttcc    1200
```

```
tcattcagga attccacacc accaccaaac tggctttcta cagcagcaca ggctggtaca    1260
accgtctcta cattaatttc acgttgcgtc gccacatctt cttcttcttg ctccaaactt    1320
atttccccgc taccctgatg gtcatgctgt cctgggtgtc cttctggatc gaccgcagag    1380
ccgtgcctgc cagagtcccc ttaggtatca acggtgct gaccatgtcc accatcatca    1440
cgggcgtgaa tgcctccatg ccgcgcgtct cctacatcaa ggccgtggac atctacctct    1500
gggtcagctt tgtgttcgtg ttcctctcgg tgctggagta tgcggccgtc aactacctga    1560
ccactgtgca ggagaggaag gaacagaagc tgcgggagaa gcttccctgc accagcggat    1620
tacctccgcc ccgcactgcg atgctggacg gcaactacag tgatggggag gtgaatgacc    1680
tggacaacta catgccagag aatggagaga agcccgacag gatgatggtg cagctgaccc    1740
tggcctcaga gaggagctcc ccacagagga aagtcagag aagcagctat gtgagcatga    1800
gaatcgacac ccacgccatt gataaatact ccaggatcat ctttccagca gcatacattt    1860
tattcaattt aatatactgg tctattttct cctagatgct tgtaattcta caaatttcac    1920
atttccatgg catgcactac agaaataact gtataatgaa aaagtattta aggatatggt    1980
taaaaaaaaa tcccaggacc cacccatgtt ttcactatcc cttctgcagc tttccaaagc    2040
tacattgacg agacacttac tggtttaatt tgcacttatt aaccatctat tgaatacaca    2100
gcattatatt aggtgctgca ggaaatacga cactgtagcg actgatgtta gttgttaccc    2160
agatcccctg gaaaagcaca ctaccagtgt tgtgggcaca tttagttcca cccgttagac    2220
ccttgatgct attcacatga ataatttatt ttcctcaagt gtcattacat tgttcaggct    2280
acgtgaactt ggaagcacct acaggccatt tgcatgaaat tcacatgcac ctaaatcctc    2340
actttgacag aaactcatgc ttcagtttat aacctattac ctattttgta tgcgactcca    2400
cctccgcatg tttatttaa taaaaggcaa tgataacatt cacattattt ttctttatat    2460
gctgtggttc acaggcttta cccttcaca agaaaagctc tttagattgg cgcaattgct    2520
tctgattttg gtgaaatttt ccctggtagg gaaactttga agataagagt acacacatgc    2580
attttgtctg ttgtgtcata gaggtaacta ggctagaaaa tttgtgttta aatgttccct    2640 atttatata atcaccactt catgtttctt cttcttggag catgtccttg ttcaaagaga    2700
agtgctttct cagtgatgtg atatcttcac tgaggaactt gggtagagaa tgatttcttc    2760
tgcataaaca cttcaaggaa atacataatt tgggactact tgtaactcat tagaatgaga    2820
aatactcaca tggtttctta agagaaaaag aacatcggaa agcaaaataa atgggaagat    2880
atcactggac atctgcattt atactcgaaa taccagcatt ttctatggac cagaaaactg    2940
ccatcaccta gaccacacag cccagatacc aggcagacgg atgcccaat ggcaactgat    3000 gtcagggcat ggggtaaagg agagggttct aatctggtgt atcacttaaa aacagttatt    3060
tatattatat atctgctata tagatcaacc tccaccaaac ttacccaaac agcatttgtt    3120
ttatttgaaa ctcactttaa taaagtgaat tatatacaca aaaaaaaaaa aaaa          3174
```

<210> SEQ ID NO 16
<211> LENGTH: 7773
<212> TYPE: DNA
<213> ORGANISM: Homo sapiens

<400> SEQUENCE: 16

```
agagcctcgg tggtttgcag cagtggaacc aggcaggccc agttgtgggt aggagaggcc      60
gtcacctgtt gaggcctccc ccccacaccc ccgcatcgcc ctgccctggc agagcccagc     120
ccccagtccc cggagagcgc gcctgaggac ggacggacgg acggacggac agacctaggg     180
```

```
acggagggcc aggggcaggg gagatccaag aggccccgcg ctggaatgca gttttctcgg    240
gcgagggaga ctttgcaccg gagtggaaaa tagtttgggg tggggtttcg caccgtcccc    300
tcctccccag ccccgggccc cctcccaggc gctttctggg agcttttaga actgcgctct    360
gaagtttcca gagagcgagg agcttttgcg gcaggcagga caatggaag aaaatgaaag     420 ccagaaatgt gagccgtgcc ttccttactc agcagacaga agacagatgc aggaacaagg    480
caaaggcaat ctgcatgtaa catcaccaga agatgcagaa tgccgcagaa ccaaggaacg    540
cctttctaat ggaaacagtc gtggttcagt ttccaagtct tcccgcaata tcccaaggag    600
acacacccta gggggcccc gaagttccaa ggaaatactg ggaatgcaaa catctgagat     660
ggatcggaag agagaagcgt tcctagaaca tctgaagcag aagtaccccc accacgcctc    720
tgcaatcatg ggtcaccaag agaggctgag agaccagaca aggagcccca aactgtctca    780
cagtcctcaa ccacccagtc tgggtgaccc ggtcgagcat ttatcagaga cgtccgctga    840
ttctttggaa gccatgtctg aggggatgc tccaacccct ttttccagag gcagccggac     900
tcgtgcgagc cttcctgtgg tgaggtcaac caaccagacg aaagaaagat ctctggggt     960 tctctatctc cagtatggag atgaaaccaa gcagctcagg atgccgaatg aaatcacaag   1020
tgcagacaca atccgtgctc tcttcgtaag tgccttttcca cagcagctca ccatgaaaat   1080
gctggaatcg cccagtgtcg ccatttacat caaagatgaa agcagaaatg tctattatga   1140
attaaatgat gtaaggaaca ttcaagacag atcactcctc aaagtgtaca acaaggatcc   1200
tgcacatgcg tttaatcaca caccaaaaac tatgaatgga gacatgagga tgcagagaga   1260
acttgtttat gcaagaggag atggccctgg ggcccctcgc cccggatcta ctgctcatcc   1320
accccatgcg attccaaatt ccccaccgtc tactccagtg ccccattcca tgcccccctc   1380
cccgtccaga attccttatg ggggcacccg ctccatggtt gttcctggca atgccaccat   1440
ccccagggac agaatctcca gcctgccagt ctccagaccc atctctccaa gcccaagcgc   1500
cattttagaa agaagagatg tcaagcctga tgaagacatg agtggcaaaa acattgcaat   1560
gtacagaaat gagggtttct atgctgatcc ttacctttat cacgagggac ggatgagcat   1620
agcctcatcc catggtggac acccactgga tgtccccgac cacatcattg catatcaccg   1680
caccgccatc cggtcagcga gtgcttattg taaccccctca atgcaagcgg aaatgcatat   1740
ggaacaatca ctgtacagac agaaatcaag gaaatatccg gatagccatt tgcctacact   1800
gggctccaaa acaccccctg cctctcctca cagagtcagt gacctgagga tgatagacat   1860
gcacgctcac tataatgccc acggcccccc tcacaccatg cagccagacc gggcctctcc   1920
gagccgccag gcctttaaaa aggagccagg caccttggtg tatatagaaa agccacggag   1980
cgctgcagga ttatccagcc ttgtagacct cggccctcct ctaatggaga agcaagtttt   2040
tgcctacagc acggcgacaa tacccaaaga cagagagacc agagagagga tgcaagccat   2100 ggagaaaacag attgccagtt taactggcct tgttcagtct gcgcttttta aagggcccat   2160
tacaagttat agcaaagatg cgtctagcga gaaaatgatg aaaaccacag ccaacaggaa   2220
ccacacagat agtgcaggaa cgccccatgt gtctggtggg aagatgctca gtgctctgga   2280
gtccacggtg cctcccagcc agcctccacc tgtgggcacc tcagccatcc acatgagcct   2340
gcttgagatg aggcggagcg tggcggaact caggctccag ctccagcaga tgcggcagct   2400
ccagctgcag aaccaggagt tgctgagggc aatgatgaag aaggccgagc tggaaatcag   2460
tggcaaagtg atggaaacaa tgaagagact ggaggatccc gtgcagcgac agcgcgtcct   2520
```

```
agtggagcaa gagagacaaa aatatcttca tgaggaagag aagatcgtca agaagttgtg    2580
cgagttggaa gactttgttg aagacttgaa gaaggactcc acggcagcca gccgattggt    2640
tactctgaaa gacgtggaag acggggcttt cctcctgcgt caagtgggag aggctgtagc    2700
taccctgaaa ggagaatttc caaccttaca aaacaagatg cgagccatcc tgcgcataga    2760
agtggaggcc gtgcggtttc tgaaggagga gccacacaag ctggacagtc tcctgaagcg    2820
tgtgcgcagc atgacagacg tcctgaccat gctgcggaga catgtcactg atgggctcct    2880
gaaaggcacg gacgcagccc aagccgcaca gtacatggct atggaaaagg ccacagccgc    2940
agaagtcctg aagagtcagg aggaggcagc ccacacctcc ggccagccct tccacagcac    3000
aggtgcccct ggcgatgcga agtcggaagt ggtgcctttg tccggcatga tggttcgcca    3060
cgcgcagagc tcccctgtgg tcatccagcc ctcccagcac tccgtggccc tgctgaaccc    3120
tgctcagaac ttgcctcacg tggccagctc cccagccgtc cccaggaag caacctccac     3180 tctgcagatg tcgcaggctc cgcagtcccc acagataccc atgaatgggt ctgccatgca    3240
gagcttgttc attgaagaaa tccacagtgt gagtgccaag aacagggcag tgtctatcga    3300
gaaagcagaa aagaaatggg aggaaaaaag gcaaaatctg gatcactata atgggaaaga    3360
gtttgagaag ctcctagaag aagctcaggc caatatcatg aagtcaatac caatctgga    3420 gatgccgcca gccacaggcc cactgccaag gggagatgcc ccagtggaca aggtggaact    3480
ttcagaagat tctccaaatt cggaacagga cttggaaaag ctgggggga agtcgccccc    3540 tcctcctccg ccacctcctc gtcgaagcta cctgccagga tcgggactca ccaccacgag    3600
gtcaggcgat gtggtctaca ccggcagaaa ggagaacatc accgctaagg caagcagtga    3660
agatgctgga ccaagcccac agaccagagc tacaaaatat ccagcagagg agcctgcttc    3720
agcctggacc ccatccccac cgcctgtcac cacctcctcc tcaaaggatg aggaggaaga    3780
agaagaagaa ggagacaaaa taatggcaga actccaggca ttccagaagt gttcctttat    3840
ggatgtaaat tcaaacagtc atgctgagcc atcccgggct gacagtcacg ttaaagacac    3900
taggtcgggc gccacagtgc cacccaagga gaagaagaat ttggaattt tccatgaaga    3960 tgtacggaaa tctgatgttg aatatgaaaa tggccccaa atggaattcc aaaaggttac    4020 cacagggct gtaagaccta gtgaccctcc taagtgggaa agaggaatgg agaatagtat    4080
ttctgatgca tcaagaacat cagaatataa aactgagatc ataatgaagg aaaattccat    4140
atccaatatg agtttactca gagacagtag aaactattcc caggaaactg tgcctaaggc    4200
cagtttcggt ttctctggca ttagtccatt agaagatgaa ataaacaaag ggtctaaaat    4260
ctcaggcctg caatactcta tacctgacac cgagaaccag acgctgaatt acggaaagac    4320
aaaggagatg gaaaagcaaa atacggataa gtgtcacgtt tcctctcaca ctagactaac    4380
agaatcaagc gtgcatgatt ttaaaacaga agatcaagag gttatcacga cagattttgg    4440
ccaagttgtt ctaagaccca aggaggcaag gcatgctaac gtgaaccta atgaggatgg    4500 agaatcaagt tcagttctc ccactgaaga aaatgcagcc actgacaata ttgccttcat    4560
gattaccgaa accactgtcc aggttctttc cagtggggag gtgcatgata ttgttagcca    4620
aaagggagaa gacatacaga cggttaatat cgatgccaga aaagagatga ccccccgaca    4680
agaagggact gacaatgagg atccagtcgt gtgcctggac aagaaaccag tgatcatcat    4740
tttcgatgag cccatggaca tccggtctgc ctataagaga cttt caacta tctttgagga    4800 atgtgatgag gaattagaga gaatgatgat ggaggaaaag atagggagg aggaagagga    4860 ggaaaatggg gattctgtag tccagaataa taacacttcc cagatgtctc ataagaaggt    4920
```

-continued

```
ggccccaggc aatcttagaa ccggacaaca ggtggaaaca aagtcacagc cacactccct    4980
ggccacagag accagaaacc caggaggaca ggaaatgaac agaacggagc tgaacaagtt    5040
cagccacgtg gattctccaa attcggaatg caagggtgag gacgcgaccg atgaccagtt    5100
tgaaagcccc aagaaaaagt ttaaattcaa attccctaag aagcaactcg ccgctctcac    5160
tcaagccatt cgcaccggaa ctaaaacagg gaagaagact ttgcaagtgg tagtctatga    5220
agaagaggaa gaggatggca ccctgaaaca gcacaaagaa gccaagcgct tcgaaatcgc    5280
taggtctcaa cctgaagaca cccctgaaaa cacagtgagg aggcaagagc agcccagcat    5340
cgagagtaca tctccgattt caagaactga tgaaattaga aaaacaccct acagaacatt    5400
ggatagcctg gagcagacca ttaaacagct cgaaaataca atcagtgaaa tgagtcccaa    5460
agccctagtt gatacctcat gttcttccaa cagagattct gttgcaagtt catcccacat    5520
agcccaagag gcctctcccc gacccttgct agttccggat gaaggtccca ctgccctaga    5580 gcccctacg tcgatacctt cagcttcacg taagggctcc agcggggccc cacagacgag     5640
caggatgcct gtccccatga gtgccaagaa cagacccgga accctggaca aacccggcaa    5700
gcagtccaaa ctgcaggatc cccgccaata tcgtcaggct aatggaagtg ctaagaaatc    5760
tggtggggac tttaagccta cttccccctc cttacctgct tctaagattc cagcccttc    5820 tcccagctct gggaaaagca gttctctgcc ctcttctagt ggtgacagct ctaacctccc    5880
taatccacct gctactaaac catcgattgc ttctaaccct ctcagccccc aaacaggacc    5940
acctgctcac tctgcctccc tcatcccttc tgtctctaat ggctctttga agtttcagag    6000
cctcactcat acaggtaaag gtcaccatct ttcattctca ccgcagagtc aaaatggccg    6060
agcaccccct cctttgtcat tttcctcctc ccctccttct cctgcctcct ccgtctcact    6120
gaatcaaggt gccaagggca ccaggaccat ccatactccc agcctcacca gctacaaggc    6180
acagaatgga agttcaagca aagccacccc atccacagca aaagaaacct cttaaaggtc    6240
aaatcctatt aggcacaagt cggagttaca tttaaaaaaa attaacagtc tacaacaact    6300
gttttcacaa gagaatgtaa catattgctg tatcgtttga ggcttaatgc taaatatgtg    6360
ctaaatactg gattaataga tttcagtaaa gctcgttcgt tttgtttggt tttcttttta    6420
cctagttgct atagtgtcta cagtctatac tcaataccta taaatgcag taagcatgtg     6480 ttacagaaag aggttctggt gggagagaaa ggtgcgtgtg agacaggaga attgtcttaa    6540
gcatataaaa catgtatgat tccagaattt tagtatgttt tgtataaaac tattttttcat   6600 tacggagact agaagtgaac agagaattac acaagtgtga ctatacaaat tgtaaaacag    6660
atactataat atttcctttt attttagtgt tatttagctt tattacagat ttctattttt    6720
gtcaaaactt catggttcct ttcaagatct tttttgccaa aacatttga tactatagca     6780 ttgtacattt gaaagtagtg ttctagacta taaaaccaat gaacttctac atgagcccta    6840
cagacaggca tgtgtagaag gcaatttatc aaacctattg cactgccatg aaaagtgtgt    6900
ataataattt gctagcccaa gcaagctagt tttctttgct tgcttctttt ctttcttttt    6960
tccttccttt ttttttttt tttctttttt aacatgttga gattctctag ttgttttctt     7020
tggcgtatct aaccccttct tttgttttct gagacctggt aacccacgct cttgcattgt    7080
ggattttaaa atgtatactc tgtacggttc tgtaaaccga aaacttttg taaatatata     7140 aatatacata gacataaaaa tactgtatgt gacagcacat agagtagttt tcccacacca    7200
aagttaattt ttatgcatgc tttaaaagta tatatcggga ccggcagaaa tggaagtatc    7260
```

| | |
|---|---|
| catacattttt aaaaagcaa caagtttgca cagctagagt gttttgtaa ataaatgtat | 7320 |
| ttgtataaca cagtcatgta atatacagaa ctataagcag agactttgca aaactaaata | 7380 |
| aagggctgca tgcttattat tttttgtacc ttgtcactat aactacttcc tagtcaaaga | 7440 |
| acgaaatgta actgttaccg agttaaatgt ttttccgctt tgagggatgt aaccacatcc | 7500 |
| actcagagga cactactttt ctgaaagctc tggggtgact aatgatgagt tcctaataaa | 7560 |
| ttaattgcaa gtgtggtgcc ttggatgtgg cctgttggct cgctttcttc tctgtggctt | 7620 |
| atcaaggtgt agatgacaga agcaaacct ggatacagag tttccaccct cagttcctgg | 7680 |
| aggggctctt attattttct ctcttttaa aaaacttcca gtagaagtaa agtggaaata | 7740 |
| aaatgtcttt atcaaaaaaa aaaaaaaaaa aaa | 7773 |

<210> SEQ ID NO 17
<211> LENGTH: 10264
<212> TYPE: DNA
<213> ORGANISM: Homo sapiens

<400> SEQUENCE: 17

| | |
|---|---|
| ggagccgccg ggaggtaggc gcgggacggg cggctgcggt ggcggcgggt ggaccgattg | 60 |
| tcgctcggcg gcgggagtcg gtggagtctc gctcttcgc aaggctggag tgcaatggca | 120 |
| tgatctcggc tcactgcagc ctccgcctcc tgggttcaag tgattcttct gcctcagcct | 180 |
| cccgagtagc tgggactaca gaaatgctgg taatttcagt cacttgctga tgacttctga | 240 |
| tgtcccagca aatgttggca ttgttgactg ctgagaagat acttctgagg acccacgtct | 300 |
| aaggtggact tggttcgcac tcttctggtt agtccctgaa caggagtgat gcctccaggc | 360 |
| aggtggcatg ctgcctatcc agctcaggcc cagtcttcga gggagcgagg gcggcttcag | 420 |
| acagtaaaga aggaagaaga ggatgaaagc tatactccag tgcaggctgc caggccacag | 480 |
| actctcaacc gccctggcca ggagctgttc cgccagctct tcagacagct tcgctaccat | 540 |
| gagtcttcag ggcccctaga aactctgagc cggctccggg aactctgtcg ctggtggctg | 600 |
| aggcctgacg ttctctccaa ggcacagatc ctagagctgc tggtgctgga acagttcctg | 660 |
| agcatcctgc tggggagct ccgggtttgg gtgcagcttc ataaccctga gagtggcgag | 720 |
| gaggctgtgg ccttgctgga ggagctgcag agggaccttg atgggacatc ctggagggac | 780 |
| ccgggcccctg cccagagccc agatgtgcat tggatgggta caggagccct gcgatctgca | 840 |
| cagatatggt cccttgcttc acctctcagg agcagctctg ctctggggga ccacctggag | 900 |
| cctcccctatg aaatagaagc acgtgacttc ctggctgggc aatccgatac tcctgctgcc | 960 |
| cagatgcctg ccctttcc gagagagggg tgcccgggag accaggtaac accaaccagg | 1020 |
| tccctgacag cccagctcca ggagaccatg actttcaagg atgtggaggt gaccttctcc | 1080 |
| caggacgagt gggggtggct ggactctgct cagaggaacc tgtacaggga tgtgatgctg | 1140 |
| gagaattata ggaacatggc ttccctggtg ggaccattca ccaaacctgc tctgatctcc | 1200 |
| tggttggaag caagggagcc atgggggctg aacatgcagg cagctcagcc taaggggaat | 1260 |
| ccagttgctg ctcctacagg agatgacctc cagagtaaaa caaacaaatt catcttaaat | 1320 |
| caggaaccttt tggaagaagc agaaaccttta gctgtgtcat caggatgtcc tgcgacaagt | 1380 |
| gtttctgagg gaattgggct cagagaatct tttcaacaga gagcaggca aaggatcaa | 1440 |
| tgtgaaaatc ccatacaagt aagagttaag aaagaagaga ccaatttcag tcacaggaca | 1500 |
| ggaaaagact ctgaagtatc aggaagtaat agtcttgact taaacatgt tacatatttg | 1560 |
| agagtttctg gaagaaagga atcccttaaa catggctgtg gcaaacactt cagaatgagt | 1620 |

```
tcacaccact atgactacaa gaaatatggg aagggggctca gacacatgat tgggggcttc   1680
agcctacatc agagaattca tagtggactg aaagggaaca aaaaggacgt gtgtggaaaa   1740
gacttcagcc ttagctctca tcaccaacgt gggcagagtc ttcacacagt gggagtgtca   1800
tttaagtgca gtgactgtgg aaggactttc agtcatagct cccatcttgc gtatcatcag   1860
agacttcaca ctcaagagaa agcatttaaa tgtagggtgt gtgggaaagc cttccggtgg   1920
agttccaact gtgcgcggca tgagaaaatt cacactggag tgaagcctta taaatgcgat   1980
ttatgtgaga aagctttccg acgcctgtca gcctaccgtc tgcaccgaga acccatgct    2040
aagaagaaat ttcttgaatt gaatcagtat agggcagctc tcacctacag ctcagggttt   2100
gatcatcatt tgggagacca aagtggggag aaactctttg actgcagcca gtgcaggaaa   2160
tccttccact gtaagtcata tgttcttgaa catcaaagga ttcacaccca ggagaagccc   2220
tataaatgta ccaaatgtag gaaaaccttt agatggagat caaactttac tcgtcatatg   2280
aggttgcatg aggaggaaaa attctacaaa caagatgaat gtcgtgaagg cttcaggcaa   2340
tctcctgact gcagtcagcc ccagggtgct cccgctgtgg agaaaacatt tctgtgtcag   2400
cagtgtggga aaactttttac tagaaagaaa actctcgttg accaccagag aattcacaca   2460
ggtgagaaac cttaccagtg tagcgattgt gggaaggact ttgcctatag gtcagccttt   2520
attgttcata agaagaagca tgccatgaaa agaaaacctg agggcgggcc atcttttagt   2580
caggacacag tgttccaggt tcctcagagc agtcactcca agaggagcc  ctacaaatgc   2640
agccagtgtg gcaaggcctt ccgcaatcac tcattcctcc tcatccatca gagagttcac   2700
actggagaga agccatataa gtgcagggag tgtgggaaag ccttcagatg gagttccaat   2760
ctctaccgac atcagaggat tcactctctt caaaaacagt atgattgcca tgaaagtgaa   2820
aagactccaa atgtggagcc aaaaatcctc actggtgaga acgtttttg gtgtcaagaa   2880
tgtgggaaaa cctttacacg taaaagaacc cttttagatc ataagggaat acacagtgga   2940
gagaagcgct ataaatgtaa tctatgtggg aaatcttatg atagaaacta tcgccttgtt   3000
aaccatcaga ggatccactc tacagagaga ccttttcaaat gtcagtggtg tgggaaagag   3060
ttcattggga gacatacct ttccagtcac cagaggaaac acaccagagc agcacaggct   3120
gaacgtagcc cgcctgcacg gtcttcctct caggacacaa agttgagatt acagaagcta   3180
aaaccaagtg aagagatgcc cctcgaagac tgcaaagaag cttgcagcca gagctccagg   3240
ctcactggac tccaggacat aagcattggg aaaaagtgcc acaaatgcag catatgtggg   3300
aaaacttttta acaagagttc acaactcatt agccacaaga gatttcatac tcgagagagg   3360
cccttcaaat gcagcaagtg tggaaagacc ttcaggtggt cttcgaacct ggctcggcat   3420
atgaaaaacc atattagaga ttagcctggg acctgacagt gacagtgggg gtgggttctc   3480
agtcccctgc tagagaaccc ttaattatag gcattgtgga gtaactttga taaagggccc   3540
agcccttctct gttttggaag ctagtgacag aatcccaagg atttgaaagc tcggggagtc   3600
cccagcctgc ctgctaggat gtgacgctgg ggaagtgcag caccatgtcc tttggagccc   3660
ttctggagac tccggcccct aggagtggcc tctgcaccat agcctgcggc tcccctattc   3720
aggtctcctt ccacaactct gaagagagag accactgccc tttgtggttg gacagaatat   3780
ctgtggcatc atgggctatg gctgctggaa aggggccagt gggatcctag atttgtcttc   3840
aagtttggcc tgtggccatg cctattctgt tgactttaaa agcagcagca tcaagaactc   3900
ctagccttcc caaatgcccc ctggggagtt ctggctgggg cttcagcctt cctggctggc   3960
```

```
tttggatat ctgctagggg gttagagtgg tctcagcggc aggtggagga gagcaggatg    4020
ctgggctcaa gcgcttggcg tgtggatctc taccagtacc ctgttgccat ccccatccca    4080
caggcctgca taggcagcag cggtccatct gtttaacaga aatgtgctga gcactcccat    4140
acaccaggcg ctggtgtgtt tgccagagac ccagcaggga ccagaacaga tgaaaatcct    4200
gccatcttgg atctttacag atgacaaaca atgggatac gcagtattct ggatggtgat    4260
gtgtgtagtg gacaaagtga atcagagaag agcagaggga gtgctggatt gggagatcag    4320
tcgtgatttt agatagtctg gtcagggagg gcctcaactg agaaggtgaa atgtgagcaa    4380
agacgtgaag gaagccaggg aggtagcagg tagctctcta gggagagttg caggcagagg    4440
agattgggtc ttgactggtg tcctcaggaa ggaagcccct gggatggagt gcagggagcc    4500
agctggaagg gaaggagagg ggccagggag gccacaggcc cggccatatg agcatcatgg    4560
gtcattacgg gggcttgagc tggctcagag ggaggcaggg agcttttgga caattttgag    4620
ttgaggagtg atgtggtttg aatctgaatt atattttata aggttaacc acagatccaa    4680 ggactcagta aaagggtgaa aggcttctca tgcagttagc cttgctgcca gttcccataa    4740
atcagactcc tccccactcc gtttctgaat tttctatagg atcctcggcc tcagcagata    4800
taaacgctta ccattgttgt gttcatgtct ctagcccctg cacactgcag gcccctctca    4860
gcttcacata cccctctcca tgtatgagat ctggtgctag caatcagatt caacccgaag    4920
gaacaagtgc atgtgcctgc tgctctcagg agaaaaggca gcctgttctg ggaggagctc    4980
cctcactggc ccacccactt gtgttgaagc aaaaagcaag aatcaattac ttaaaggcaa    5040
aggagtgata ttgctaaagc atgtgagtaa tcattgcttc tgattattga agaggtcaga    5100
ttatgaatga aaggataaaa tgttttaata gtagagcagt gtcctgacta taggggcccg    5160
ttcatggagc tggtcatttc ttgaaatgag aagaaaccaa cctggaagat gtcttttca    5220 gtagagtatg gaataatctt acctgctctg gattgccatg agcaggtgaa aatgaaggct    5280
ctgatattgt gtggtggtgt cacaggatgg tgggggcggg gcagaagtct cctgttggtg    5340
ttctgatgcc tgttcagctt tgtcctcagg aaggtttggt catcttggtt ctgccatcct    5400
cttgccttcc tacggcagca gctgttcatg gcactgaaga tgtcccttca ctgtcccaaa    5460
actggcacta gaagtggctg gcaggggggg ccagagtcat aggaagggtc ttggagtcat    5520
cagatctggg ttccaggcat ggtgtgcctt tccttggcag gattgatctt gagcaagtca    5580
atgaacctct gcatcaattt ccttatgtgt gaagttagag tgcttggctg tgctacctga    5640
ttcctgagat tggtgaaaga gggcttggtt taccaaggct ctccatcagg tggttgacct    5700
ctaggaccag ggccctctca gaggtgcagc ttccatgtca gttggtgttg taaccatgga    5760
aaagtccctt tccaatcaaa cttttagcac ccctttcccc ccatctctgc tccctttgcc    5820
acaggatacc ttgtaaagtt cctgcccag tatagggata ttttactgt cttttttatt    5880 ttttgagaca gggttgccca gggtggagtg cagtggcagg atcacagctt actgcagcct    5940
tgacctccca ggctcaggtc ccatctgagc ctcccgagta gctggggcta caggtgtgtg    6000
ccaccctgcc agctaatttt ttatatttt ttgtagagac aaaactttta ttttttttc    6060 ccatgttgct catgctggtc tcaaactcct gggctcaagc aatccaccca cctctgcctc    6120
ccaaagtgct gggattacag gcgtgagcca ctgtgcctga cctgtcattt ttatagaatg    6180
aaatgtgctt atttctaaac attctaatca aattttaaaa tgtgcaaaga atgaagtgaa    6240
aaactgaatt ttttttttt tttgatacgg agtctcactc tgttacccag gctagagtgc    6300
agtggcgcga tctccgctca ctgcaagctc tgcctcctgg gctcacacca ttctcctgcc    6360
```

```
tcagcctcct cagtagctgg gactacaagt gcctgccacc acgcctgggt tatttttat    6420
attttagta gagacggggt ttcactgtgt tagccaggat ggtctcgatc tccaggatgg    6480
tctcgatctc caggatggtc tcgatctcct gacgtcgtga tccacccgcc tcggcctccc    6540
aaaatgctgg gattacaggt gtgagccact gtgcccggcc aaaagaacag aaattatttt    6600
atcctgaagt aagctgttta tatttgggat tatactgaac ctatttgtcc aataacctga    6660
gttttcaaat aatttagtt ctataagtac tataattata taaatattaa tgaattcaga    6720
ttagctgaaa ggaaaaaaag tagaagcctg actacttggt gctaactact aaagattttg    6780
gcagaatcaa tgttggattt ggcttttcctg tccttcccc atgccagccc ccagagtgt    6840
tctgccttgt gctgcctccc ttcacctgga gtgccacacc cctctctctg ccagttcagc    6900
tcttcattct tcaaggcctg accttgtctg acccttgtgc ctctaaaccc gtggccccac    6960
ctctcttggt tcctatgtca ggtgatgttt gtgtttttgg ttatgcccat ctccatagcc    7020
agaccaagca ctctggaagc cagggttggg tgcttattta tctgtttgcc atgcagaaaa    7080
tatcttgcac aaaattacct ctgttaagga atctgaagct gaatttagtt tggctgagtc    7140
agggttgggt tttttttaag gggctgtggg gtgaaatgtt gactggaagc cacccacaaa    7200
cacacacctg ctggttagga acccggctgt gggtggttct gagctgtttg gcttcagttg    7260
acagtttctg attgccctga gcaccaggtc tcatcttgca tctcatcctg gcctggagaa    7320
cattcagttt ccttccaacc cttcccacct ttcccccact cccttggagg aactgaagtt    7380
ggggttgagg agagccagat ggctggagtg ggtatttgaa ggtctttctg tcacctgttc    7440
agtgtggtct gccccacccc tgctgaccaa gactgactga aatgtaaaat aatacagacc    7500
atctcacact cagaaagctg gcacattttt gaaagcccaa gtgtgggtaa gtgcgtggaa    7560
caacgataat tcacactgct ttatgagtag aaattgtgag aaatattgtg ccaggcaatt    7620
tgcaaaatct tggaaggttg tgtgcactta accacccagc aactactcct ggatgcatcc    7680
tagagaagtg ccatgtgaac agagaatgat tttaagactt cactgaagta ttgtttaggt    7740
agcaagattg ggaaaagcct gcatttcatc agcagaagaa tggataaata atgggttgt     7800
ttttggtcct tggaaagtga atatgaaaga gttacgtctc aacacagata gatgaaaaat    7860
tatgctgaga aagttggtga agctacatac aaggtaccct tagtgtaaag ttaagcatac    7920
tgtgtacctg tgggcacgtt acttcaactt gtttttcact ttttctgtaa aatgggatag    7980
tagtggcaat ctcacagggt gattgtgggt gggggggtgg tcaatgaagt aatgcatgta    8040
aaatgcttag aatagtgtct agcatgtaag ccttgtggac atatagaaag tgttattgtt    8100
ttgcacagta atctattttc tgtggattca aataatatga aatgagtata aaatcatgta    8160
ttggaacgat gtgtgcaagt caccattctg ccttcctaag gcaggagacc tgatggattt    8220
ggggagggta catggggcct tcagttgtgt tttctttgtt tttttctaaa aattgatgca    8280
gaggcatcac aatgttaaga tttttacagg gtagtgtggt gggtacttt taactgtttg    8340
cttaaagtgt ttcaaagtaa aaatatttct taagcatagt ctctgacatc ttatgacttt    8400
atagaaatcc ctgccaggta catgatgtta cttagagtga ccacctaat ctttcaaggc    8460
ttccattcc tcacctgcaa aaatttgggag tgtcagaggc gtttgaacca gagtgactcc    8520
atcttgaata gggaactggg taaaataagg ctgagaccta ctgggctgca ttcccaggag    8580
gttaggcatt ccaagtcatg ggatgagata ggaggtcagc acaagataca gtcataaaga    8640
ccttgccaat aaaacagcat gtggtaaaga agccggtcaa aaccaagatg gcaatgaaag    8700
```

| | |
|---|---|
| tgacctctgg ttgtcctcac tgctgtaatt atactgtaat tataatgcat tagcatgcta | 8760 |
| acagacactc ccaccagtgc catgacagtt tacaaacgcc atggcaggcc tggcacgatg | 8820 |
| gctcatgcct gtaatcccag cactttggga ggccaaggcg ggcggattat gaggtcagga | 8880 |
| gattgagacc agcctggcca acatggtgaa accctgtctc tactaaaaaa tacaaaaatt | 8940 |
| agctgggcat ggtggcacgt gcctgtaatc ccagctactt gagaggctga ggcaggagaa | 9000 |
| tctctagatc ccgggagttg gaggttgcag tgagccaaga tggtgccact gcactccagc | 9060 |
| ctgggtgaca gagcaagact ctgtctcaaa aaaaaaaaa aaaatgcca tggcaacatc | 9120 |
| aggaagtaac actatatggt ctaaaaagga gaggaaccct cagttctggt aattgctcac | 9180 |
| acctttcccg ggaaacttat gaataatcta ccccttgttt agcatataat caataaataa | 9240 |
| ccataaaaat aggcaaccag cagcccttgg ggctactctt cctatggagt agccattctg | 9300 |
| tatttctttta ctttcttaat attaactact ttcactttgt ggactcgccc gaattctttt | 9360 |
| cttgagcaag gtccaagaac tctctcttgg ggactggatc acgaccgctt tctggtaaca | 9420 |
| ggagcaatac aaatggctat tagtaaacga acgcttaagt aactctagta catctatgat | 9480 |
| gaaataccag gccacagttt ttttaaaaat gaggatgttc tctatatact gacgcacagt | 9540 |
| caccaagaca tgcactttat aggaaattat aagctcctcc ttgcctaaat ctccttaatt | 9600 |
| ttgcttaata ataacaagt gaagccagaa gctgtaaact cataatttta atgaagaaat | 9660 |
| gggatccaga gatggagat gttttttcatt ctactttatt agatgaggaa aaggagagta | 9720 |
| aatacttgta tgccagctac cacacctttt aaagttaatg ttaaccctgc taagaacagc | 9780 |
| aaggagattt tatatcagcc aggttttagt tgccagaaac cacaccagtt attttagcaa | 9840 |
| agaccttata agaagtgta ctatatttaa gtagctaaaa aggcaagaag aaaatgccaa | 9900 |
| ggtgtcttgg aggtagcaac tgctaagcag ctgccacccc aggactgggg gagctagaat | 9960 |
| agagtctccc catgtttgac gtttgtctgc taatagcatt caagctctcc ccctcagttt | 10020 |
| gcctggatct ggacaagctg ataagaaagc ccagccactt cctctttgcg tcagagggga | 10080 |
| agttcaaact gtgcaaaccc tgactgtcaa atgcactgag ctctcataac cacaacaaaa | 10140 |
| accagagcca cttgttcgtc ctttcactga agcccaacag actggcgtgg gtgcccgctt | 10200 |
| tgctttccct agaaggcctc atgtgagtag taaacttttt cataacctca aaaaaaaaaa | 10260 |
| aaaa | 10264 |

<210> SEQ ID NO 18
<211> LENGTH: 1330
<212> TYPE: DNA
<213> ORGANISM: Homo sapiens

<400> SEQUENCE: 18

| | |
|---|---|
| aaaaagaact gcttctcttt ctttccccct ccaagttcct agtggagggc tgagtccagc | 60 |
| atcccagact cgtgtgacta tataggcaag catttgggga cctacttcac tttgataccc | 120 |
| tagccttcag cagctcaagg tgttggcctt tggataggag gcttccaagt agtaaagctc | 180 |
| cctgctctca gcaagcccaa caccatgggg aagggagatg tcttagaggc agcaccaacc | 240 |
| accacagcct accattccct catggatgaa tatggttatg aggtgggcaa ggccattggc | 300 |
| catggctcct atgggtcggt atatgaggct ttctacacaa agcagaaggt tatggtggca | 360 |
| gtcaagatca tctcaaagaa gaaggcctct gatgactatc ttaacaagtt cctgccccgt | 420 |
| gaaatacagg taatgaaagt cttgcggcac aagtacctca tcaacttcta tcgggccatt | 480 |
| gagagcacat ctcgagtata catcattctg gaactggctc agggtggtga tgtccttgaa | 540 |

```
tggatccagc gctacggggc ctgctctgag ccccttgctg gcaagtggtt ctcccagctg    600
accctgggca ttgcctacct gcacagcaag agcatcgtgc accgcctgat gcccagcctt    660
tctgctgctg gtagggactt aaagttggag aacctgttgc tggacaagtg ggagaatgtg    720
aagatatcag actttggctt tgccaagatg gtgccttcta accagcctgt ggttgtagc    780 ccttcttacc gccaagtgaa ctgcttttcc cacctcagcc agacttactg tggcagcttt    840
gcttacgctt gcccagagat cttacgaggc ttgccctaca ccctttcct gtctgacacc    900 tggagcatgg gcgtcatcct ttacactcta gtggtcgccc atctgccctt tgatgacacc    960
aatctcaaaa agctgctaag agagactcag aaggaggtca ctttcccagc taaccatacc   1020
atctcccagg agtgcaagaa cctgatcctc cagatgctac gccaagccac taagcgtgcc   1080
accattctgg acatcatcaa ggattcctgg gtgctcaagt ccagcctga gcaacccacc    1140 catgagatca ggctgcttga ggccatgtgc cagctccaca acaccactaa acagcaccaa   1200
tccttgcaaa ttcgacctg aaaatggctg agggaggggg ctaagagagg agcaaagcag   1260
gaggtcttgg gctaaaaatc ttttttacca aaaataaatc taagtctgat ttagtttcat   1320
caaaaaaaaa                                                          1330

<210> SEQ ID NO 19
<211> LENGTH: 2779
<212> TYPE: DNA
<213> ORGANISM: Homo sapiens

<400> SEQUENCE: 19
ccggggaccg tttgtagtta ggatccgctg tggcgtcctg agtggagttt gggaccccag     60
ggagggaggg tgtgggcgtt cgggtccaga ggagctgttt agtatccaag atgaatgaca    120
gcctgtttgt cagtttggac agacttttgc tagaatttgt cttccagtat gagcaagaca    180
taagtactaa agaagagatg attcaaagaa ttaataaatg ctgtgaagat attaaggaaa    240
acaaagtaac tatttgtagg atacacgaaa ctataaatgc aacagatgag gaaattgatc    300
attactgtaa acatagtgag gagattaaag acaactgtag aaactggaag ccaacatgtg    360 atgttttcg taaacatgaa gattatatgc aggaccaatt tactgtttat caaggaactg    420
ttgaaaaaga caaagaaatg tatcatgatt atatatgtca gtataaagaa gttttgaagc    480
agtaccaact aaaatactca gaaacacccr ttcacgtga atattatgag aagaaaagag    540
aacatgaaga aattcaaagc agagtgttgg catgtactga caattaaaa atgaatgaaa    600 caatttttat gaaatttcga gtgcctgctc cctttccatc acttactaaa tggactttaa    660
acattgttaa tttgagatgt gaaacacaag atattcttaa acatgccagc aatcttacca    720
aaagttcatc cgaattgaag aaagaagtag atgaaatgga aatagaaatt aattatttaa    780
accagcagat atctaggcat aatgaaacta aggctctttc agaaactctg gaagaaaaga    840
acaaaaatac agaaaacaga aaagaactga agaaagaat ttttggaaaa gatgagcatg    900
tacttacatt gaataaaact caaagcagtc aattatttct tccttatgaa tctcagaaat    960
tagtaagacc aataaagatg cattcttcag aaccaagagt tgcagatata aagaagaaa   1020 gttctgcgaa gcagtcaaag cttgccaata ttgactttag acaaaagaa atgatacac    1080 agatatttaa tgactctgct gtggataacc attcaaaatg ttcacatatt acgactatca   1140
caagttcaca aaagttatg caagtcagat tgttaacccc acagaaacaa tcaaattcca   1200
atcagtggtc ggaaaaaggg gataaagatg ctgagtatgg agataaaggg acagtaagac   1260
```

```
aagtaagaga atcaaaatgt acttcacaag ctatatatac tgaacatttt gggaagtcaa    1320
tagaaaatga tagtgatgaa gtagaagaga gagctgagaa ttttccacga acgtctgaaa    1380
ttcctatatt tttaggaact cccaaagctg tgaaagcacc tgagtcattg gagaaaataa    1440
aattccctaa aaccccccg ttcgaaatta acagaaatag aaatgcagta cctgaagttc      1500
aaacagaaaa ggaatcccct ggactttctt ttcttatgag ttatacttct agatcacctg    1560
gattgaattt atttgattct tctgtatttg atacagaaat ctcatcagat cagtttaatg    1620
aacattattc tgcaagaaat ctaaatcctc tgtcatcaga gcaagagatt ggaaacttac    1680
ttgagaagcc agaaggagaa gatggcttta cattttcttt tccatcagac acttcaactc    1740
atacatttgg agctggaaaa gatgatttta gttttccatt ttcatttgga cagggtcaaa    1800
attcaatacc ttcttcttct ttaaaaggtt tttcatcttc ctcacaaaat acaacacagt    1860 ttacttttt ttgagctagt cattaattcc ttaaattatt ttactgttct gtgttcatga     1920
gggcataaat ttacattatt gcttaaaaca tgaagactgc tttctttat tgattaaagc     1980 agtaatgttt acattatttg attatattta ttgaaatatt gaaatactga atattttggg    2040
ttttgtgtgt gctattaact aatcattatt tattttggtt ttgattttgc gagccgtggt    2100
caggtagaac ttttattaat cttaatagaa tttgatgctt ttttcattac tctttattta    2160
aatattaagc ctgcttctcc ttggaaccta aggttttttt ctggaagtat tgttggtact    2220
ttgataagaa caagaactgc agtagtaact ccagagttag tgctgaagcg tactttagct    2280
actaaaaatt tctattaaaa ttattgggtt tcacttctgc ttcactatgt agtatacaga    2340
gtggtactgt aataataatt tcaaataatt tatgttaata acaaaatctg tgttattttc    2400
ttctaatata acacatggta caattctaat tttatgagtt atgctaatgc tttcaatggc    2460
taaaaattaa atgtaaaggg caagagtaat ttctgaaaat tggattgttg tatcagtggt    2520
gatcctgtta atattctttt ttgcttaaat atttttgaa gaacatttac aattttgtct     2580
ccttcaataa caaaaatttc ttctttatgt tttgtgttca gtatttgtca attaattata    2640
tagcttaagt gaagatattt aagatttgat gaacttctgt aaacattttg ctcaatatca    2700 ttgtatttg tgctttgtaa attagctgta ctgagttacc aagtaataaa gggtttgact     2760
ccaaaaaaaa aaaaaaaa                                                   2779
```

```
<210> SEQ ID NO 20
<211> LENGTH: 4144
<212> TYPE: DNA
<213> ORGANISM: Homo sapiens

<400> SEQUENCE: 20
```

```
ggaccggaag tggaagtggt cttccaaggc ttttttgccg ctggtgtcag gagtattttc       60
atattccaat accgataaat ctttgaggtt tctgggtgtc tctggggagc ccctgggcca     120
gattttcctc tagactccag cccatctctt cagagcagct ctgcttgagt tcacagatga     180
ctgccaagct tcagacaccc tacagaaaaa gggttgagac ccagtgtggc catgccagct     240
aattggacct cacctcagaa atcctcagcc ctggctccag aggatcatgg cagctcctat     300
gagtgttaac cttgatgcct gaaagaactg gaaattatga agatagattc agaagtcaaa    360
tatgttaact aactgcattg aagagtagaa gaaaacaata gcctaggatc agtgtccttc    420
agggatgtgg ctatcgattt cagcagagag gaatggcggc acctggaccc ttctcagaga    480
aacctgtacc gggatgtgat gctggagacc tacagccacc tgctctcagt aggatatcaa    540
gttcctgaag cagaggtggt catgttggag caaggaaagg aaccatgggc actgcagggt    600
```

```
gagaggccac gtcagagctg cccaggagag aaattatggg accataatca atgtagaaaa    660
atcctcagtt ataaacaagt atcctctcaa cctcaaaaaa tgtatcctgg ggagaaagct    720
tatgaatgcg ccaaatttga aaagatattc acccagaagt cacagctcaa agtacacctg    780
aaagttcttg caggagaaaa gctctatgta tgcattgaat gtgggaaggc ttttgtacag    840
aagccagaat ttattataca ccagaaaacc catatgagag agaaacccct taaatgcaat    900
gaatgtggaa aatccttttt tcaagtgtcg tccctcttca ggcatcagag aattcatacc    960
ggagagaaac tctatgaatg cagccagtgt gggaaaggct tctcttataa ctcagatctc   1020
agtatacatg agaaaattca tactggagag agacaccatg aatgcactga ctgtggcaaa   1080
gcattcacac aaaagtccac actcaagatg catcagaaaa tccatacagg cgagagatcc   1140
tacatctgta ttgaatgcgg acaggccttc atccagaaga cccatttgat tgcacaccga   1200
agaattcata ctggagaaaa accatatgag tgcagtaact gtggcaaatc cttcatttcc   1260
aagtcacaac ttcaggtaca tcaacgtgtt cacacaagtg taagcccta tatatgtacc   1320 gaatatggga aggtcttcag caataattcc aacctcgtta cacataagaa agttcaaagt   1380
agagagaaat cttccatatg tactgagtgt gggaaggcct ttacctacag gtcagagttg   1440
attattcatc agagaattca cactggagag aaaccttatg aatgcagtga ctgtgggaaa   1500
gccttcactc agaagtcagc actcacagtg catcagagaa ttcatacagg agaaaaatcg   1560
tatatatgca tgaaatgtgg actggccttc attcagaagg cacacttgat tgcacatcaa   1620
ataattcata ctggagagaa acctcataaa tgtggtcact gtgggaaatt gtttacctcc   1680
aagtcgcaac tccatgttca taacgaatt cacacaggag aaaagcccta tatgtgcaat   1740
aaatgtggga aggcattcac caaccggtca aatctcatta cacatcagaa aactcataca   1800
ggagagaaat cttatatatg ttccaaatgt ggaaaggcct tcacccagag gtcagacttg   1860
attacacatc agagaatcca tactggggag aagccttatg aatgcaatac ttgtggaaaa   1920
gccttcactc agaagtcaca cctcaatata catcagaaaa ttcacactgg agagagacag   1980
tatgaatgcc acgaatgtgg gaaagccttc aaccagaaat caatactcat tgttcatcag   2040
aaaattcata caggagagaa accctatgta tgcactgagt gtggaagagc tttcatccgc   2100
aagtcaaact ttattactca tcaaagaatt catactggag agaagcctta tgaatgcagt   2160
gactgtggga agtcctttac ctccaagtct cagctcctgg tgcatcagcc agttcacaca   2220
ggagagaaac cctatgtgtg tgccgagtgc gggaaggcct ttagtggcag gtcaaatctc   2280
agtaagcacc agaaaactca taccggagaa aagccctaca tttgttctga atgtgggaag   2340 accttttcgac agaagtcaga gttgattaca catcacagaa ttcatactgg agagaaacct   2400
tatgagtgca gtgactgtgg gaagtctttc actaaaaaat cacagctcca agtgcatcag   2460
cgaattcaca ctggagagaa gccttacgtg tgtgctgagt gtgggaaggc ctttactgac   2520
aggtccaatt tgaataaaca tcagacaaca cacactggag acaaacccta caagtgtggc   2580
atctgtggga aaggcttcgt tcagaaatca gtgttcagcg tccatcagag cagccacgct   2640
tgagagaaac agtgtgagaa acccccctg agggttgggt ctgattgtac actgttgcac   2700
gcatgcagca gaaaaatatg tatattattg taaaatagaaa tgaccacagc agaatgtcac   2760
acatggctgt tctggagagg gcctctgaga aggcactgaa tgaggcgagg gacccttcct   2820
acattgtcac catccccagt aaaccttggg tcattattca tactgacaag gaaccgagtc   2880
aatttggtga ataggaaaag ccttctcatg aaaactacaa tagaatactg ttaccaaatt   2940
```

```
cttcctaaga aagatcgtat taagttaacg ataatcctgt ttactgtgga ttaggtatag    3000
tgccaacaaa ttgaatgata aaacaacata atacgtagtt attttgatag tgatgaatcc    3060
taagttatgt gagttgttcg ttgtggaaca cattgtgtaa cagactcctg ggtgttttc    3120 tttctcattc gaatctacca cagttggtca tatccaaccc tcattcagta tttctatcaa    3180
gaaagagatg ctacaaaaaa aaaagaaaa aacctttatg tatacagacg taaacctcag    3240
aatgtatgtt gagtccccac tgtcatctac caagacttgc accccctca ttatctacca    3300 tgactgtctc tcagcctcac gggccctcag cactttgtgt tttgaccccc agcaccgtgt    3360
cttgtgaact cccatcacct tcaagaaagc ttccgaggta agaattttat ggtcatctgg    3420
gacaacttaa atctcccttc tgctgtcata gttcttccaa ctcagttgcc ttttttttt    3480 tttcgtactc atcactgact tgaagcttag tatctggctt ccttaaggat gtaactttca    3540
tgtaacagat taataactta tatgaaaacc aacacaacca tatgtttagg gctggaaagg    3600
gccatgacgc ctggccattt ttcctgtttt accttactct tatgtgtgtc acacttcatc    3660
aattccggaa acagtttctg gagatctcct cattacctct tttacaatca cctcactcca    3720
gcatggtgtc tgttacctct tcccacttgt gacaatgtct agtaaggtcc actctccatt    3780
ctgtgtgatg accacttatt acaaccctca gaataggga cagtggtgtg cccctgcaa    3840 tacaatggtt tctatctcct gatacttta ttacacctct agcaggatgt cttgtgatcc    3900
tccttattga tttttccctc acgatgatga acaattatct cccgttactc acctagcagt    3960
atctaactgt ccctaacaca gcatgtggga atgccctcaa tacggtggat gctgttaact    4020
ttcttccttc ccctcaggca atggcggtga cttacaatga accataatgt ccacatttcc    4080
caactgtatt ttggagcctc ttctgtcccc ttctttctag gaccccagtt aaaaaaaaaa    4140
aaaa                                                                  4144

<210> SEQ ID NO 21
<211> LENGTH: 1642
<212> TYPE: DNA
<213> ORGANISM: Homo sapiens

<400> SEQUENCE: 21
acagagtagc tttgcaactg gctttgggga cttccgaaag ctaccagcac tgcactgtga      60
gactctcatc cctgagctga attcatctga ttcgacggca agctttggtg agaaacataga    120 tatatttctg aggaaaatgg actcagactt ctcacatgcc ttccagaagg aactcacctg     180
cgtcatctgt ttgaactacc tggtagaccc tgtcaccatc tgctgtgggc acagcttctg     240
taggccctgt ctctgccttt cgtgggagga agcccaaagt cctgcaaact gccctgcatg     300
cagggaacca tcaccgaaaa tggacttcaa aaccaatatt cttctgaaga atttagtgac     360
cattgccaga aaagccagtc tctggcaatt cctgagctct gagaaacaaa tatgtgggac     420
ccataggcaa acaaagaaga tgttctgtga catggacaag agtctcctct gcttgctgtg     480
ctccaactct caggagcacg gggctcacaa acaccatccc atcgaagagg cagctgagga    540
acaccgggag aaactcttaa agcaaatgag gattttatgg aaaaagattc aagaaaatca     600
gagaaatcta tatgaggagg gaagaacagc cttcctctgg aggggcaatg tggttttacg    660
ggcacagatg atcaggaatg agtataggaa gctgcatccg gttctccata aggaagaaaa     720
acaacattta gagagactga acaaggaata ccaagagatt tttcagcaac tccagagaag    780
ttgggtcaaa atggatcaaa agagtaaaca cttgaaagaa atgtatcagg aactaatgga    840
aatgtgtcat aaaccagatg tggagctgct ccaggatttg ggagacatcg tggcaaggag    900
```

```
tgagtccgtg ctgctgcaca tgccccagcc tgtgaatcca gagctcactg caggacccat    960
cactggactg gtgtacaggc tcaaccgctt ccgagtggaa atttccttcc attttgaagt   1020
aaccaatcac aatatcaggc tctttgagga tgtgagaagt tggatgttta gacgtggacc   1080
tttgaattct gacagatctg actattttgc tgcatgggga gccagggtct tctcctttgg   1140
gaaacactac tgggagctgg atgtggacaa ctcttgtgac tgggctctgg gagtctgtaa   1200
caactcctgg ataaggaaga atagcacaat ggttaactct gaggacatat tcttctttt    1260
gtgtctgaag gtggataatc atttcaatct cttgaccacc tccccagtgt ttcctcacta   1320
catagagaaa cctctgggcc gggttggtgt gtttcttgat tttgaaagtg aagtgtgag    1380
tttttttgaat gtcaccaaga gttccctcat atggagttac ccagctggct ccttaacttt   1440
tcctgtcagg cctttctttt acactggcca cagatgatca ggattaagaa aacttactgt   1500
ttgggaactc catatacaag ggagcccttc actgttgata caaagaaatc atactgttca   1560
ggcttttttg tactttagtg tcacttcatt ttattgctat taaataaaaa atttgtaaaa   1620
ggcaaaaaaa aaaaaaaaaa aa                                            1642

<210> SEQ ID NO 22
<211> LENGTH: 5030
<212> TYPE: DNA
<213> ORGANISM: Homo sapiens

<400> SEQUENCE: 22
agtggagggg aggggtaag tgatagggta ggggaggccc tgggaaaggc aggacctcga      60
ggcgcggccg cgcgaggtga ccggagtcac agttcccgca ggcggcgaca gcagagcgcc    120
cactgcctcc agcaggtaac cggccgcggc cgcgcgcgc cggcccagcg cgggcgtggg    180
acgtggagac ccggaggagg gcggcgggac ccgggcgggg aaaggcgcgg cgtggcttgg   240
ctcaggtgcg cttctcccac ctggcagctc gctcagggct gtgggggggcg cctgtgaggg   300
cggccccgcc ttgcgggctg gagattaata ttaagattgg aagtttgtgt cttttgctgg   360
atattggaaa ttgaatgtaa tggcaacaga atttataaag agttgctgtg gaggatgttt   420
ctatggtgaa acagaaaaac acaacttttc tgtggaaaga gattttaaag cagcagtccc   480
aaatagtcaa aatgctacta tctctgtacc tccattgact tctgtttctg taaagcctca   540
gcttggctgt actgaggatt atttgctttc caaattacca tctgatggca agaagtacc    600
atttgtggtg cccaagtta agttatctta cattcaaccc aggacacaag aaactccttc    660
acatctggaa gaacttgaag gatctgccag agcatctttt ggagatcgaa aggtagaact   720
ttccagttca tcccagcacg gacctagcta tgatgtgtat aacccattct atatgtatca   780
gcacatttca cctgatttga gtcgacgctt tcctcccgt tcagaagtga cgagactgta    840
tggatcggtt tgtgatttaa ggacgaacaa acttcccggt tcccctgggc taagcaaatc    900
tatgttgat cttacaaact catctcagcg attcatccag agacatgatt cattgtccag     960
tgtacccagt agttcttctt caaggaaaaa ttctcagggg agtaacagaa gcctggatac   1020
aattactcta tcaggagatg aaagggactt tgggagactg aatgtgaaat tgttttataa   1080
ttcttcagta gaacagatct ggatcacagt tttacagtgc agagatttaa gttggccctc   1140
tagttatgga gacactccta ctgtttctat aaaaggaata cttacattgc ccaaaccagt   1200
gcatttcaaa tcttcagcca aggaaggttc aacgctatt gaatttatgg aaacgtttgt    1260
atttgctatt aaacttcaaa atctacaaac tgtaagactt gtatttaaga ttcaaaccca   1320
```

-continued

```
gactcccagg aagaaaacca ttggagaatg ctcaatgtca ctcagaaccc ttagcacaca    1380
ggaaatggat tactctttgg atataacacc accttcaaaa atttctgttt gccatgcaga    1440
acttgaattg gggacttgtt ttcaagcagt aaatagcaga attcagttac aaattcttga    1500
ggcacggtac cttccaagct catcaacacc tctgactttg agttttttcg tgaaggtggg    1560
aatgtttagc tcgggagagt tgatttataa gaaaaagaca cgcttactga aggcctccaa    1620
tggaagagtc aagtggggag agactatgat ttttccactt atacagagtg aaaaagaaat    1680
tgtttttctc attaagcttt acagtcgaag ctctgtaaga agaaaacact ttgtgggcca    1740
gatttggata agtgaagaca gtaataacat tgaagcagtg aaccagtgga agagacagt     1800 aataaatcca gaaaaggttg ttatcaggtg gcacaaatta aatccatctt gaagacttca    1860
cacattaatt tggtgaagaa cttgacattc ttttagaaga cttatgattt caatttgcta    1920
ccaatgagaa gaggcaaatc aacaaatttg tcaatttatg ggggctataa ttatggtata    1980
taatgtatct gatagaaaat ttgataagaa aatgtaatga attttatcag atatccaaag    2040
taaaggaaat gttttaaaac tgcaacaaga gacacagaca gtaaaatcaa agtattatta    2100
ggatgactaa ataaattata aagtctgtga gaatatcaac catagatagt tctttctata    2160
ttatgttttt gcttttgtat tttaagcttt acttagatat tcaaaacctg gtatatcaag    2220
tctctgttag tactattggc atttagaaga ctttaccatt atttcagtgc taggcattat    2280
tgattaggtc ttggctccac tgtttacctc ttgctatgta ttttctcccg gtaaaaatga    2340
attgaaccat ttcaactatt ttctatattt ggagaaagtt tgtgccctgt gttttataat    2400
ttttttaccc ataagacatc acattatccc tttgtaagct acttatctcc aaaaaacttc    2460
agaaatagaa aactacattt tggcaggaat aattgaaaac accagaaggt tgaagtttaa    2520
ttggaaaccc agaatataca tactttgctg ttttcttccc tcaaatattt tactatttgt    2580
tttatttgga gttaaaataa gagtatcatc catatggtcc atcctaattc acagaattaa    2640
atgagcttaa atagaaaatt cagtatttta tgataatcac ttcgttttta gttttaaaa    2700 tttagattat tctataattt accgtgtttg agtattttct catttttttc ataaccatac    2760
ctgattatac tgtgtaacaa atattttcta ttgcagtttt ctttccagta cttattagaa    2820
ctcagtattt ggaaataatt tcagcttaat tgaccataag aactgtggcc aaaaagaaca    2880
gttttttgga gaggcagatg acattatacc tgattttaga aaatctcact ttattttgc     2940 taataagtag actaagtgct ctgtgttctc agtcttccct ttttttctgc ccccattctt    3000
actttgtccc aggcatgcag agaaagatgg tgatatttta ggccaggagt ataccttgct    3060
ataacctaag catgccttct ttattccagc tcctatgttc tgtgtatatc attaacattt    3120
tcccaaataa acacttaatt ctcttttccc taggtgccat ctcctcaagc tacaaaatgt    3180
ccacatctta tatcccctttt gcttctactg ctctgatttt gtggtaccag tactctctgc    3240
cactgaacat tttgaaatat ttttgtttta gatttgcaaa aaatgacata taggtcagta    3300
ctcacatgga tttttaagat aaatcacctg tgtgataata ttttgaatct gagacgaata    3360 caactttttaa aaattgtttt taaaaataga ctttttttttt tagagcagtt gtaggttaac    3420
agaaaaattg agaggaagat agagatttcc tttctcccct gacaaagccc tcaacagcct    3480
cccaggctat cagtatcctg caccacaatg gtacatttgt tacaatcaat gaacctactc    3540
tgaaacatca ttatcatcca aagttcatgg tttacattag agtcccctct tggtgttata    3600
catgctagag gacaaatata tgatgatatg tatgcatcat tataatatag tatagtttcg    3660
ctgccctaaa catcctctgc aaatgcaact attttaatgg gtaccaaaga agtaaatgta    3720
```

-continued

```
tttactggct tttagataat aaataacggg ctttattgtt tattttaaaa gctacaattt    3780
gttttagctg gtttctctgt tctattaatg ctttgaattt ccaaatttaa tatatgtagt    3840
catgcattta acttaatatt taattatttg atttatttaa ttttctatat tcttacaatg    3900
tatgtatgat gtataattta agggaaagct atgacttctc agtttcttag aatcctaggt    3960
aaataaaaca ataaaagaa aacccttaca tttaaaagag ctttcaggta cagaagtatt     4020
gatacaacta agatcctaaa tgttttaatt agtgtttact taagccttt tcaggtgagg     4080 aggtactaat gctggttatt tccttgaagc tttatgtgga cctataaata aaaatccaat    4140
ctcctgctaa taggtatgca tattgtgaga aaaacgttag gagctggtag taaaaaatga    4200
gattctatgc caaataact tctcttcata tttgcctagg catttcttga cctttaccca     4260
cttacgcaag gagaaggaaa tcataatgat gtcatgtgat caaggaaaac catggaaggg    4320
ttcacgctga tagctgatag cttttacagt gctcattcct aacagtggat ttacttgtaa    4380
gctttcagat caacacaaat agctgcagcc tgggttaaaa tataacatca ctatttggct    4440
tttgttttgc atgattttta aaagcagtac tcctagggaa atggcctctg aagtatatca    4500
gtttcatctc ttaccaagac tgttaagaag aaactagtgg gattttgaac aagttatata    4560
attgtggtct gaaaagaccc taaactgaag ttctgtttaa atatagttac atgaatttct    4620
ctgatactaa tgtactcaac agccaggtat aaactatatc tcctagtaac attttccatt    4680
tttgtttaat caaatacttg cttatgaagg atttcagaaa tttgtaataa atgtcagctt    4740
ttgatagcat agcagtaatt gacatttcaa aaatatatat ttctttctgt gtttggttgg    4800
gtgtaatgag gaaaatacct gataaaatgt ctgaagacac tttctaatgt tatcttggtg    4860
cataagctgt aatttttatt caaaattaaa tttcaaatgt ttgcagtttt ggctaaaaca    4920
ttgagttgaa agaattatga aaagtgggcc catatgaagt accatgttca ttttgaaata    4980
tagatttaag atttagaaat atattaaaag agttaatgga gcctcctaaa                5030
```

<210> SEQ ID NO 23
<211> LENGTH: 2164
<212> TYPE: DNA
<213> ORGANISM: Homo sapiens

<400> SEQUENCE: 23

```
acccacagca ctcattcctg gagctactgc ttggttccct gagaggtccc agaactctgc      60
aaagtgagtc cagcgctgag attttttcttg cagatctatc aggatgagca tccaggcccc    120
acccagactc ctggagctgg cagggcagag cctgctgaga gaccaggcct tgtccatctc     180
tgccatggag gagctgccca gggtgctcta tctcccactc ttcatggagg ccttccgcag    240
gagacacttc cagactctga cggtgatggt gcaggcctgg cccttcacct gcctccctct    300
gggatcactg atgaagacgc ttcatttgga gaccttaaaa gcattgctgg aagggcttca    360
tatgctgctt acacagaagg atcgccccag gaggtgaaaa cttcaagtgc tggatttgcg    420
ggatgttgat gagaatttct gggccagatg gcctggagcc tgggccctgt cctgcttccc    480
agagaccatg agtaagaggc agacagcaga ggactgtcca aggatgggag agcaccagcc    540
cttaaaggtg ttcatagaca tctgcctcaa ggaaatacc caggatgaat gcctgagata    600
cctctttcag tgggtttacc aaaggagagg tttagtacac ctgtgctgta gtaagctggt    660
caattatcta acgccgatta aacatctcag aaagtcattg aaaataatat acctgaatag    720
tattcaacag ctggaaattc gcaacatgtc ctggccacgt ctgataagaa agcttcgttg    780
```

```
ttacctgaag gagatgaaga atcttcgcaa actcgttttc tccaggtgcc atcattccat    840
gtcagataat gaactcgaag gacggttagt caccaaattc agctctgtgt tcctcaggct    900
ggaacacctc cagttgctta aaataaaatt gatcaccttc ttcagtgggc acctggaaca    960
gctgatcagg tgcctccaga acccttgga gaacttggaa ttaacttatg ctacctatt    1020
ggaagaagac atgaagtgtc tctcccagta cccaagcctc ggttacctaa agcatctgaa   1080
tctcagctac gtgctgctgt tccgcatcag tcttgaaccc ctcggagctc tgctagagaa   1140
aattgctgcc tctctcgaaa ccctcatctt ggagggctgt cagatccact actcccaact   1200
cagtgccatc ctgcctggcc tgagccactg ctcccagctc accaccttct actttggcag   1260
aaattgtatg tctatgggtg ccctgaagga cctgttgcgc cacaccagtg ggctgagcaa   1320
gttaagcctg gagacgtatc ctgcccctga ggagagtttg aattccttgg ttcgtgtcga   1380
ttgggagatc ttcgccctac ttcgggctga gctgatgtgt acactgaggg aagtcaggca   1440
gcccaagagg atcttcattg gtcccacccc ctgcccttcc tgtggctcat caccgtctga   1500
ggaactggag ctccatcttt gctgctaggg aaggcgtgcc tagcggggta gagaaatcca   1560
aagttctctt ccaggcactg ggacactaaa atctactatg taggtgcaaa ctattttct   1620
cttttcttat ttatttcatt ttttaataat tccaaaattt ttattaaaga caatttgaga   1680
cagggtttct ctgtgttgct ctgggatcct cctgcctcag ctgggcttat gggatcctcc   1740
tgcctcagct tcctaaagtg ctgggattac tggcatgagt gactgtgtcc aggccacatg   1800
caacttaaag gaagcacagg gaagtgctca gtgtgaggga aaaaacata acagcagggg   1860
gcaaggctgg aggaaaatgt tgaggtgaca tcaatgagaa cttcagggac ccgtgtccta   1920
cagagtcgga aagagaagct aaagttctac agtgatgaga atgttatccc tgcaaggatg   1980
gttaccaagg aatatcagaa ataaagagca cctgaatgaa aacttttaac ctgttgtagc   2040
aatttatcca ccagaaatat ctagttattg agttactgat ggaaaaataa tgaaatacta   2100
ctttgtctgt gattgagttt cagctgtaga acatcaaagc aaccaaatag aatttgatca   2160
tttt                                                                2164

<210> SEQ ID NO 24
<211> LENGTH: 1642
<212> TYPE: DNA
<213> ORGANISM: Homo sapiens

<400> SEQUENCE: 24
cctgaagcta ctggttggtt ccctgagagg tcccagaact ctgcaaagtg agtccagcgc     60
tgagattttt cttgcagatc catcaggatg agcatccagg cccaccgag actactggag    120
ctggcgggc agagcctgct gagagaccag gccttgtcca tctctgccat ggaggagctg    180
cccagggtgc tctatctccc actcttcagg gaggccttca gcaggagaca cttccagact    240
ctgacggtga tggtgcaggc ctggcctttc acctgcctcc ctctggtatc gctgatgaag    300
acgcttcatc tggagccatt gaaagcattg ctggaagggc ttcatatgct gcttacacag    360
aaggatcgcc ccaggaggtg gaaacttcaa gtgctggatt gcgggatgt tgatgagaat    420
ttctgggcca gatggcctgg agcctgggcc tgtcctgct tcccagaggc catgagtaag    480
aggcagacag cagaggactg tccaaggacg ggagagcacc agcccttaaa ggtgttcata    540
gacatctgcc tcaaggaaat accccaggat gaatgcctga tacctcttcc agtggggtt    600
taccaaagga gaggtttagt acacctgtgc tgtagtaagc tggtcaatta tctaacgcca    660
attaaatatc tcagaaagtc attgaaaata atatacatta atagtattgg ggagctggaa    720
```

```
attcacaaca cgtgctggcc acatctgata agaaagcttt attgttacct gaaggagatg      780
aagactcttt gcaaactcgt tttctccagg tgccatcatt acacgtcaga taatgaactc      840
gagggatggt tagtcaccag attcacctct gtgttcctca ggctggaaca cctccagttg      900
cttaaaataa aattgatcac cttcttcagt gggcacctgg aacagctgat caggtgcctc      960
cagaacccct tggagaactt ggaattaact tgtggcaacc tattagaaga ggacttgaag     1020
tgtctctccc agttcccaag cctcggttac ctaaagcatc tgaatctcag ctacgtgctg     1080
ctgttccgca tcagtcttga accectagga gctctgctag agaaaattgc tgcctctctc     1140
gagaccctcg tgttagaggg ctgtcagatc cactactccc aactcagtgc catcctgcct     1200
ggcctgagct gctgctccca gctcaccacc ttctactttg cagcaattg catgtctatt      1260 gacgccctga aggacctgct cgccacacc agtgggctga gcaagttaag cctggagacg      1320
tatcctgccc ctgaggagag tttgaattcc ttggttcgtg tcaattggga gatcttcacc     1380
ccacttcggg ctgagctgat gtgtacactg agggaattca gcagcccaa gaggatcttc      1440 attggcccca ccecctgccc ttcctgtggc tcatcaccgt ctgaggaact ggagctccat     1500
ctttgctgct agggaaggcg tgcccagtgg ggtagagaaa tccaaagttc tcttccaggc     1560
acttggacac taaaatctac tatgtaggtg caaactattt ttctcttttc ttatttattt     1620
cattttttaa taattccaaa at                                              1642

<210> SEQ ID NO 25
<211> LENGTH: 4167
<212> TYPE: DNA
<213> ORGANISM: Homo sapiens

<400> SEQUENCE: 25
accttcgcca tatatacccg ggcgctgcg ctccacctgg ccgccgcctc cagcccagca        60
cctgcggagg gagcgctgac catggctccc tggcctgaat tgggagatgc ccagcccaac      120
cccgataagt acctcgaagg ggccgcaggt cagcagccca ctgcccctga taaaagcaaa      180
gagaccaaca aaacagataa cactgaggca cctgtaacca agattgaact tctgccgtcc      240
tactccacgg ctacactgat agatgagccc actgaggtgg atgaccctg gaacctaccc      300 actcttcagg actcggggat caagtggtca gagagagaca ccaaagggaa gattctctgt     360
ttcttccaag ggattgggag attgatttta cttctcggat ttctctactt tttcgtgtgc     420
tccctggata ttcttagtag cgccttccag ctggttggag aaaaatggc aggacagttc      480 ttcagcaaca gctctattat gtccaaccct tgttggggc tggtgatcgg ggtgctggtg     540
accgtcttgg tgcagagctc cagcacctca acgtccatcg ttgtcagcat ggtgtcctct     600
tcattgctca ctgttcgggc tgccatcccc attatcatgg gggccaacat ggaacgtca      660 atcaccaaca ctattgttgc gctcatgcag gtgggagatc ggagtgagtt cagaagagct      720
tttgcaggag ccactgtcca tgacttcttc aactggctgt ccgtgttggt gctcttgccc      780
gtggaggtgg ccacccatta cctcgagatc ataacccagc ttatagtgga gagcttccac     840
ttcaagaatg gagaagatgc cccagatctt ctgaaagtca tcactaagcc cttcacaaag     900
ctcattgtcc agctggataa aaagttatc agccaaattg caatgaacga tgaaaaagcg     960
aaaacaagac gtcttgtcaa gatttggtgc aaaactttta ccaacaagac ccagattaac     1020
gtcactgttc cctcgactgc taactgcacc tcccctttcc ctctgttgac ggatggcatc     1080
caaaactgga ccatgaagaa tgtgacctac aaggagaaca tcgccaaatg ccagcatatc     1140
```

```
tttgtgaatt tccacctccc ggatcttgct gtgggcacca tcttgctcat actctccctg    1200
ctggtcctct gtggttgcct gatcatgatt gtcaagatcc tgggctctgt gctcaagggg    1260
caggtcgcca ctgtcatcaa gaagaccatc aacactgatt tccccttcc ctttgcatgg     1320
ttgactggct acctgccat cctcgtcggg gcaggcatga ccttcatcgt acagagcagc    1380
tctgtgttca cgtcggcctt gaccccctg attggaatcg gcgtgataac cattgagagg    1440
gcttatccac tcacgctggg ctccaacatc ggcaccacca ccaccgccat cctgccgcc    1500
ttagccagcc ctggcaatgc attgaggagt tcactccaga tcgccctgtg ccactttttc    1560
ttcaacatct ccggcatctt gctgtggtac ccgatcccgt tcactcgcct gcccatccgc    1620
atggccaagg gctgggcaa catctctgcc aagtatcgct ggttcgccgt cttctacctg     1680
atcatcttct tcttcctgat cccgctgacg gtgtttggcc tctcgctggc cggctggcgg    1740
gtgctggttg gtgtcggggt tcccgtcgtc ttcatcatca tcctggtact gtgcctccga    1800
ctcctgcagt ctcgctgccc acgcgtcctg ccgaagaaac tccagaactg gaacttcctg    1860
ccgctgtgga tgcgctcgct gaagcccctgg gatgccgtcg tctccaagtt caccggctgc    1920
ttccagatgc gctgctgctg ctgctgccgc gtgtgctgcc gcgcgtgctg cttgctgtgt    1980
ggctgccccca agtgctgccg ctgcagcaag tgctgcgagg acttggagga ggcgcaggag    2040
gggcaggatg tccctgtcaa ggctcctgag acctttgata acataaccat tagcagagag    2100
gctcagggtg aggtccctgc ctcggactca aagaccgaat gcacggcctt gtaggggacg    2160
ccccagattg tcagggatgg ggggatggtc cttgagtttt gcatgctctc ctccctccca    2220
cttctgcacc ctttcaccac ctcgaggaga tttgctcccc attagcgaat gaaattgatg    2280
cagtcctacc taactcgatt cccttttggct tggtggtagg cctgcagggc acttttattc    2340
caaccctgg tcactcagta atcttttact ccaggaaggc acaggatggt acctaaagag    2400
aattagagaa tgaacctggc gggacggatg tctaatcctg cgcctagctg ggttggtcag    2460
tagaacctat tttcagactc aaaaaccatc ttcagaaaga aaaggcccag ggaaggaatg    2520
tatgagaggc tctcccagat gaggaagtgt actctctatg actatcaagc tcaggcctct    2580
cccttttttt aaaccaaagt ctggcaacca agagcagcag ctccatggcc tccttgcccc    2640
agatcagcct gggtcagggg acatagtgtc attgtttgga aactgcagac cacaaggtgt    2700
gggtctatcc cacttcctag tgctccccac attccccatc agggcttcct cacgtggaca    2760
ggtgtgctag tccaggcagt tcacttgcag tttccttgtc ctcatgcttc ggggatggga    2820
gccacgcctg aactagagtt caggctggat acatgtgctc acctgctgct cttgtcttcc    2880
taagagacag agagtggggc agatggagga gaagaaagtg aggaatgagt agcatagcat    2940
tctgccaaaa gggccccaga ttcttaattt agcaaactaa gaagcccaat tcaaaagcat    3000
tgtggctaaa gtctaacgct cctctcttgg tcagataaca aaagccctcc ctgttggatc    3060
ttttgaaata aaacgtgcaa gttatccagg ctcgtagcct gcatgctgcc accttgaatc    3120
ccagggagta tctgcacctg gaatagctct ccacccctct ctgcctcctt actttctgtg    3180
caagatgact tcctgggtta acttccttct ttccatccac ccaccactg gaatctcttt    3240
ccaaacattt ttccattttc ccacagatgg gctttgatta gctgtcctct ctccatgcct    3300
gcaaagctcc agattttttgg ggaaagctgt acccaactgg actgcccagt gaactgggat    3360
cattaagtac agtcgagcac acgtgtgtgc atgggtcaaa ggggtgtgtt ccttctcatc    3420
ctagatgcct tctctgtgcc ttccacagcc tcctgcctga ttacaccact gccccgccc     3480
cacccctcagc catcccaatt cttcctggcc agtgcgctcc agccttatct aggaaaggag    3540
```

-continued

| | |
|---|---|
| gagtgggtgt agccgtgcag caagattggg gcctcccca tcccagcttc tccaccatcc | 3600 |
| cagcaagtca ggatatcaga cagtcctccc ctgaccctcc cccttgtaga tatcaattcc | 3660 |
| caaacagagc caaatactct atatctatag tcacagccct gtacagcatt tttcataagt | 3720 |
| tatatagtaa atggtctgca tgatttgtgc ttctagtgct ctcatttgga aatgaggcag | 3780 |
| gcttcttcta tgaaatgtaa agaaagaaac cactttgtat attttgtaat accacctctg | 3840 |
| tggccatgcc tgccccgccc actctgtata tatgtaagtt aaacccgggc aggggctgtg | 3900 |
| gccgtctttg tactctggtg attttaaaa attgaatctt tgtacttgca ttgattgtat | 3960 |
| aataattttg agaccaggtc tcgctgtgtt gctcaggctg gtctcaaact cctgagatca | 4020 |
| agcaatccgc ccacctcagc ctcccaaagt gctgagatca caggcgtgag ccaccaccag | 4080 |
| gcctgattgt aatttttttt ttttttttt tactggttat gggaagggag aaataaaatc | 4140 |
| atcaaaccca aaaaaaaaa aaaaaaa | 4167 |

<210> SEQ ID NO 26
<211> LENGTH: 2664
<212> TYPE: DNA
<213> ORGANISM: Homo sapiens

<400> SEQUENCE: 26

| | |
|---|---|
| agagccagcc cggaggagct agaaccttcc ccgcatttct ttcagcagcc tgagtcagag | 60 |
| gcgggctggc ctggcgtagc cgcccagcct cgcggctcat gccccgatct gcccgaacct | 120 |
| tctcccgggg tcagcgccgc gccgcgccac ccggctgagt cagcccgggc gggcgagagg | 180 |
| ctctcaactg ggcgggaagg tgcgggaagg tgcggaaagg ttcgcgaaag ttcgcggcgg | 240 |
| cgggggtcgg gtgaggcgca aaaggataaa aagcccgtgg aagcggagct gagcagatcc | 300 |
| gagccgggct ggctgcagag aaaccgcagg gagagcctca ctgctgagcg cccctcgacg | 360 |
| gcggagcggc agcagcctcc gtggcctcca gcatccgaca agaagcttca gccatgcagg | 420 |
| ccccacggga gctcgcggtg ggcatcgacc tgggcaccac ctactcgtgc gtgggcgtgt | 480 |
| ttcagcaggg ccgcgtggag atcctggcca acgaccaggg caaccgcacc acgcccagct | 540 |
| acgtggcctt caccgacacc gagcggctgg tcggggacgc ggccaagagc caggcggccc | 600 |
| tgaaccccca caacaccgtg ttcgatgcca agcggctgat cgggcgcaag ttcgcggaca | 660 |
| ccacggtgca gtcggacatg aagcactggc ccttccgggt ggtgagcgag ggcggcaagc | 720 |
| ccaaggtgcg cgtatgctac cgcggggagg acaagacgtt ctaccccgag gagatctcgt | 780 |
| ccatggtgct gagcaagatg aaggagacgc cgaggcgta cctgggccag cccgtgaagc | 840 |
| acgcagtgat caccgtgccc gcctatttca atgactcgca gcgccaggcc accaaggacg | 900 |
| cgggggccat cgcggggctc aacgtgttgc ggatcatcaa tgagcccacg gcagctgcca | 960 |
| tcgcctatgg gctggaccgg cggggcgcgg agagcgcaa cgtgctcatt tttgacctgg | 1020 |
| gtggggcac cttcgatgtg tcggttctct ccattgacgc tggtgtcttt gaggtgaaag | 1080 |
| ccactgctgg agatacccac ctgggaggag aggacttcga caaccggctc gtgaaccact | 1140 |
| tcatggaaga attccggcgg aagcatggga aggacctgag cgggaacaag cgtgccctgc | 1200 |
| gcaggctgcg cacagcctgt gagcgcgcca agcgcaccct gtcctccagc acccaggcca | 1260 |
| ccctggagat agactccctg ttcgagggcg tggacttcta cacgtccatc actcgtgccc | 1320 |
| gctttgagga actgtgctca gacctcttcc gcagcaccct ggagccggtg gagaaggccc | 1380 |
| tgcgggatgc caagctggac aaggcccaga ttcatgacgt cgtcctggtg gggggctcca | 1440 |

| | |
|---|---|
| ctcgcatccc caaggtgcag aagttgctgc aggacttctt caacggcaag gagctgaaca | 1500 |
| agagcatcaa ccctgatgag gctgtggcct atggggctgc tgtgcaggcg gccgtgttga | 1560 |
| tgggggacaa atgtgagaaa gtgcaggatc tcctgctgct ggatgtggct cccctgtctc | 1620 |
| tggggctgga gacagcaggt gggggtgatga ccacgctgat ccagaggaac gccactatcc | 1680 |
| ccaccaagca gacccagact ttcaccacct actcggacaa ccagcctggg gtcttcatcc | 1740 |
| aggtgtatga gggtgagagg gccatgacca aggacaacaa cctgctgggg cgttttgaac | 1800 |
| tcagtggcat ccctcctgcc ccacgtggag tcccccagat agaggtgacc tttgacattg | 1860 |
| atgctaatgg catcctgagc gtgacagcca ctgacaggag cacaggtaag gctaacaaga | 1920 |
| tcaccatcac caatgacaag ggccggctga gcaaggagga ggtggagagg atggttcatg | 1980 |
| aagccgagca gtacaaggct gaggatgagg cccagaggga cagagtggct gccaaaaact | 2040 |
| cgctggaggc ccatgtcttc catgtgaaag gttctttgca agaggaaagc cttagggaca | 2100 |
| agattcccga agaggacagg cgcaaaatgc aagacaagtg tcgggaagtc cttgcctggc | 2160 |
| tggagcacaa ccagctggca gagaaggagg agtatgagca tcagaagagg gagctggagc | 2220 |
| aaatctgtcg ccccatcttc tccaggctct atggggggcc tggtgtccct ggggggcagca | 2280 |
| gttgtggcac tcaagcccgc caggggggacc ccagcaccgg ccccatcatt gaggaggttg | 2340 |
| attgaatggc ccttcgtgat aagtcagctg tgactgtcag ggctatgcta tgggccttct | 2400 |
| agactgtctt ctatgatcct gcccttcaga gatgaacttt ccctccaaag ctagaacttt | 2460 |
| cttcccagga taactgaagt cttttgactt tttgggggga gggcggttca tcctcttctg | 2520 |
| cttcaaataa aaagtcatta atttattaaa acttgtgtgg cactttaaca ttgctttcac | 2580 |
| ctatattttg tgtactttgt tacttgcatg tatgaatttt gttatgtaaa atatagttat | 2640 |
| agacctaaat aaaaaaaaaa aaaa | 2664 |

<210> SEQ ID NO 27
<211> LENGTH: 2163
<212> TYPE: DNA
<213> ORGANISM: Homo sapiens

<400> SEQUENCE: 27

| | |
|---|---|
| ctaatcttcc agttgccccc tattgacttt aaaccaaagc tttgattcat gaccactggg | 60 |
| atccagccag cggggggattt cttttcctga tggactgtac ccaggatctc acatttgctt | 120 |
| aagcagctcc cacaattggg ttcttataaa aggacacgga agagacaagc tcagttttct | 180 |
| ctgaaggaga aggactgcac ttagaactgc attttggcga cctctgaaat tcagtactgc | 240 |
| agtgaatgag cttctgatct tgaggtgaac ttaacaaaat tattttttgga aaaatcgttg | 300 |
| tgggaaccat taaagaact ccaggaaaca tgaattctgg aatcttacag gtctttcagg | 360 |
| gggaactcat ctgccccctg tgcatgaact acttcataga cccggtcacc atagactgtg | 420 |
| ggcacagctt ttgcaggcct tgtttctacc tcaactggca agacatccca tttcttgtcc | 480 |
| agtgctctga atgcacaaag tcaaccgagc agataaacct caaaaccaac attcatttga | 540 |
| agaagatggc ttctcttgcc agaaaagtca gtctctggct attcctgagc tctgaggagc | 600 |
| aaatgtgtgg cactcacagg gagacaaaga agatattctg tgaagtggac aggagcctgc | 660 |
| tctgtttgct gtgctccagc tctcaggagc accggtatca cagacaccgt cccattgagt | 720 |
| gggctgctga ggaacaccgg gagaagcttt tacagaaaat gcagtctttg tgggaaaaag | 780 |
| cttgtgaaaa tcacagaaac ctgaatgtgg aaaccaccag aaccagatgc tggaaggatt | 840 |
| atgtgaattt aaggctagaa gcaattagag ctgagtatca gaagatgcct gcatttcatc | 900 |

```
atgaagaaga aaaacataat ttggagatgc tgaaaaagaa ggggaaagaa atttttcatc      960
gacttcattt aagtaaagcc aaaatggctc ataggatgga gattttaaga ggaatgtatg     1020
aggagctgaa cgaaatgtgc cataaaccag atgtggagct acttcaggct tttggagaca     1080
tattacacag gagtgagtcc gtgctgctgc acatgcccca gcctctgaat ccagagctca     1140
gtgcagggcc catcactgga ctgagggaca ggctcaacca attccgagtg catattactc     1200
tgcatcatga agaagccaac aatgatatct ttctgtatga aattttgaga agcatgtgta     1260
ttggatgtga ccatcaagat gtaccctatt tcactgcaac acctagaagt tttcttgcat     1320
ggggtgttca gactttcacc tcgggcaaat attactggga ggtccatgta ggggactcct     1380
ggaattgggc ttttggtgtc tgtaatatgt atcggaaaga gaagaatcag aatgagaaga     1440
tagatggaaa ggcgggactc tttcttcttg ggtgtgttaa gaatgacatt caatgcagtc     1500
tctttaccac ctccccactt atgctgcaat atcccaaa acctaccagc cgagtaggat      1560
tattcctgga ttgtgaggct aagactgtga gctttgttga tgttaatcaa agctccctaa     1620
tatacaccat ccctaattgc tctttctcac ctcctctcag gcctatcttt gctgtattc      1680 acttctgacc agagacaaat cagaaatgtg ttcacatgct gtgggaaccc ctttatccca     1740
ggaagtcctc ttccttgtgc cttaacatac aggacaaata ggctctattt tatgtcttga     1800
attgccttct aatgttatca aaactcattt attgtgttac tattaaatat gctgaaaacg     1860
ctaaaagtat acgtattggt tctttattaa ataattttg aaaaatcatt attcatgatc      1920
atggcataca gtatattctc tttttttct ttatttatga ctgtcactga gtgaaataat      1980
agatgacaga catgtctgaa tgaagtaaaa atcaatggaa gacagtcggg atcttttgct     2040
tcatgcaaaa aacttggagt gaagtctcaa tgataactgg gaaatgtttt tcttcctctt     2100
tatctaacta tattacactt atccatcagg tttcattgta ttaatctatc ctttgaggta     2160
ata                                                                   2163
```

<210> SEQ ID NO 28
<211> LENGTH: 2160
<212> TYPE: DNA
<213> ORGANISM: Homo sapiens

<400> SEQUENCE: 28

```
acccacagca ctcattcctg aagctactgg ttggttccct gagaggtccc agaactctgc       60
gaagtgagtc cagcgctgag attttccttg cagatctatc aggatgagca tccaggcccc      120
acccagacta ctggagctgg cagggcagag cctgctgaga gaccaggcct tgtccatctc      180
tgccatggag gagctgccca gggtgctcta tctcccactc ttcatggagg ccttcagcag      240
gagacacttc cagactctga cggtgatggt tcaggcctgg cccttcacct gcctccctct      300
gggatcactg atgaagacgc ttcatttgga gaccttaaaa gcattgctgg aagggcttca      360
tatgctgctt acacagaagg atcgccccag gaggtgaaa cttcaagtgc tggatttgcg       420
ggatgttgac gagaatttct ggccagatg gcctggagcc tgggccctgt cctgcttccc      480
agagaccacg agtaagaggc agacagcaga ggactgtcca aggatgggag agcaccagcc      540
cttaaaggtg ttcatagaca tctgcctcaa ggaaataccc caggatgaat gcctgagata      600
cctcttccag tgggtttacc aaaggagagg tttagtacac ctgtgctgta gtaagctggt      660
caattatcta acgccgatta aatatctcag aaagtcattg aaaataatat acctgaaatag     720 tattcaagag ctggaaattc gcaacatgtc ctggccacgt ctgataagaa agcttcgttg      780
```

| | |
|---|---|
| ttacctgaag gagatgaaga atcttcgcaa actcgttttc tccaggtgcc atcattacac | 840 |
| gtcagataat gaactccaag gacggttagt tgccaaattc agctctgtgt tcctcaggct | 900 |
| ggaacacctt cagttgctta aaataaaatt gatcaccttc ttcagtgggc acctggaaca | 960 |
| gctgatcagg tgcctccaga acccettgga gaacttggaa ttaacttatg ctacctatt | 1020 |
| ggaagaagac atgaagtgtc tctcccagta cccaagcctc ggttacctaa agcatctgaa | 1080 |
| tctcagctac gtgctgctgt tccgcatcag tcttgaaccc ctcggagctc tgctggagaa | 1140 |
| aattgctgcc tctctcaaaa ccctcatctt ggagggctgt cagatccact actcccaact | 1200 |
| cagtgccatc ctgcctgccc tgagccggtg ctcccagctc accaccttct actttggcag | 1260 |
| aaattgcatg tctattgacg ccctgaagga cctgctgcgc cacaccagtg ggctgagcaa | 1320 |
| gttaagcctg gagacgtatc ctgcccctga ggagagtttg aattccttgg ttcgtgtcaa | 1380 |
| tgggagatc ttcaccccac ttcgggctga gctgatgtgt acactgaggg aagtcaggca | 1440 |
| gcccaagagg atcttcattg gccccacccc ctgcccttcc tgtggctcat caccgtctga | 1500 |
| ggaactggag ctccatcttt gctgctaggg aaggcgtgcc cagtggggta gagaaatcca | 1560 |
| aagttctctt ccaggcactt ggacactaaa atctactatg tgggtgcaaa ctattttct | 1620 |
| cttttcttat ttatttcatt ttttaataat tccaaaattt ttattaaaga caatttgaga | 1680 |
| cagggtttcg ctgtgttgct ccagctggtc tcaaactgct gggcttatgg gatcctcctg | 1740 |
| cctcagcttc ctaaagtgct gggattactg catgagtga ctgtgtccag gccacatgca | 1800 |
| acttaaagga agcacaggca agtgttcagt gtgagggaaa aaacataaca gcaggggca | 1860 |
| aggttggagg aaaatgttga ggtgacatca gtgagaactt cagggacccg tgtcctagag | 1920 |
| tcggaaagag aagctaaagt tctacagtga tgagactgtt atccctgcaa ggatggttac | 1980 |
| caaggaatat cagcaataaa gagcacctga atgaaaactt ttaacctgtt gtgcaattta | 2040 |
| tccatcagaa atctctagtt atcgagttac ggatggaaaa ataacgaaat actaatttgt | 2100 |
| ctgtgattga gtttcagttg tagaacatca aagcaaccaa ataaaaatta gatcattttg | 2160 |

<210> SEQ ID NO 29
<211> LENGTH: 5937
<212> TYPE: DNA
<213> ORGANISM: Homo sapiens

<400> SEQUENCE: 29

| | |
|---|---|
| tgcaggtaac aagggcaaca gcctgagcat ctcagagccc agaggcagag cgttagccga | 60 |
| ttgcttccag catcatctgg ggcacagtgg ggtcttggtt cctcaatggg cctgagtgga | 120 |
| tctaactctg cgaagttaga tcccaacagc catcacagtt tgcagacaat gtcattaaga | 180 |
| ccatccagat aacttcctaa ctccagtttt gtgcccacca agcatccttc tgatttcaaa | 240 |
| ttggcctcgc atgccatgtg caactgggag agagtgtgtg gacagaaatg gggccaattg | 300 |
| actatttccc ttggctgtca tatttttcat taataaacta actctccagc cacaaataca | 360 |
| cactcagaat gcctcttgct actccagatc ctccattcac tgtgaaggca atcatgggga | 420 |
| ttatgaattc catctcccag gtgtggatta aactgcatgc caggggaggt ttctgtggtt | 480 |
| ccaatctacc ccgcttagta catcagggct caacaggatc aggtcaaagc tggaaggatc | 540 |
| ctgagagccc acagaaataa tgactcctgt gctgaggttc acaggagtag cactgggtc | 600 |
| tgtgaattct tggcaaaaat tcagaaaacc taagggaatc catgcattag ctgataatga | 660 |
| ggccatacag actaactaaa gcatcagcca cctcattaaa ctgggaagct taatactgtt | 720 |
| tttattgcac aatcatttct aaatgtcttt tattaataaa attggggaaa tgaatttgtt | 780 |

```
attctttaat aagtgcagtg tgtttagctg acaaaatttt tacaaagatg gggatcaatg      840
ggttgcaaga atactaaaag atgttcttgt tctgcagggt tggaagcccc taagccacca      900
tgcactaccc atcattttac aaaagaagga gaaactgagg aacaaagaaa cacatatttt      960
ccctcaagct tcagattccc tttaaactct taggatatcc cataacccccc tgtagcttat     1020 ggcagctaga ttcatgacag acaatctctc tagagtcaat ttggttttttc tcttaactca     1080 ctcaagcctc tgggaatgaa aggtctagcc cttgaaggct acttttggta gaagacgagg      1140
ttcagtatta aaaggagga cagaggatgg aaaagaacac aactacatca atagtttctc       1200
cacattattt gatgttcaga acagtcccat gaagaagata taatattccc tttctacaga      1260
ccaaaaaatt aatatttgga gaggtagaaa gaccacccaa gggaacacat atttagacgg      1320
aaagcccagt tctgtctagt gtttaagtcc tggcccattc agctactctg ctctgtaact      1380
atcacccatt tcagcaccgc ggacagaggc agagccctca gtcttccctg taggtgggat      1440
ggaggcagag ggtggtaaga tgggtgctaa gtcccaggga agatatgtat ccaccaaagt      1500
gcctgaatga tgagagggaa gtcagagcta aggaaggaca catcatggac atctctttac      1560
atgtgtatca aattgcgttc tgtttagaac cattttctag cctcccacca aggacgtaaa      1620
caggacaagc actgtcatct gtaaagtgcc actcccagac tgccacccag agttcataaa      1680
aggctcagat gaatcaatag gtgggaaagt tatctgaat ttataaaaat tcactgttaa       1740
ggagacgact atcacagaca aaccccaaaa tcagcggttt aacacaatag acattttttc      1800
tgacttgtgt aaagcccag acagggatcg ctgcctgtca aaaggcctga ctggcacttg       1860
tcttgaggca cactctggtg cccaggcccc ttgctccttg ttgctctgcc acctctgaag      1920
tggcttctaa ggtcactgta tttatctgtg tcaagacaga ggaaaaaatc atgaataaat      1980
aaacccaggg agatttgtat gagccaagcc tgaaattggc acacatcact ttggctcata     2040
cgtggaggac tgggagtgca gaaagatgag gaaatgggtc ttactgaaca cagaaccaca     2100
gaactctgtc tccctcctct ccaaagctga gaaattgcca caatcagaaa gtgtgattcc     2160
catctgagag tttaagagca ggaatagatt aaagacaaat catgtaaaat accttgactc     2220
ctagacttgc cgaagcattc agcctgagcc atctttacat gtggataatc ttggatttcc     2280
caactgggct tcttgcacac tccatggtag aacgtcagag gaattttttt tcaagcaaga     2340
gctgttagat catgagattc cccagaaaga tacagataca ggtatatgtc atattactgg     2400
agattctaat tcagctacct tcacaggcct gggaatgtgt ttttgacaca ggggcattag     2460
gattgtttca gctgcaagtg acagaagtct agctcacacg gtcttaagca agaaaggaaa     2520
tgtattgatt cctataagtg caccaggatc tagatacact gtcaggcaca gctggatgca     2580
gactccaaca gtctcattgg gatacccacc ctctcctccc atctctgacc atcccaggtg     2640 gctccccttca tgggtcaaag tggccaccag aagctccaga tacatctttt tatcaacagc    2700
cccaggagaa cttctctttc tcagtaaaat cccacaaggt attttttggc actaattgtc     2760
ttggcttggt cccattctta tccctgaacc aaccactgtg accaaaaacg tggtattctc     2820
tgattatcca agcctgattc acgagcccac ccatgagtct gatatgaggt ccagtccata     2880
caatctacac aagctaggtc tggggcatgg tggtgcccca aggacagctg gggtgccttt     2940
cctagaagaa aggggcagg gaatgggtgc tggaccagca tcagcagcag aattcttagg     3000
cactagactg tgggggctc agagaggcat gggagccctg aggtccccac aaggtgtggg     3060
atagtctttc agaccttcag ggggggtctc tgctcactaa cctgctcaaa gcaccctggc    3120
```

```
ccacaccgtg ggcagctgga aggtgccagt ccactgaaca tgtgtgattg gcatgaatct    3180
cctgctttcc tttgtcagaa ggctaggagt ggatttgacc cgtttactca gaccctctca    3240
gtggccctgc tcccacaggc tcaccccagc agggcccagt gcttggctgc caatgacgcc    3300
aaggatatta gctgacagtg acttaaaaca ggggttcatg acctcagggt aaccgaggaa    3360
cccctgaatc tgaattcatc agtctgtgta tatgaatgtg agtgcctctc ctttccccac    3420
aggaaaaaat ctacaacttt catcaaatta ctcagggaga ctttattcta aagagactga    3480
aaacgaccaa catcaatttt gactcctatg ggcatctgta aatagcttca aggttttaag    3540
gtgaaatgtc atgtaccaaa atacacattc tggagaagca ggaagctaca gaccaacttg    3600
agatgaaagt ctcatatcaa tgttttccca agtgtgctcc ttggaataca ggttgacatg    3660
atatgatgcc cagcaaggga aacaaaacat attcatgttc aaattagttg gggaaatgct    3720
ggactaaata aggtttgatg ggattctttt ttctgcagga cttctcagaa ggggctagag    3780
taggcaaagt ttcccagatt tacctaataa aagcattgtt tctgtgggag tttcatttgt    3840
tattacatgt ttcctgaatg cagattcata gactatcctt tggggaaccc tcgtcctcac    3900
gggatgtatg ttcatggtgg tgtcttcgag tttgtgccct tgtgaagcat tctggcagca    3960
agcgtctgaa cacttccaaa aggggcgat atttaggaga aatcgctcag cctgaattag    4020
aacaaatgca gctgctggtg tctcttggtg cctgggagcc ctagagtgtc agagggagga    4080
gcgtgcacac tggaaccagc agcctggtgc tgcgtctcag ctctgtcgct aactggctat    4140
gcacctctgg gcatggcact taaccctict gagccccagc ccgccatctg taaaaagggc    4200
ttgatgtgag gattgaatga gatcatgcag ggaacacaat gtctggcact tggaagcgtc    4260
caccataaag agccaaggca gtagatggcc cagctgggtt tgttccaggc agagtttacc    4320
ctctgccctg gaggctccag gaaatgctgc cacgtggctc ctattgcctt aaccacatcc    4380
gacctgttcc tgacagctcc ccacatctcc agctcctttg ctggtgctcc aggcacctcc    4440
aaacgtggcg agccctctc ccctgccctc ttgtggcagc tgacctggca ggagtgggac    4500
caagacatcc aaggcagctc ctttccacct gcatgggcac tttcctcagg acatccttgc    4560
ccctggcacc accttgggcc agcaagccac atggaaatgg atgcagaggc accactgttt    4620
gctgacaatt atacactgtc cttaaggtca cccttggcga tctgtcacca ggagcagaca    4680
aaccacaccc tcaaccatcc catcagagct tgtttctatc tgcatctgtc atcgctgatc    4740
gcatttgaat gggtttagtc tctatttaa ataaaagatt tatgccttag ctgtcagagc    4800
ctgcctttat ttgaaaattt aatcttgttt ctaggagtct agattaactt attagattta    4860
ggcgtccctc gtgggtctct gagagaggag gagtagattc tcctccctgc attcggccct    4920
gcacacccga cagtgagagc caagagctgg atgggcttct ccatccagca cgcccaggct    4980
ggacagaggc ccccaactca ggcaactttg tcgggtaacc gtgtgtccag ggagtgcttt    5040
cttgcacgct ccgtctccgg gccagcttcc aggacctgtg ctcactgcaa ggcacaccca    5100
tcgagccggc cctttctcag aggttttggg gaggcttcag gaaggacccc cagtgggggc    5160
ccagcttgtc aacatgggct gtgccaagga gttctgagtt tccttcaggt ctgtattgta    5220
tcttccaccc cctcagagct ccctccctac tgcttagacc acacgaagct gtggggctgt    5280
gggcagccag ttcacttccc tgaccttgtc tgcaggtgga gacagtggca gtgcccctcc    5340
cgggctgctg cgtcactcag tgtaaaagca gggaggcact ggagagctgc tgtctgcaag    5400
tttgttgcta cttcaaaagg tgcaggtggg ccctcacctc ctttagaggt gaggatgagc    5460
tacccaaagt gaaaaggagc ttctcagcgt cgcaatggag tcacggccag gctgcccaca    5520
```

```
ccagccgtcc ggacctgcac cagtgccacg gggtctgccc catcttctct tccctctcct    5580 tccctctctcc ctctctctcc ctgtctcttt ctcctctctc catgctattg actgaatgtt    5640
tgaattccct gcaaatgcat tcctaacccc caatgtgact gtgtttggag acagggtctt    5700
taggaggtaa ctgaggttaa atgaggttgt aaagatgggg ccctgaaccg atgggactgg    5760
ggtccttatg agaagaggaa aaggggtccc tccccatgga gggacgacca cagcgaggca    5820
gcagccgccc acacgccaga gaaggggact cagagggaag ccttgcttca ccggcacctt    5880
gatcttgact cctagcctcc agaattgtga taaataaatt tctgttgctt aagcccc       5937
```

<210> SEQ ID NO 30
<211> LENGTH: 2364
<212> TYPE: DNA
<213> ORGANISM: Homo sapiens

<400> SEQUENCE: 30

```
ctgctgaaaa agcagaaaga gattaccagc cacagacggg tcatgagcgc ggtattactg      60
ctggccctcc tggggttcat cctcccactg ccaggagtgc aggcgctgct ctgccagttt     120
gggacagttc agcatgtgtg gaaggtgtcc gacctgcccc ggcaatggac ccctaagaac     180
accagctgcg acagcggctt ggggtgccag gacacgttga tgctcattga gagcggaccc     240
caagtgagcc tggtgctctc caagggctgc acggaggcca aggaccagga gccccgcgtc     300
actgagcacc ggatgggccc cggcctctcc ctgatctcct acaccttcgt gtgccgccag     360
gaggacttct gcaacaacct cgttaactcc ctcccgcttt gggccccaca gccccccagca    420 gacccaggat ccttgaggtg cccagtctgc ttgtctatgg aaggctgtct ggaggggaca     480
acagaagaga tctgccccaa ggggaccaca cactgttatg atggcctcct caggctcagg     540
ggaggaggca tcttctccaa tctgagagtc cagggatgca tgccccagcc agtttgcaac     600
ctgctcaatg ggacacagga aattgggccc gtgggtatga ctgagaactg cgatatgaaa     660
gattttctga cctgtcatcg ggggaccacc attatgacac acggaaactt ggctcaagaa     720
cccactgatt ggaccacatc gaataccgag atgtgcgagg tggggcaggt gtgtcaggag     780
acgctgctgc tcctagatgt aggactcaca tcaaccctgg tggggacaaa aggctgcagc     840
actgttgggg ctcaaaattc ccagaagacc accatccact cagcccctcc tggggtgctt     900
gtggcctcct atacccactt ctgctcctcg gacctgtgca ataagtgccag cagcagcagc    960 gttctgctga actccctccc tcctcaagct gcccctgtcc caggagaccg gcagtgtcct    1020
acctgtgtgc agcccccttgg aacctgttca agtggctccc ccgaatgac ctgccccagg    1080 ggcgccactc attgttatga tgggtacatt catctctcag gaggtgggct gtccaccaaa    1140
atgagcattc agggctgcgt ggcccaacct tccagcttct tgttgaacca caccagacaa    1200
atcgggatct tctctgcgcg tgagaagcgt gatgtgcagc ctcctgcctc tcagcatgag    1260
ggaggtgggg ctgagggcct ggagtctctc acttgggggg tggggctggc actgccccca    1320
gcgctgtggt ggggagtggt ttgccctccc tgctaactct attaccccca cgattcttca    1380
ccgctgctga ccacccacac tcaacctccc tctgacctca taacctaatg gccttggaca    1440
ccagattctt tccccattctg tccatgaatc atcttcccca cacacaatca ttcatatcta    1500
ctcacctaac agcaacactg gggagagcct ggagcatccg gacttgccct atgggagagg    1560
ggacgctgga ggagtggctg catgtatctg ataatacaga ccctgtcctt tctcccagtg    1620
ctgggatttc tccatgtgag ggggcagcag gacacccagg gatctagcgt gggggaggag    1680
```

| | |
|---|---|
| aggagcctaa tgagaaaatg accatctaaa gcctgcccct cattggtctg gttcacgtct | 1740 |
| ccaaaccagc ttggatggta gcagagactt cagggtgctc cagccaaacg tatttgggca | 1800 |
| tcaccatgac ctgggagggg aagatgcact gagacgtatg aggcttccag cctagcagcc | 1860 |
| agggccctag cacaaacagg aggctcgccc catctgagca actgcaggag aggttagtac | 1920 |
| agtcatgcat tgcttaacga cagggacgtg tcgttagaaa tgtgtcgtta ggtgatttta | 1980 |
| tgaccatagg aacattgtag cgtgcactta caccaaccca gatggtacag cccaatacac | 2040 |
| acccaggatg gacgctagag tcgactgctc ctaggctaca agcctgcagt gcatgttatg | 2100 |
| gtgtgaatac tgcaggcaat cttaacacca cggcaagtat ttgtgcatct acacacatct | 2160 |
| aaacatagaa aaggtacagc ataaatacac tattgtcatc tcagcagacc accgttctat | 2220 |
| acgcaattcg tcgctgaccc aaacgttgct atgtagcatc tgcgtatcgt gggataattg | 2280 |
| acatgagggc ttgagagaac tccagaaaaa aatgggttag cattttccca gagctgttat | 2340 |
| cattgggtct ctcttaccac cata | 2364 |

<210> SEQ ID NO 31
<211> LENGTH: 1189
<212> TYPE: DNA
<213> ORGANISM: Homo sapiens

<400> SEQUENCE: 31

| | |
|---|---|
| atgcgcagac cgaggcaggg aggcggggt gcgggaggct ccgcggctgc gcgggcgcgt | 60 |
| gctggtggcc tcggcggagg ctcagtcccg gcccgcgccc gcggcgcccc cgctgcggcc | 120 |
| cgagcggcct ggctgcggga tctgtgcgca cggatggcgc ggccgccccg gcagcacccg | 180 |
| ggggtctggg cgtcgctgct cctgctgcta ctgacggggc ccgccgcctg cgcagccagc | 240 |
| cccgcggacg acgtgcggg cccgggggc cgggacccc ggggacgcgc gcgggggggac | 300 |
| acgggcgccg acgaggcggt gccgcgccac gactcctcct acggcacctt cgcggggag | 360 |
| ttctacgacc tgcgctacct gtcggaggag ggttacccct tccctactgc tcctcctgtg | 420 |
| gatccatttg ccaaaatcaa agtggacgac tgtggaaaaa ctaagggatg ctttagatat | 480 |
| ggcaaaccag gctgtaatgc agagacctgt gactatttcc tcagctaccg gatgatagg | 540 |
| gctgatgtag aatttgagct gagtgcagac acagatggtt gggtagcagt tggattctct | 600 |
| tcagacaaga aaatgggtgg tgatgatgtc atggcctgcg tccatgatga caatggcagg | 660 |
| gtccgcatac agcacttcta taatgtaggc cagtgggcaa aggagattca gagaaaccct | 720 |
| gccagagatg aagaaggagt ttttgagaac atcgcgtca cctgcagatt taaacgccct | 780 |
| gtgaatgttc ccagagatga aacaattgtt gatctgcatt tgagttggta ttatctgttt | 840 |
| gcttggggtc cagccattca gggctctatc actcgacatg atatagactc accgccggct | 900 |
| tcagagcgtg ttgtcagtat ttacaagtat gaagacattt ttatgccatc agctgcctat | 960 |
| caaaccttct catctccatt ttgttgctt ctgattgttg ctctgacctt ctacctattg | 1020 |
| atgggaaccc cctaaccaca gctgcagggc caacagatta catggattgg gaagtctta | 1080 |
| gtataaatat atttttaaa gaatatccag tataatttta gcttcaatta tttaagaaaa | 1140 |
| aaaacctcat ataatttcag ctttttggaa gaaagaacaa gcttctttt | 1189 |

<210> SEQ ID NO 32
<211> LENGTH: 1272
<212> TYPE: DNA
<213> ORGANISM: Homo sapiens

<400> SEQUENCE: 32

```
gcaaaaccgt gagctggatt tataatcgcc ctataaagct ccagaggcgg tcaggcacct      60
gcagaggagc cccgccgctc cgccgactag ctgcccccgc gagcaacggc ctcgtgattt     120
ccccgccgat ccggtccccg cctccccact ctgcccccgc ctaccccgga gccgtgcagc     180
cgcctctccg aatctctctc ttctcctggc gctcgcgtgc gagagggaac tagcgagaac     240
gaggaagcag ctggaggtga cgccgggcag attacgcctg tcagggccga gccgagcgga     300
tcgctgggcg ctgtgcagag gaaaggcggg agtgcccggc tcgctgtcgc agagccgagg     360
tggcctgttt ctgcgccgga ccagtcgagg actctggaca gtagaggccc cgggacgacc     420
gagctgatgg cgtcttcgac cccatcttcg tccgcaacct cctcgaacgc gggagcggac     480
cccaatacca ctaacctgcg ccccacaacg tacgatacct ggtgcggcgt ggcccatgga     540
tgcaccagaa aactggggct caagatctgc ggcttcttgc aaaggaccaa cagcctggaa     600
gagaagagtc gccttgtgag tgccttcaag gagaggcaat cctccaagaa cctgctttcc     660
tgtgaaaaca gcgaccggga tgcccgcttc cggcgcacag agactgactt ctctaatctg     720
tttgctagag atctgcttcc ggctaagaac ggtgaggagc aaaccgtgca attcctcctg     780
gaagtggtgg acatactcct caactatgtc cgcaagacat ttgatcgctc caccaaggtg     840
ctggactttc atcacccaca ccagttgctg aaggcatgg agggcttcaa cttggagctc     900
tctgaccacc ccgagtccct ggagcagatc ctggttgact gcagagacac cttgaagtat     960
ggggttcgca caggtcatcc tcgattttc aaccagctct ccactggatt ggatattatt    1020
ggcctagctg gagaatggct gacatcaacg gccaatacca acatgccatc agacatgagg    1080
gagtgttggt tgctacggtg atggggctca gagcagaacc aaagcatgat tgtgacctcc    1140
agaggtgatg gtaactgcac acatggtttc caagggtctt cctcctaaat ttccaggggc    1200
ctcccaagga aaatgtacat attctttttg gaaataaaat acttctacca acataaaaaa    1260
aaaaaaaaaa aa                                                        1272
```

<210> SEQ ID NO 33
<211> LENGTH: 2621
<212> TYPE: DNA
<213> ORGANISM: Homo sapiens

<400> SEQUENCE: 33

```
ccttttttgg cctcgacggc ggcaacccag cctccctcct aacgccctcc gcctttggga      60
ccaaccaggg gagctcaagt tagtagcagc caaggagagg cgctgccttg ccaagactaa     120
aaagggaggg gagaagagag gaaaaaagca agaatccccc acccctctcc cgggcggagg     180
gggcgggaag agcgcgtcct ggccaagccg agtagtgtct ccactcggt gcgtctctct     240 aggagccgcg cgggaaggat gctggtccgc aggggcgcgc gcgcagggcc caggatgccg     300
cggggctgga ccgcgctttg cttgctgagt ttgctgcctt ctgggttcat gagtcttgac     360
aacaacggta ctgctacccc agagttacct acccagggaa cattttcaaa tgtttctaca     420
aatgtatcct accaagaaac tacaacacct agtaccctgg aagtaccag cctgcaccct     480 gtgtctcaac atggcaatga ggccacaaca aacatcacag aaacgacagt caaattcaca     540
tctacctctg tgataacctc agtttatgga aacacaaact cttctgtcca gtcacagacc     600
tctgtaatca gcacagtgtt caccaccccca gccaacgttt caactccaga gacaaccttg     660
aagcctagcc tgtcacctgg aaatgtttca gaccttcaa ccactagcac tagccttgca     720
acatctccca ctaaacccta tacatcatct tctcctatcc taagtgacat caaggcagaa     780
```

| | |
|---|---|
| atcaaatgtt caggcatcag agaagtgaaa ttgactcagg gcatctgcct ggagcaaaat | 840 |
| aagacctcca gctgtgcgga gtttaagaag gacaggggag agggcctggc ccgagtgctg | 900 |
| tgtggggagg agcaggctga tgctgatgct ggggcccagg tatgctccct gctccttgcc | 960 |
| cagtctgagg tgaggcctca gtgtctactg ctggtcttgg ccaacagaac agaaatttcc | 1020 |
| agcaaactcc aacttatgaa aaagcaccaa tctgacctga aaaagctggg gatcctagat | 1080 |
| ttcactgagc aagatgttgc aagccaccag agctattccc aaaagaccct gattgcactg | 1140 |
| gtcacctcgg gagccctgct ggctgtcttg ggcatcactg gctatttcct gatgaatcgc | 1200 |
| cgcagctgga gccccacagg agaaaggctg ggcgaagacc cttattacac ggaaaacggt | 1260 |
| ggaggccagg gctatagctc aggacctggg acctcccctg aggctcaggg aaaggccagt | 1320 |
| gtgaaccgag gggctcagga aaacgggacc ggccaggcca cctccagaaa cggccattca | 1380 |
| gcaagacaac acgtggtggc tgataccgaa ttgtgactcg gctaggtggg gcaaggctgg | 1440 |
| gcagtgtccg agagagcacc cctctctgca tctgaccacg tgctaccccc atgctggagg | 1500 |
| tgacatctct tacgcccaac ccttccccac tgcacacacc tcagaggctg ttcttggggc | 1560 |
| cctacacctt gaggagggc aggtaaactc ctgtccttta cacattcggc tccctggagc | 1620 |
| cagactctgg tcttctttgg gtaaacgtgt gacggggga agccaaggtc tggagaagct | 1680 |
| cccaggaaca atcgatggcc ttgcagcact cacacaggac ccccttcccc tacccctcc | 1740 |
| tctctgccgc aatacaggaa ccccaggggg aaagatgagc ttttctaggc tacaattttc | 1800 |
| tcccaggaag ctttgatttt taccgttct tccctgtatt ttctttctct actttgagga | 1860 |
| aaccaaagta accttttgca cctgctctct tgtaatgata tagccagaaa aacgtgttgc | 1920 |
| cttgaaccac ttccctcatc tctcctccaa gacactgtgg acttggtcac cagctcctcc | 1980 |
| cttgttctct aagttccact gagctccatg tgcccctct accatttgca gagtcctgca | 2040 |
| cagttttctg gctggagcct agaacaggcc tcccaagttt taggacaaac agctcagttc | 2100 |
| tagtctctct ggggccacac agaaactctt tttgggctcc ttttctccc tctggatcaa | 2160 |
| agtaggcagg accatgggac caggtcttgg agctgagcct ctcacctgta ctcttccgaa | 2220 |
| aaatcctctt cctctgaggc tggatcctag ccttatcctc tgatctccat ggcttcctcc | 2280 |
| tccctcctgc cgactcctgg gttgagctgt tgcctcagtc ccccaacaga tgcttttctg | 2340 |
| tctctgcctc cctcaccctg agccccttcc ttgctctgca ccccccatatg gtcatagccc | 2400 |
| agatcagctc ctaaccctta tcaccagctg cctcttctgt gggtgaccca ggtccttgtt | 2460 |
| tgctgttgat ttcttttccag aggggttgag cagggatcct ggtttcaatg acggttggaa | 2520 |
| atagaaattt ccagagaaga gagtattggg tagatatttt ttctgaatac aaagtgatgt | 2580 |
| gtttaaatac tgcaattaaa gtgatactga aacacaaaaa a | 2621 |

<210> SEQ ID NO 34
<211> LENGTH: 1816
<212> TYPE: DNA
<213> ORGANISM: Homo sapiens

<400> SEQUENCE: 34

| | |
|---|---|
| ggcgaccacg tgtcttcaa aagcccccgtc agggttggct tcctgggggcc ggaccgactg | 60 |
| tgggtcagtt tgcaccagcg ctctggaatc gagttacgcg cgaaagggca gagtttctgg | 120 |
| aggaaaccgc agcctctcaa ccgctgaccg ggtctcagaa ggcccccggc agggccgctt | 180 |
| ggcgggaact gaccacgcgc cagtcaggct ctccaggac ctgcgcaggc gcgtgtgggc | 240 |
| ggagtcgtgc gcaggggggcg ggcttcggg aaggagccac agagagggcg gggcgtagga | 300 |

```
cctgcgcttc gggggtggag tcggagcggc gcggcggcgg tcatgcggga cgcggatgca    360
gacgcaggcg gaggcgctga cggcggggat ggccggggtg ccacagctg ccgcgggggc    420 gtggacacag ccgcagctcc ggccggtgga gctccccag cgcacgcgcc aggtccgggc    480
agagacgccg cgtctgcggc caggggtca cgaatgcggc cgcacatatt caccctcagc    540
gtgcctttcc cgaccccctt ggaggcggaa atcgcccatg ggtccctggc accagatgcc    600
gagccccacc aaagggtggt tgggaaggat ctcacagtga gtggcaggat cctggtcgtc    660
cgctggaaag ctgaagactg tcgcctgctc cgaatttccg tcatcaactt tcttgaccag    720 cttttccctgg tggtgcggac catgcagcgc tttgggcccc ccgtttcccg ctaagcctgg    780
cctgggcaaa tggagcgagg tcccacttg cgtctccttg taggcagtgc gtccatcctt    840
ccctagggca ggaattccca cagttgctac tttcctggga gggcctcatg ttttatctgg    900
ttcttaaatg tttgttacta cagaaaataa aactgcgcta ctattccaag tctgagttta    960
tttgcagctg gggcacctcc caatattctt gttgtgcttg ggttgctggg gggggttct   1020 agaattcaga tattcaagga gtacaaggaa attgaagaca atttaggaaa tggaagaaaa   1080
tgaaaatcaa ttgggttctg tcattcagga ttaactactg tcaacatttt ggaatacttc   1140
ctcagtttta cagttgcact tacatagtaa atgtgtaact gtaatataca ccacataata   1200
tttgcaagtt tagtgttaaa ttttttttcct gattttaaaa tctaacatga gctttttcc   1260 tctaacgatc agtgaagaaa gtgctgggggc aattgactag tgtctggggc aaggagttgg   1320
ctccctggaa aatacagtgt ctccagcctt agggctcttt tatagattct atcagatttt   1380
ctgagagtga aaaggaagag gtacaactgc ttttattctc agaaaacaag gaaatggttt   1440 gatcctttg agtcttgctt tgaagatgtg ctgtgtggga ccagagcagc tcttaactgt   1500
aggcttgttt ccctctatgg aggcaacaaa caccattctg ggcaccctgg ccagtgctgc   1560
ctaggtgaac atgagcttct ctatcctggt gggtggggac agctgctagt ccctgtcctg   1620
cttgcacact ggagttaccg ttcatcctct cctgctgggg tgatggcctt ccctggtctt   1680
gggtagcttc ctcacacgcc tgtgctcacc agtagtcgta gtccgctgca cactggaacg   1740
ggagcctctg tggatatcca gggttctttc cctgtgcagc tctcttctct ctggttctcc   1800
gccctgcaaa ctccag                                                  1816
```

<210> SEQ ID NO 35
<211> LENGTH: 773
<212> TYPE: DNA
<213> ORGANISM: Homo sapiens

<400> SEQUENCE: 35

```
gtggggtcag caagagaaac tctacggcta tgggagagcc tgcgttcacc tcttttccga     60
gcccacctgt tctggggaag ctcaaaagaa acatgatgcc ctgggcttta cagaagaaac    120
gagaaatcca catggccaag gcccatcgga gacgagctgc gaggtctgct ctccccatga    180
gactcaccag ctgcatcttc cggaggccgg tgacaaggat caggtctcat cctgacaacc    240
aggtcagacg cagaaaaggg gacgagcacc tggagaagcc gcagcaactc tgcgcctacc    300
ggagactgca ggccctgcag ccctgcagca gccaaggaga aggttcaagt ccactgcatt    360
tggagagcgt cttaagtatc cttgcaccgg ggacggccgg tgaatctctg gacagagctg    420
gtgctgagcg tgtgcgcatc ccgcttgagc ccacccctgg gcggtttcca gctgtggcag    480
gggggccaac cccaggaatg ggttgtcagc tcccaccgcc cctctctggc caattggtga    540
```

```
ctcctgcaga tatccggaga caggccagga gggtgaagaa agccagggag agactggcca      600
aggccttgca ggcagacagg ctggccagcc aggcagaaat gctgacaggt gggtgaagct      660
cagtcctggg ctttcggtcc ctttcttttta atgcccatcc tcattcctac tctgaattgt     720
cacacttttc ccttccccac cagttcttta ataaaagtat ttgaaaggca aca             773

<210> SEQ ID NO 36
<211> LENGTH: 773
<212> TYPE: DNA
<213> ORGANISM: Homo sapiens

<400> SEQUENCE: 36
gtggggtcag caagagaaac tctacggcta tgggagagcc tgcgttcacc tcttttccga      60
gcccacctgt tctggggaag ctcaaaagaa acatgatgcc ctgggcttta cagaagaaac     120
gagaaatcca catggccaag gccatcggaa gacgagctgc gaggtctgct ctccccatga     180
gactcaccag ctgcatcttc cggaggccgg tgacaaggat caggtctcat cctgacaacc     240
aggtcagacg cagaaaaggg gacgagcacc tggagaagcc gcagcaactc tgcgcctacc     300
ggagactgca ggccctgcag ccctgcagca gccaaggaga aggttcaagt ccactgcatt     360
tggagagcgt cttaagtatc cttgcaccgg ggacggccgg tgaatctctg acagggctg      420 gtgctgagcg tgtgcgcagc ccgcttgagc ccacccctgg gcggtttcca gctgtggcag     480
gggggccaac cccaggaatg ggttgtcagc tcccaccgcc cctctctggc caattggtga     540
ctcctgcaga tatccggaga caggccagga gggtgaagaa agccagggag agactggcca     600
aggccttgca ggcagacagg ctggccagcc aggcagaaat gctgacatgt agatgaagcg     660
cagtcctggg ctttcggtcc ctttcttttta atgcccatcc tcattcctac tctgaattgt    720
cacacttttc ccttccccac cagttcttta ataaaagtat ttgaaaggca aca             773

<210> SEQ ID NO 37
<211> LENGTH: 1583
<212> TYPE: DNA
<213> ORGANISM: Homo sapiens

<400> SEQUENCE: 37
ctcctgggcc tctcaaagtc tgagccccgc tccgctgatg cctgtctgca gaatccgcac      60
caaccagcac catgcccatg actctggggt actgggacat ccgtgggctg cccacgcca     120 tccgcttgct cctggaatac acagactcaa gctatgtgga aaagaagtac acgctggggg     180
acgctcctga ctatgacaga agccagtggc tgaatgaaaa attcaagctg ggcctggact     240
ttcccaatct gccctacttg attgatgggg ctcacaagat cacccagagc aatgccatcc     300
tgcgctacat tgcccgcaag cacaacctgt gtggggagac agaagaggag aagattcgtg     360
tggacatttt ggagaaccag gttatggata ccacatggga gctggtcaga ctgtgctatg     420
acccagattt tgagaaactg aagccaaaat acttggagga actccctgaa aagctaaagc     480
tctactcaga gtttctgggg aagcggccat ggttgcagg agacaagatc acctttgtgg     540
atttccttgc ctatgatgtc cttgacatga agcgtatatt tgagcccaag tgcttggacg     600
ccttcctaaa cttgaaggac ttcatctccc gctttgaggg tttgaagaag atctctgcct     660
acatgaagtc cagccaattc ctccgaggtc ttttgtttgg aaagtcagct acatggaaca    720
gcaaataggg cccagtgatg ccagaagatg ggagggagga ccaaccttg ctgcctgcga     780 ccctggagga cagcctgact ccctggacct gccttcttcc ttttttcctc tttctactct    840
cttctcttcc ccaaggcctc attggcttcc tttcttctaa catcatccct ccccgcatcg    900
```

```
aggctcttta aagcttcagc tccccactgt cctccatcaa agtccccctc ctaacgtctt      960
cctttccctg cactaacgcc aacctgactg cttttcctgt cagtgctttt ctcttctttg     1020
agaagccaga ctgatctctg agctccctag cactgtcctc aaagaccatc tgtatgccct     1080
gctccctttg ctgggtccct accccagctc cgtgtgatgc ccagtaaagc ctgaaccatg     1140
cctgccatgt cttgtcttat tccctgaggc tcccttgact caggactgtg ctcgaattgt     1200
gggtggtttt ttgtcttctg ttgtccacag ccagagctta gtggatgggt gtgtgtgtgt     1260
gtgtgttggg ggtggtgatc aggcaggttc ataaatttcc ttggtcattt ctgccctcta     1320
gccacatccc tctgttcctc actgtgggga ttactacaga aaggtgctct gtgccaagtt     1380
cctcactcat tcgcgctcct gtaggccgtc tagaactggc atggttcaaa gaggggctag     1440
gctgatgggg aagggggctg agcagctccc aggcagactg ccttctttca ccctgtcctg     1500
atagacttcc ctgatctaga tatccttcgt catgacactt ctcaataaaa cgtatcccac     1560
cgtattgtaa aaaaaaaaaa aaa                                             1583

<210> SEQ ID NO 38
<211> LENGTH: 1862
<212> TYPE: DNA
<213> ORGANISM: Homo sapiens

<400> SEQUENCE: 38
acccaaagtc ttcaagcctg agttcctgc ttggttcttc ctgaggtctg agcaccttct        60
agactacatc cagatctgtt ttccctgcag attcatgaag atgagcatcc ggactccacc      120
cagactcctg gagcttgcag ggcggagcct gctgagggac caagctttgg ccatgtccac      180
cctggaggag ctgcccacag aacttttccc cccactgttc atggaggcct tcagcaggag      240
acgctgtgag gccctgaagc tgatggtgca ggcctggccc ttccgccgcc tccctctgag      300
gcctctgata aagatgcctt gtctggaggc cttccaagct gtgctcgatg gcttgatgc       360 actgcttacc caaggggttc gtcccaggag gtggaaactc caagtgctgg atttacagga     420
tgtctgtgag aacttctgga tggtttggtc tgaagctatg gcccatgggt gcttcctcaa     480
tgccaagagg aacaaaaaac cagtgcagga ctgtccaagg atgagaggac ggcagccctt     540
gactgtgttc gtagaacttt ggctcaagaa caggactctg gatgaatacc tcacctacct     600
ccttctatgg gtcaagcaga ggaaagattt actacacctg tgctgtaaga agctgaaaat     660
tttgggaatg cccttccgca atatcagaag catcctgaaa atggtgaacc tagactgtat     720
ccaggaggtg gaagtgaatt gcaagtgggt actgccatc ctgacacagt ttaccccata     780
cctgggccac atgaggaatc ttcagaagct cgttctctcc cacatggatg tctctcgcta     840
cgtttcccca gagcagaaga aggagattgt tacccagttc accactcagt tcctcaagct     900
gcgctgcctc caaaagcttt atatgaactc tgtttctttc ctcgaaggcc acctggacca     960
gctgctcagc tgtctgaaga cctcgttaaa agtcctcaca ataactaact gtgtgctttt    1020
ggaatcagac ttgaagcatc tatcccagtg cccgagtatc agtcaactaa agaccctgga    1080
cctgagtggc atcagactga ccaattatag tcttgtgcct ctccaaattc tcctagaaaa    1140
agttgcagcc cccttgagt acctggattt agatgactgt ggcatcatag actcccaagt    1200
caacgccatc ctgcctgccc tgagccgctg ctttgagctc aacaccttca gcttctgtgg    1260
aaatcccatc tgcatggcca ccctggagaa cctgctgagc cacacaatca tactcaaaaa    1320
cttatgtgtg gagctgtatc ctgcccccg agagagttat ggtgctgatg gtactctctg    1380
```

| | |
|---|---|
| ctggagcaga tttgctcaaa ttagggctga gctgatgaac agagtgaggg acttaaggca | 1440 |
| ccccaagagg atcttgttct gtactgacta ctgccctgac tgtggcaaca ggtcatttta | 1500 |
| tgacctggag gcagatcaat actgctgttg aatgcctgcc tatttggatg ggtatgtcaa | 1560 |
| acgctttctt ctggacactt ggaaactaaa acctaggtct taggtacatc ctaaagggag | 1620 |
| cacagaaccc atcatttcac acataggctc tgaaagtggg aaaggaaagc tgatcaagca | 1680 |
| ggggccggac ttgggggaaa tgttgccatg gattcgatgg gactttgggg acctgtgtcc | 1740 |
| tgtagattcg aaaatgggaa tctgaatgtc tagagtggaa ttcaggcttg agaatacatg | 1800 |
| agggagttac tcttgcatgg atggttgtaa agaaacaatc agaaataaag gaaaactgag | 1860 |
| ca | 1862 |

<210> SEQ ID NO 39
<211> LENGTH: 1855
<212> TYPE: DNA
<213> ORGANISM: Homo sapiens

<400> SEQUENCE: 39

| | |
|---|---|
| acccaaagtc ttcaagcctg gagttcctgc ttggttcttc ctgaggactg agcaccttct | 60 |
| agactacatc cagatctgtt ttccctgcag attcgtgaag atgagcatcc ggactccacc | 120 |
| cagactcctg gagcttgcag gcggagcct gctgagggac caagccttgg ccatgtccac | 180 |
| cctggaggag ctgcccacag aacttttccc cccactgttc atggaggcct tcagcaggag | 240 |
| acgctgtgag gccctgaagc tgatggtgca ggcctggccc ttccgccgcc tccctctgag | 300 |
| gcctctgata aagatgcctt gtctggaggc cttccaagct gtgctcgatg gctggatgc | 360 |
| actgcttacc caaggggttc atcccaggag gtggaaactt caagtgctgg atttacagga | 420 |
| tgtctgtgag aacttctgga tggtttggtc tgaagctatg gcccatgggt gcttcctcaa | 480 |
| tgccaagagg aacaaaaaac cagtgcagga ctgtccaagg atgagaggac agcagccctt | 540 |
| gactgtgttc gtagaacttt ggctcaagaa caggactctg gatgaatacc tcacctgcct | 600 |
| ccttctatgg gtcaagcaga ggaaagattt actacacctg tgctgtaaga agctgaaaat | 660 |
| tttgggaatg ccccttccgca atatcagaag catcctgaaa atggtgaacc tagactgtat | 720 |
| ccaggaggtg gaagtgaatt gcaagtgggt actgcccatc ctgacacagt ttaccccata | 780 |
| cctgggccac atgaggaatc ttcagaagct cgttctctcc cacatggatg tctctcgcta | 840 |
| cgtttcccca gagcagaaga aggagattgt tacccagttc accactcagt tcctcaagct | 900 |
| gtgctgcctc caaaagcttt ctatgaactc tgtttctttc ctcgaaggcc acctggacca | 960 |
| gctgctcagc tgtctgaaga cctcgttaaa ggtcctcaca ataactaact gtgtgctttt | 1020 |
| ggaatcagac ttgaagcatc tatcccagtg cccgagtatc agtcaactaa agaccctgga | 1080 |
| cctgagtggc atcagactga ccaattacag tcttgtgcct ctccaaattc tcctagaaaa | 1140 |
| agttgcagcc acccttgagt acctggattt agatgactgt ggcatcatag actcccaagt | 1200 |
| caacgccatc ctgcctgccc tgagccgctg ctttgagctc aacaccttca gcttctgtgg | 1260 |
| aaatcccatc tccatggcca cctggagaa cctgctgagc cacacaatca tactcaaaaa | 1320 |
| cttatgcgtg gagctgtatc ctgcccccg ggagagttat gatgctgatg gtactctctg | 1380 |
| ctggagcaga tttgctcaaa ttagggctga gctgatgaag agagtgaggg acttaaggca | 1440 |
| ccccaagagg atcttgttct gtactgactg ctgccctgac tgtggcaaca ggtcatttta | 1500 |
| tgacctggag gcagatcaat gctgctgttg aatgcctgcc tatttgggtg gatatgtcaa | 1560 |
| acgctttctt ctggacactt ggaaactaaa acctaggtct taggtacatc ctataggag | 1620 |

```
cacagaaccc atcatttcac acatgggctc tgaaagtggg aaaggaaagg tgatcaagca   1680
ggggcaggac ttgggggaag tgttgccatg gattcgatgg gactttgggg acctgtgtcc   1740
tgtagagtgg aaaatgggaa tttgaatgtc tagagtggag gcttgagaat acttgaggga   1800
gttactcttg gatgcatggt tgtaaagaaa caatcagaaa taaggaaaaa ctgag         1855

<210> SEQ ID NO 40
<211> LENGTH: 1648
<212> TYPE: DNA
<213> ORGANISM: Homo sapiens

<400> SEQUENCE: 40
gcagggaatg agctcctgat cttggggagt acttaaaaga attttttctt ggaagaatta    60
ctgcaggaaa cattcataga accttgggaa acatgaattc tggaatcttg caagtcttcc   120
agagggcact cacctgtccc atctgcatga actacttcct agacccagtc accatagact   180
gtgggcacag cttttgccgg ccctgtttgt acctcaactg caagacacg gcagttcttg   240 ctcagtgctc tgaatgcaag aagacaacgc ggcagagaaa cctcaacact gacatttgtt   300
tgaagaacat ggctttcatt gccagaaaag ccagcctccg gcaattcctt agctctgagg   360
agcaaatatg tgggatgcac agagagacaa agaagatgtt ctgtgaagtg acaagagcc   420 tgctctgttt gccgtgctcc aactctcagg agcaccggaa tcacatacac tgtcccattg   480
agtgggctgc tgaggaacgc cgggaggagc tcctaaaaaa aatgcagtct ttatgggaaa   540
aagcttgtga aaatctcaga aatctgaaca tggaaaccac aagaaccaga tgctggaagg   600
attatgtgag tttaaggata gaagcaatca gagctgaata tcagaagatg cctgcatttc   660
tccatgaaga agagcaacat cacttggaaa ggctgcgaaa ggagggcgag acatttttc   720 agcaactcaa tgaaagcaaa gccagaatgg aacattccag ggagcttta agaggaatgt   780 atgaggatct gaagcaaatg tgccataaag cagatgtgga gctactccag gcttttggag   840
acatattaca caggtatgag tctctgctgc tgcaagtgtc tgagcctgtg aatccagagc   900
tcagtgcagg gcccatcact ggactgctgg acagcctcag tggattcaga gttgattta    960 ctctgcagcc tgaaagagcc aatagtcata tcttcctgtg tggagatttg agaagcatga  1020
atgttggatg tgaccctcaa gatgatcccg atatcactgg aaaatctgaa tgttttcttg  1080
tatggggggc tcaggctttc acatctggca aatattattg ggaggttcat atggggact   1140 cttggaattg ggcttttggt gtctgtaaca attattggaa agagaagaga cagaatgaca  1200
agatagatgg agaggaggga ctctttcttc ttggatgtgt taaggaggac actcactgca  1260
gtctctttac cacctcccca cttgtggtgc aatatgttcc aagacctacc agcacagtag  1320
gattattcct ggattgtgaa ggtagaaccg tgagctttgt tgatgttgat caaagttccc  1380
tgatatacac catccccaat tgctccttct cacctcctct caggcctatc ttttgctgta  1440
gtcacttctg accagagaaa agtcagaaat gtgcctgtat gctctgggaa cctgtttatc  1500
ccagaaagcc ctcttttttcg cacctcatca aacagaacaa ataagttata tttaatgtct  1560
ttagttgcat tctaatgtca tcaaaactca tttatagtgt ttctattaaa tatggtgaaa  1620
acattaaaaa aaaaaaaaa aaaaaaaa                                      1648

<210> SEQ ID NO 41
<211> LENGTH: 1617
<212> TYPE: DNA
<213> ORGANISM: Homo sapiens
```

```
<400> SEQUENCE: 41
ccaccccccc cccccaccac caccaccacc accaccccgc cggccggccc caggcctcga      60
cgccctgggt cccttccggg gtggggcggg ctgtcccagg ggggctcacc gccattcatg     120
aaggggtgga gcctgcctgc ctgtgggcct ttacaagggc ggctggctgg ctggctggct     180
gtccgggcag gcctcctggc tgcacctgcc gcagtgcaca gtccggctga ggtgcacggg     240
agcccgccgg cctctctctg cccgcgtccg tccgtgaaat tccggccggg gctcaccgcg     300
atggccctcc cgacaccctc ggacagcacc ctccccgcgg aagcccgggg acgaggacgg     360
cgacggagac tcgtttggac cccgagccaa agcgaggccc tgcgagcctg ctttgagcgg     420
aacccgtacc cgggcatcgc caccagagaa cggctggccc aggccatcgg cattccggag     480 cccaggtcc agatttggtt tcagaatgag aggtcacgcc agctgaggca gcaccgcgg      540 gaatctcggc cctggcccgg gagacgcggc ccgccagaag gccggcgaaa gcggaccgcc     600
gtcaccggat cccagaccgc cctgctcctc cgagcctttg agaaggatcg ctttccaggc     660
atcgccgccc gggaggagct ggccagagag acgggcctcc cggagtccag gattcagatc     720
tggtttcaga atcgaagggc caggcacccg ggacagggtg gcagggcgcc cgcgcaggca     780
ggcggcctgt gcagcgcggc ccccggcggg ggtcaccctg ctccctcgtg ggtcgccttc     840
gcccacaccg gcgcgtgggg aacggggctt cccgcacccc acgtgccctg cgcgcctggg     900
gctctcccac agggggcttt cgtgagccag gcagcgaggg ccgcccccgc gctgcagccc     960
agccaggccg cgccggcaga gggggtctcc caacctgccc cggcgcgcgg ggatttcgcc    1020
tacgccgccc cggctcctcc ggacggggcg ctctcccacc ctcaggctcc tcggtggcct    1080
ccgcacccgg gcaaaagccg ggaggaccgg gacccgcagc gcgacggcct gccgggcccc    1140
tgcgcggtgg cacagcctgg gcccgctcaa gcggggccgc agggccaagg ggtgcttgcg    1200
ccacccacgt cccaggggag tccgtggtgg ggctggggcc ggggtcccca ggtcgccggg    1260
gcggcgtggg aacccccaagc cggggcagct ccacctcccc agcccgcgcc cccggacgcc    1320
tccgcctccg cgcggcaggg gcagatgcaa ggcatcccgg cgccctccca ggcgctccag    1380
gagccggcgc cctggtctgc actcccctgc ggcctgctgc tggatgagct cctggcgagc    1440
ccggagtttc tgcagcaggc gcaacctctc ctagaaacgg aggcccgggg ggagctggag    1500
gcctcggaag aggccgcctc gctggaagca cccctcagcg aggaagaata ccgggctctg    1560
ctggaggagc tttaggacgc ggggttggga cggggtcggg tggttcgggg cagggcg      1617
```

US 9,260,755 B2

COMPOSITIONS AND METHODS FOR CHARACTERIZING AND TREATING MUSCULAR DYSTROPHY

CLAIM OF PRIORITY

The present application claims the benefit of U.S. Provisional Patent Application No. 61/622,942, filed on Apr. 11, 2012. The entire contents of the foregoing are incorporated by reference herein.

FEDERALLY SPONSORED RESEARCH OR DEVELOPMENT

This invention was made with Government support under Grant No. U54 HD060848 awarded by the National Institutes of Health. The Government has certain rights in the invention.

BACKGROUND OF THE INVENTION

Facioscapulohumeral muscular dystrophy (FSHD) is a progressive neuromuscular disorder caused by contractions of repetitive elements within the macrosatellite D4Z4 on chromosome 4q35. There is currently no effective treatment available for FSHD and clinical trials with novel therapeutics have been discouraged by the lack of a recognized mouse model. Clinical trials have also been discouraged by the fact that FSHD is a highly variable and slowly progressing disease whereas the efficacy of therapeutic interventions is ideally established over short periods of time. Therefore, molecular biomarkers of FSHD that could be used to assay responsiveness to therapy would greatly facilitate FSHD therapeutic development and clinical research. High-density oligonucleotide arrays reliably quantify the expression levels of thousands of genes simultaneously and enable identification of such biomarkers.

SUMMARY OF THE INVENTION

As described below, the present invention features panels of biomarkers useful in diagnosing muscular dystrophy (e.g., FSHD) in a subject, as well as cellular compositions and chimeric animals useful in drug screening.

Thus, in a first aspect, the invention provides methods for identifying a candidate compound for treatment of Facioscapulohumeral muscular dystrophy (FSHD). The methods include contacting a sample comprising a cell derived from an FSHD affected subject with a test compound; determining a level of expression of a gene selected from the group consisting of PRAMEF1, SLC34A2, TRIM49, TRIM43, CD177, NAAA, HSPA6, TC2N, CD34, ATP2A1, PAX7, MYF5, MRAP2, DAG1, CLYBL, CALCRL, ZNF445, and SPATA17, or at least two genes selected from the group consisting of SLC34A2, TRIM49, TRIM43, PRAMEF1, CD177, NAAA, HSPA6, TC2N, CD34, ATP2A1, PAX7, MYF5, MRAP2, DAG1, CLYBL, CALCRL, ZNF445, and SPATA17 in the sample; and selecting as a candidate compound a test compound that reduces the level of expression of one or more of SLC34A2, TRIM49, TRIM43, PRAMEF1, CD177, NAAA, HSPA6, TC2N, or CD34, or a test compound that increases the level of expression of one or more of ATP2A1, PAX7, MYF5, MRAP2, DAG1, CLYBL, CALCRL, ZNF445, or SPATA17. In some embodiments, where expression of only a single gene is determined, that gene is not PRAMEF1 or TRIM43. In some embodiments where expression of only two genes is determined, the genes are not PRAMEF1 and TRIM43. Thus, in some embodiments, where PRAMEF1 or TRIM43 are determined, at least one other gene that is not PRAMEF1 or TRIM43 is also determined.

In some embodiments, the methods include determining a level of expression of at least one gene shown in Table 4 that is upregulated in FSHD, optionally wherein the gene is selected from the group consisting of PRAMEF1; TRIM43; SLC34A2; TRIM49 and CD34, in a sample comprising a cell from the subject; and determining a level of expression of at least one gene shown in Table 4 that is downregulated in FSHD, optionally wherein the gene is selected from the group consisting of PAX7; MYF5; ATP2A1; DAG1; and MRAP2; in the sample; and selecting as a candidate compound a test compound that reduces the level of expression of a gene shown in Table 4 that is upregulated in FSHD and increases the level of expression of a gene shown in Table 4 that is downregulated in FSHD.

In some embodiments, the methods include administering the selected candidate compound to an animal model of FSHD, wherein the animal model comprises at least one chimeric muscle tissue comprising cells from a subject affected with FSHD; performing an assay to determine a level of expression of at least one gene shown in Table 4; comparing the level of expression of the at least one gene to a reference level of expression that represents a level of expression in the absence of the candidate compound; and selecting as a candidate therapeutic compound a candidate compound that reduces the level of expression of a gene shown in Table 4 that is upregulated in FSHD and increases the level of expression of a gene shown in Table 4 that is downregulated in FSHD.

In some embodiments, the level of expression of a gene shown in Table 4 that is upregulated in FSHD is reduced to a level that is nearly or substantially the same as, i.e., not statistically significantly different from, a level in a control cell that is not derived from an FSHD affected subject, or an animal model that comprises at least one chimeric muscle tissue comprising cells from a control subject who is not affected with FSHD.

In some embodiments, the level of expression of a gene shown in Table 4 that is downregulated in FSHD is increased to a level that is nearly or substantially the same as, i.e., not statistically significantly different from, a level in a control cell that is not derived from an FSHD affected subject, or an animal model that comprises at least one chimeric muscle tissue comprising cells from a control subject who is not affected with FSHD.

In some embodiments, levels of expression are determined using quantitative PCR (qPCR).

In some embodiments, the control cell is derived from a first degree relative of the FSHD affected subject.

In another aspect, the invention provides methods (e.g., computer-implemented methods) for identifying a candidate compound for treatment of Facioscapulohumeral muscular dystrophy (FSHD). The methods include contacting a sample comprising a cell derived from an FSHD affected subject with a test compound; determining a level of expression of at least one gene shown in Table 4 that is upregulated in FSHD, optionally wherein the gene is selected from the group consisting of PRAMEF1; TRIM43; SLC34A2; TRIM49 and CD34, in the sample, to determine a value [GeneUP]; determining a level of expression of at least one gene shown in Table 4 that is downregulated in FSHD, optionally wherein the gene is selected from the group consisting of PAX7; MYF5; ATP2A1; DAG1; and MRAP2; in the sample, to determine a value [GeneDOWN]; using the value [GeneDOWN] and the value for [GeneUP] to calculate a classifier for the test compound; comparing the classifier to a reference classifier that represents a classifier in a cell that is from a control subject who is not affected with FSHD; and selecting as a candidate compound a test compound that has a classifier that is not statistically different from the reference classifier.

In some embodiments, [GeneUP] is a level of PRAMEF1 in the sample.

In some embodiments, [GeneDOWN] is a level of PAX7 in the sample.

In some embodiments, the classifier is calculated as:

[GeneUP]−[GeneDOWN]=classifier

In some embodiments, the test compound is an inhibitory nucleic acid.

In some embodiments, the methods include administering the selected candidate compound to an animal model of FSHD, wherein the animal model comprises at least one chimeric muscle tissue comprising cells from a subject affected with FSHD; performing an assay to determine a level of expression of at least one gene selected from the group consisting of SLC34A2, TRIM49, TRIM43, PRAMEF1, CD177, NAAA, HSPA6, TC2N, CD34, ATP2A1, PAX7, MYF5, MRAP2, DAG1, CLYBL, CALCRL, ZNF445, SPATA17; comparing the level of expression of the at least one gene to a reference level of expression that represents a level of expression in the absence of the candidate compound; selecting as a candidate therapeutic compound a candidate compound that reduces the level of expression of one or more of SLC34A2, TRIM49, TRIM43, PRAMEF1, CD177, NAAA, HSPA6, TC2N, or CD34, and increases the level of expression one or more of ATP2A1, PAX7, MYF5, MRAP2, DAG1, CLYBL, CALCRL, ZNF445, or SPATA17.

In some embodiments, the methods include administering the selected candidate compound to an animal model of FSHD, wherein the animal model comprises at least one chimeric muscle tissue comprising cells from a subject affected with FSHD; evaluating an effect of the candidate compound on a biological function associated with FSHD in the animal model; and selecting as a candidate therapeutic compound a candidate compound that improves the biological function (i.e., effects a return to normal or near normal function) in the animal model.

In some embodiments, biological function is assayed using live cell imaging, muscle fiber turnover, the number of muscle stem cells, or biomarker expression.

In another aspect, the invention provides methods for treating FSHD in a subject, the method comprising administering to the subject one or more inhibitory nucleic acids targeting one or more of SLC34A2, TRIM49, TRIM43, CD177, NAAA, HSPA6, TC2N, or CD34. In an additional aspect, the invention provides methods for treating FSHD in a subject, the method comprising administering to the subject two or more inhibitory nucleic acids targeting two or more of SLC34A2, TRIM49, TRIM43, PRAMEF1, CD177, NAAA, HSPA6, TC2N, or CD34. In some embodiments, the inhibitory nucleic acid is a double-stranded RNA, siRNA, shRNA, or antisense oligonucleotide, e.g., a morpholino oligonucleotide.

Also provided herein are inhibitory nucleic acids targeting SLC34A2, TRIM49, TRIM43, CD177, NAAA, HSPA6, TC2N, or CD34 for treating FSHD, and the use of such inhibitory nucleic acids for treating FSHD, as well as for the manufacture of a medicament for the treatment of FSHD.

In another aspect, the invention provides cell lines, e.g., shown in FIG. 1, optionally selected from the group consisting of cell lines designated 07A, 07U, 09A, 09U, 12A, 12U, 15A, 15B, 15V, 21B, or 21U, where A and B designate cells from genetically affected persons with FSHD, and U and V designate genetically unaffected family members of the persons with FSHD.

In another aspect, the invention provides kits including a plurality of cell lines, e.g., a pair or trio of cell lines, from a family cohort as shown in FIG. 1, wherein the kit includes at least one cell line from a genetically affected person with FSHD, and at least one cell line from a genetically unaffected family member, e.g., a first degree relative, of the person with FSHD. In some embodiments, the kit comprises pairs or trios of cell lines selected from the group consisting of: 07A, 07U; 09A, 09U; 12A, 12U; 15A, 15B, 15V; and 21B, 21U; where A and B designate cells from genetically affected persons with FSHD, and U and V designate genetically unaffected family members of the persons with FSHD.

In one aspect, the invention features a panel of isolated biomarkers including a DUX4 nucleic acid molecule and one or more (e.g., 2, 3, 4, 5, 6, 7, 8, 9, 10, 11, 12, 13, 14, 15, 16, 17, 18, 19 or 20) additional biomarkers including any one or more of the biomarkers listed in Table 2 or 4.

In another aspect, the invention features a microarray containing at least a DUX4 nucleic acid molecule and one or more polynucleotides listed in Table 2 or 4 or their encoded polypeptides, or fragments thereof, fixed to a solid support. In one embodiment, the solid support is a membrane, bead, biochip, multiwell microtiter plate, or a resin.

In another aspect, the invention features a method of characterizing Facioscapulohumeral muscular dystrophy (FSHD) in a cell derived from an FSHD affected subject, the method involving determining the level of expression of one or more nucleic acid molecules listed in Table 2 or 4 or their encoded polypeptides in the cell relative to the level of expression of the nucleic acid molecules or polypeptides in a cell obtained from a first degree relative of the subject who does not have FSHD, thereby characterizing FSHD in the cell. In one embodiment, the method identifies the molecular biomarker profile of the cell. In another embodiment, the cells are in vitro or in vivo. In another embodiment, the FSHD subject is identified as having a contracted 4q D4Z4 region in combination with a 4qA telomeric allele.

In another aspect, the invention features a set of cell cultures, containing one culture containing cells derived from a subject identified as having FSHD and at least one control culture containing cells derived from a first degree relative of the subject that does not have FSHD. In one embodiment, the set comprises two, three or four control cultures obtained from first degree relatives of the subject. In another embodiment, the cell cultures are enriched for myogenic cells. In another embodiment, the cells are isolated by selecting cells positive for human CD56. In another embodiment, the cells are obtained from skeletal muscle biopsies. In another embodiment, the biopsy is of a bicep or deltoid muscle. In another embodiment, the FSHD subject is identified as having a contracted 4q D4Z4 region in combination with a 4qA telomeric allele, and the first degree relative does not have the contracted 4q D4Z4 region.

In another aspect, the invention features a collection containing two or more sets of the cell cultures of any previous aspect or any other aspect of the invention delineated herein, where each set comprises a culture containing cells obtained from a distinct FSHD affected subject and at least one control culture containing cells obtained from that FSHD affected subject's first degree relatives.

In another aspect, the invention features a method for identifying an FSHD biomarker, the method involving comparing the expression of one or more polynucleotides in cells derived from a subject having FSHD relative to the expression of the polynucleotide in control cells derived from a first degree relative of the subject, where an increase or decrease in the polynucleotides relative to the control identifies the polynucleotide as an FSHD biomarker.

In another aspect, the invention features a chimeric mouse containing at least one human cell derived from an FSHD affected subject or a first degree relative thereof.

In another aspect, the invention features a set of chimeric mice including one mouse containing a human cell of an FSHD affected subject, and at least one mouse containing a human cell derived from a first degree relative of the FSHD affected subject.

In another aspect, the invention features a method of identifying an agent that ameliorates FSHD in a subject in need thereof, the method involving contacting a cell derived from an FSHD affected subject with a candidate agent, and comparing the cell's biological function or the level of expression of a nucleic acid molecule of Table 2 or 4 with the biological activity or the level of expression of the nucleic acid molecule in a control cell, where an agent that normalizes the expression of the nucleic acid molecule or enhances biological function ameliorates FSHD. In one embodiment, the control cell is derived from a first degree relative of the affected.

In another aspect, the invention features a method of identifying an agent that ameliorates FSHD in a subject in need thereof, the method involving administering the agent to the chimeric mouse of any previous aspect, and comparing the biological function of a human cell of the mouse before and after treatment, where an agent that enhances the biological function of the cell is identified as ameliorating FSHD.

In another aspect, the invention features a method of identifying an agent that ameliorates FSHD in a subject in need thereof, the method involving administering the agent to the chimeric mouse of any previous aspect, and comparing the level of expression of a nucleic acid molecule of Table 2 or 4 in a human cell of the mouse relative to the level in an untreated control cell, where an agent that normalizes expression in the cell is identified as ameliorating FSHD.

In another aspect, the invention features a method of identifying an inhibitory nucleic acid that ameliorates FSHD in a subject in need thereof, the method involving contacting a cell derived from an FSHD affected subject with an inhibitory nucleic acid molecule that targets a polynucleotide over expressed in FSHD, and comparing the level of expression of the polynucleotide relative to the level in a reference, where an inhibitory nucleic acid molecule that reduces expression of the polynucleotide ameliorates FSHD.

In another aspect, the invention features a method of identifying an inhibitory nucleic acid that ameliorates FSHD in a subject in need thereof, the method involving contacting a cell derived from an FSHD affected subject with an inhibitory nucleic acid molecule that targets a polynucleotide over expressed in FSHD, and comparing the biological function of a human cell of the mouse before and after treatment, where an agent that enhances the biological function of the cell is identified as ameliorating FSHD.

In another aspect, the invention features a method of diagnosing a subject as having, or having a propensity to develop, Facioscapulohumeral muscular dystrophy (FSHD), the method involving determining the level of expression of one or more nucleic acid molecules listed in Table 2 or 4 or their encoded polypeptides in a biological sample of the subject relative to the level of expression of the nucleic acid molecules or polypeptides in a reference, where an alteration in the level of expression is indicative of FSHD.

In various embodiments of the previous aspects or any other aspect of the invention delineated herein, the panel includes polynucleotide or polypeptide biomarkers that are any one or more of DUX4, tripartite motif containing 43 (TRIM43), TRIM49, tandem C2 domains, nuclear (TC2N), PRAME family member 13 (PRAMEF13), PRAMEF2, PRAMEF1, solute carrier family 34 (SLC34A2), heat shock 70 kDa protein 6 (HSP70B), FLJ44674 protein, CD177, and chromosome 9 open reading frame 4 (C9orf4). In one embodiment, the panel includes or consists of DUX4 and one or more additional upregulated biomarkers selected from the group consisting of TRIM43, PRAMEF13, PRAMEF2, PRAMEF1, SLC34A2, TRIM49, CCNA1, and TNXA. In another embodiment, the panel comprises DUX4 and a downregulated biomarker selected from the group consisting of microRNA 30b (MIR30B), dystroglycan 1 (DAG1), melanocortin 2 receptor accessory protein (MRAP2), chromosome 9 open reading frame 153 (C9orf153), ATPase, Ca++ transporting, cardiac (ATP2A1), citrate lyase beta like (CLYBL), calcitonin receptor-like (CALCRL), cytochrome P450, family 39, subfamily (CYP39A1), mastermind-like 3 (MAML3), adrenergic, beta, receptor kinase 2 (ADRBK2), Rho guanine nucleotide exchange factor (ARHGEF7), microRNA 95 (miR95), spermatogenesis associated 17 (SPATA17), islet cell autoantigen 1.69 kDa-like (ICA1L), GABRR1, gamma-aminobutyric acid (GABA) KIAA1217, zinc finger protein 445 (ZNF445), and chromosome 14 open reading frame 39 (C14orf39). In another embodiment, the panel comprises or consists of DUX4 and a downregulated biomarker selected from the group consisting of CALCRL, ATP2A1, MYLK4, E2F8, RGS13, MYOZ2, LRRC39, C6orf142, and MYOZ1. In other embodiments, the human cell is a skeletal muscle cell, muscle stem cell, or differentiated muscle fiber. In other embodiments, the human cells replace 1-100% (e.g., 5%, 10%, 20%, 30%, 40%, 50%, 60%, 70%, 80%, 90%, 100%) of the cells present in a muscle of the mouse. In one embodiment, the human cells replace cells present in the tibialis anterior. In still other embodiments, biological function is assayed using live cell imaging, muscle fiber turnover, the number of muscle stem cells, or biomarker expression.

The invention provides compositions and methods for characterizing FSHD in a subject, as well as compositions and methods useful in drug screening. Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "biomarker" is meant a polypeptide, polynucleotide, or clinical criteria associated with a disease or condition. For example, an alteration in the presence, level of expression, or sequence of a biomarker may be associated with or diagnostic of a disease or condition.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "cell culture" is meant a cell or cells in vitro. A cell culture includes a cell growing or capable of growing in vitro. Thus, a cell culture includes frozen cells capable of growth in vitro.

"Detect" refers to identifying the presence, absence or amount of the analyte to be detected.

By "detectable label" is meant a composition that when linked to a molecule of interest renders the latter detectable. Exemplary methods used to detect a detectable label, include spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat a condition or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "Marker profile" is meant a characterization of the expression or expression level of two or more polypeptides or polynucleotides.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers. In particular embodiments, primers of the invention are useful in amplifying a gene listed in Table 2 or 4.

By "reduces" is meant a negative alteration of at least 10%, 25%, 50%, 75%, or 100%.

By "reference" is meant a standard or control condition. For example, the level of a polynucleotide or polypeptide of the invention (e.g., a polynucleotide listed in Table 2 or 4 or the encoded polypeptide) in a subject that is not affected with FSHD, such as a first degree relative of the subject.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "a set" is meant a group having more than one member. The group may be composed of 2, 4, 5, 8, 10, 20, 30, 40, 50, 60, 70, 80, 90, 100, 125, 150, 200, 250, or 300 polypeptide, nucleic acid molecule, cell culture, or chimeric mouse members.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity. In one embodiment, the invention provides siRNA that target a polynucleotide of the invention (e.g., a polynucleotide upregulated in FSHD).

By "specifically binds" is meant a compound or antibody that recognizes and binds a polypeptide of the invention, but which does not substantially recognize and bind other molecules in a sample, for example, a biological sample, which naturally includes a polypeptide of the invention. In one embodiment, the invention provides antibodies against polypeptides, or fragments thereof, encoded by a gene listed in Table 2 or 4.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 shows a table of cell lines as described herein. Each cohort was composed of at least one affected individual with genetically and clinically verified FSHD (designated A or B), and at least one unaffected first degree relative with unshortened D4Z4 alleles and normal strength (designated U or V).

DETAILED DESCRIPTION OF THE INVENTION

The invention provides compositions and methods that are useful treating Facioscapulohumeral muscular dystrophy (FSHD), and methods of identifying new treatments for FSHD.

The invention is based, at least in part, on the discovery of genes whose expression is aberrantly regulated in cells derived from subjects having FSHD (e.g., genes listed in Tables 2 and 4). In certain embodiments, a subset of genes is identified whose expression is most robustly altered in FSHD affected subjects (e.g. 20 genes in Table 2 with smallest p-values among those genes upregulated in FSHD and 20 genes in Table 2 with smallest p-values among those genes downregulated in FSHD). Genes whose expression is altered in FSHD are useful as biomarkers in methods for diagnosing or characterizing FSHD. Thus, the invention provides panels comprising FSHD biomarkers, as well as polynucleotide and polypeptide microarrays comprising such biomarkers.

The discovery of FSHD biomarkers was made possible using a unique collection of cultured cells derived from the skeletal muscles of subjects affected by FSHD, as well as of their first degree relatives. These "FSHD paired cultures" provide a unique advantage not only in identifying genes that are aberrantly regulated in FSHD, but also in identifying and/or assessing the efficacy of therapeutic agents useful in ameliorating FSHD or symptoms thereof. These FSHD paired cultures provide a unique advantage over other cells derived from FSHD affected subjects because they control for familial relationships by comparing expression differences in related FSHD affected subjects and controls, thereby diminishing the effects of interindividual variation on gene expression. Therefore, the expression differences observed between FSHD and control muscles in these FSHD paired cultures likely reflect true pathogenic gene expression profiles suitable for developing into disease biomarkers. The invention further provides screening methods using collections of FSHD paired cultures to identify agents that modify the expression of genes and/or proteins that are aberrantly regulated in FSHD.

In other embodiments, the invention provides pairs of chimeric mice, wherein one member of the pair comprises cells derived from a subject affected by FSHD, and the other member of the pair comprises a cell derived from a first degree relative of the subject. In other embodiments, the invention provides two, three, four or more mice, where one mouse comprises cells from an FSHD affected subject, and the other mice comprises cells derived from one or more of the first degree relatives of that subject. Preferably, certain skeletal muscle cells of the mouse are derived from an FSHD subject or first degree relative of such a subject. Thus, the invention provides a mouse model that is uniquely suited for the identification and characterization of agents useful in treating and/or ameliorating FSHD, and or symptoms thereof.

In still other embodiments, the invention provides panels of biomarkers comprising at least 2, 3, 5, 10, 15, 20, or more of the genes listed in Table 2 or 4. In one embodiment, the panel comprises those genes identified as upregulated in FSHD. In another embodiment, the panel comprises those genes identified as downregulated in FSHD.

Facioscapulohumeral Muscular Dystrophy

Facioscapulohumeral muscular dystrophy (FSHD) is an autosomal dominant muscular dystrophy affecting approximately 1 in 7,000-20,000 individuals. It is characterized by progressive weakness and wasting of facial, shoulder girdle and upper arm muscles from which the disease takes its name, and also trunk, hip and leg muscles in some patients. One of the hallmarks of FSHD is asymmetrical and selective degeneration of skeletal muscles. For example, biceps muscle is involved early and severely, whereas the proximal deltoid muscle is relatively spared. The underlying mechanism of this distinctive sparing of certain muscle types is unknown. In addition to muscle degeneration, abnormalities in retinal vasculature and hearing loss are observed in up to 49% and 64% respectively in some populations.

FSHD is caused by partial deletion of a critical number of repeat elements within the highly polymorphic macrosatellite D4Z4 on the subtelomeric region of chromosome 4q. In unaffected individuals, the D4Z4 array consists of 11 to 100 repeats (corresponding to EcoRI fragments of 41 to 350 kb), whereas FSHD patients carry 1 to 10 repeats (corresponding to EcoRI fragments of 10 to 35 kb). Longer residual repeat sizes are often associated with later onset or milder disease severity. In addition to reduction of the tandemly arranged D4Z4 3.3 kb repeat units, the disease causing deletions must occur on chromosomal allele 4qA, whereas deletions on the equally common 4qB allele do not result in FSHD. Although the genetic lesion responsible for 95% of FSHD cases was identified two decades ago, the molecular mechanisms leading to disease progression have long been controversial. The predominantly held position-effect variegation hypothesis proposed that contraction of the D4Z4 repeats induces depression of one or more genes adjacent to D4Z4 with myopathic potential. Several genes (FRG1, FRG2, SLC25A4) residing in the vicinity of D4Z4 have been evaluated using various quantitative approaches by numerous studies but no consistent deregulation of these genes have been demonstrated in human muscle (Winokur et al., (2003) Hum Genet, 12, 2895-2907; Osborne (2007) Neurology, 68, 569-577; Masny et al., (2010) Eur J Hum Genet, 18, 448-456).

DUX4

Several studies have demonstrated the myopathic potential of DUX4, a gene located within each repeat element, in skeletal muscle cells. Overexpression of DUX4, as a result of chromatin relaxation within D4Z4, was initially proposed to induce toxicity to muscle cells, potentially leading to muscle degeneration in vivo. Subsequent studies demonstrated further evidence to support this finding. Recently, genetic analysis of rare families carrying translocations between 4q and 10q chromosomes identified single nucleotide polymorphisms (SNPs) in the pLAM region adjacent to the distal D4Z4 repeat that segregate with FSHD. These SNPs create a canonical polyadenylation signal on the permissive chromosomal allele, whereas the non-permissive alleles lack these SNPs. DUX4 transcripts expressed from the distal-most repeat extends into the pLAM sequence and are polyadenylated when the poly(A) signal SNPs are incorporated into the transcripts, thus increasing their intracellular stability. DUX4, a double homeodomain containing protein, shares similarities with transcription factors PAX3 and PAX7 and is proposed to interfere with transcriptional networks regulated by PAX3/7. It has yet to be determined whether DUX4 overexpression results in global gene misexpression, and in particular it is of considerable interest to determine whether the expression of PAX3/7 target genes are compromised in FSHD muscles, as these transcription factors play an important role in muscle development and maintenance. In view of these findings, agents that reduce DUX4 expression are of interest in treating FSHD and/or ameliorating symptoms associated with FSHD. The analysis of such agents has been hampered by the lack of suitable in vitro and in vivo models systems useful for assaying the efficacy of such agents on FSHD. Thus, the invention provides cell and animal models useful for analysing the agents that treat FSHD. In particular, FSHD paired cultures are useful for analysing the effect of such agents on the expression of genes that are aberrantly regulated in FSHD. In other embodiments, chimeric FSHD mice of the invention are useful for assaying the efficacy of such agents on muscle cells affected with FSHD. In particular, the invention provides methods for assaying the effects of agents that reduce DUX4 expression on genes that are aberrantly regulated in FSHD (e.g., genes listed in Table 2 or 4).

FSHD Cell Cultures and Collections

While the results reported herein provide specific examples of the isolation of muscle cells from subjects identified as having FSHD (or their first degree relatives) during the course of a muscle biopsy, the invention is not so limited. The unpurified source of cells for use in the methods of the invention may be any tissue known in the art obtained from an FSHD subject, although preferably, muscle cells derived from FSHD affected subjects are used. In various embodiments, cells of the invention are isolated from muscle tissue whose biological function is reduced in FSHD (e.g., adult biceps or deltoid skeletal muscles). In one embodiment, the FSHD subject is identified as having a contracted 4q D4Z4 region in combination with a 4qA telomeric allele and the first degree relative is identified as lacking such genetic abnormalities.

The invention provides for the generation of primary muscle cell cultures. Such cultures are obtained by enzymatic dissociation of the tissue using, for example, collagenase IV, dispase and other enzymes known in the art. The cells can be selected against dead cells, by employing dyes associated with dead cells such as propidium iodide (PI). Preferably, the cells are collected in a medium comprising fetal calf serum (FCS) or bovine serum albumin (BSA) or any other suitable, preferably sterile, isotonic medium. Dissociated cells are cultured under standard conditions using cell culture media (e.g., Ham's F10 medium supplemented with fetal bovine serum and/or chicken embryo extract) suitable for maintaining cultures of primary muscle cells. Examples of suitable media for incubating cells of the invention include, but are not limited to, Dulbecco's Modified Eagle Medium (DMEM), RPMI media or other medias known in the art. The media may be supplemented with fetal calf serum (FCS) or fetal bovine serum (FBS), as well as antibiotics, growth factors, amino acids, inhibitors or the like, which is well within the general knowledge of the skilled artisan.

Cultures are expanded to increase cell number (e.g., to about 50%, 60%, 70%, 80% confluence). Cells are harvested and selected for myogenic cells using standard methods. Such methods include a positive selection for cells expressing one or more myogenic markers. Monoclonal antibodies are particularly useful for identifying markers associated with the desired cells. If desired, negative selection methods can be used in conjunction with the methods of the invention to reduce the number of irrelevant cells present in a population of cells selected for a myogenic phenotype.

In one approach, fluorescence-activated cell sorting (FACS) is carried out to identify cells that are positive for human CD56 (BD Biosciences), MYOD, PAX7, or MYF5. In another approach, magnetic-activated cell sorting (MACS) is used to select for the desired cell type. Other procedures which may be used for selection of cells of interest include, but are not limited to, fluorescence based cell sorting, density gradient centrifugation, flow cytometry, magnetic separation with antibody-coated magnetic beads, cytotoxic agents joined to or used in conjunction with a mAb, including, but not limited to, complement and cytotoxins; and panning with antibody attached to a solid matrix or any other convenient technique.

CD56-positive myogenic cells obtained by FACS are incubated in culture. Cells derived from the skeletal muscles of subjects affected by FSHD, as well as of their first degree relatives are termed "FSHD paired cultures." In one embodiment, such paired cultures are useful in identifying markers that are aberrantly regulated in FSHD. In another embodiment, such cells are useful in identifying and/or assessing the efficacy of therapeutic agents useful in ameliorating FSHD or symptoms thereof. These FSHD paired cultures provide for the analysis of expression differences in related FSHD affected subjects and controls, thereby diminishing the effects of interindividual variation on gene expression.

Selected cells of the invention may be employed in methods of the invention following isolation and/or growth in vitro.

In one approach, the invention provides paired cell cultures, where one culture is derived from a subject having FSHD and the other culture is obtained from a first degree relative of the subject. Such paired cell cultures comprise skeletal muscle cells isolated from the subject or his relative during muscle biopsy. Such cells are then cultured in vitro to obtain sufficient cells for drug screening or marker expression analysis. The invention further provides a collection of such paired cell cultures. Desirably, the collection includes cell samples from two, three, four, five, six, seven, eight, nine, ten or more FSHD affected subjects and paired control cultures obtained from one or more of the subjects first degree relatives. In certain embodiments, the invention provides a frozen collection of cells suitable for paired culture. Frozen cell compositions typically comprise cryoprotective agents that provide for cell viability when the cells are frozen for a period of months or years and then subsequently thawed.

FSHD Chimeric Animals

The invention further provides chimeric animals that comprise human cells obtained from an FSHD affected. Preferably, the invention provides pairs of chimeric mice, wherein one member of the pair comprises human cells obtained from an FSHD affected and the other member of the pair comprises human cells obtained from a first degree relative of the FSHD affected.

In one embodiment, skeletal muscle cells of a mouse are injured or destroyed, for example, using cardiotoxin. The skeletal muscle cells of the injured mouse are replaced with at least about 10%, 20%, 30%, 50%, 75% or even 100% human cells derived from an FSHD subject. In one embodiment, the mouse's endogenous tibialis anterior is replaced, at least to some degree, with human muscle cells derived from an FSHD affected or a first degree relative thereof. If desired, such cells are genetically modified to express a detectable reporter (e.g., GFP, YFP, RFP, luciferase).

In one embodiment, the method provides chimeric animals, wherein one animal comprises cells of an FSHD affected and one or more other animals comprises cells of a first degree relative of the affected individual. Such chimeric animals are useful in identifying markers that are aberrantly regulated in FSHD. The invention provides a collection of such paired chimeric mice. Desirably, the collection includes cell samples from two, three, four, five, six, seven, eight, nine, ten or more FSHD affected subjects and paired control chimeric mice comprising cells obtained from one or more of the subjects' first degree relatives.

Diagnostics

The present invention features diagnostic assays for the detection of FSHD or the propensity to develop such conditions. In one embodiment, levels of any one or more of the markers listed in Table 2 or 4 are measured in a subject sample and used to characterize FSHD or the propensity to develop FSHD. In other embodiments, levels of markers listed in Table 2 or 4, are characterized in a subject sample. Standard methods may be used to measure levels of a marker in any biological sample. Biological samples include tissue samples (e.g., cell samples, biopsy samples) or biological fluid samples that include markers of the invention (e.g., blood, serum, plasma, urine). Methods for measuring levels of polypeptide biomarkers of the invention (e.g., markers listed in Table 2 or 4) include immunoassay, ELISA, western blotting and radioimmunoassay. The increase in marker levels may be altered (e.g., increased, decreased) by at least about 10%, 25%, 50%, 75% or more relative to levels of markers found in a corresponding control sample (e.g., samples obtained from a normal subject unaffected by FSHD). In one embodiment, any increase or decrease in a marker of the invention, i.e., a marker listed in Table 2 or 4, is indicative of FSHD.

Any suitable method can be used to detect one or more of the markers described herein. Successful practice of the invention can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$, quadrupole mass spectrometry, fourier transform mass spectrometry (FTMS), and ion trap mass spectrometry, where n is an integer greater than zero.

Detection methods may include use of a biochip array. Biochip arrays useful in the invention include protein and polynucleotide arrays. One or more markers are captured on the biochip array and subjected to analysis to detect the level of the markers in a sample.

Markers may be captured with capture reagents immobilized to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure the serum peptide marker. The method may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from Perseptive Biosystems, Inc. (Frazingham, Mass., USA) and are described in the literature, e.g. M. Kussmann and P. Roepstorff, cited above.

Magnetic-based serum processing can be combined with traditional MALDI-TOF. Through this approach, improved peptide capture is achieved prior to matrix mixture and deposition of the sample on MALDI target plates. Accordingly, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the invention to produce an array of spots on the collecting membrane, and the array may be analyzed. Subsequently, automated output of the results is provided by using the ExPASy server, as at present used for MIDI-TOF MS and to generate the data in a form suitable for computers.

Other techniques for improving the mass accuracy and sensitivity of the MALDI-TOF MS can be used to analyze the fragments of protein obtained on the collection membrane. These include the use of delayed ion extraction, energy reflectors and ion-trap modules. In addition, post source decay and MS-MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS-MS or MS$^n$ analysis to be performed. Tandem mass spectrometry allows multiple reactions to be monitored at the same time.

Capillary infusion may be employed to introduce the marker to a desired MS implementation, for instance, because it can efficiently introduce small quantities of a sample into a mass spectrometer without destroying the vacuum. Capillary columns are routinely used to interface the ionization source of a MS with other separation techniques including gas chromatography (GC) and liquid chromatography (LC). GC and LC can serve to separate a solution into its different components prior to mass analysis. Such techniques are readily combined with MS, for instance. One variation of the technique is that high performance liquid chromatography (HPLC) can now be directly coupled to mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem MS experiments. FTMS is based on the principle of a charged particle orbiting in the presence of a magnetic field. Coupled to ESI and MALDI, FTMS offers high accuracy with errors as low as 0.001%.

In one embodiment, the marker qualification methods of the invention may further comprise identifying significant peaks from combined spectra. The methods may also further comprise searching for outlier spectra. In another embodiment, the method of the invention further comprises determining distant dependent K-nearest neighbors.

In another embodiment of the method of the invention, an ion mobility spectrometer can be used to detect and characterize FSHD markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

In an additional embodiment of the methods of the present invention, multiple markers are measured. The use of multiple markers increases the predictive value of the test and provides greater utility in diagnosis, toxicology, patient stratification and patient monitoring. The process called "Pattern recognition" detects the patterns formed by multiple markers greatly improves the sensitivity and specificity of clinical proteomics for predictive medicine. Subtle variations in data from clinical samples indicate that certain patterns of protein expression can predict phenotypes such as the presence or absence of FSHD.

Expression levels of particular nucleic acids or polypeptides are correlated with FSHD, and thus are useful in diagnosis. Antibodies that bind a polypeptide described herein, oligonucleotides or longer fragments derived from a nucleic acid sequence described herein (e.g., one or more Markers listed in Table 2 or 4), or any other method known in the art may be used to monitor expression of a polynucleotide or polypeptide of interest. Detection of an alteration relative to a normal, reference sample can be used as a diagnostic indicator of FSHD. In particular embodiments, the expression of one or more Markers listed in Table 2 or 4 is indicative of FSHD or the propensity to develop FSHD. In other embodiments, a 2, 3, 4, 5, or 6-fold change in the level of a marker of the invention is indicative of FSHD. In yet another embodiment, an expression profile that characterizes alterations in the expression of two, three, four, five, ten, fifteen, twenty, thirty, or forty markers is correlated with a particular disease state (e.g., FSHD). Such correlations are indicative of FSHD or the propensity to develop FSHD. In one embodiment, FSHD can be monitored using the methods and compositions of the invention.

In one embodiment, the level of one or more markers is measured on at least two different occasions and an alteration in the levels as compared to normal reference levels over time is used as an indicator of FSHD or the propensity to develop FSHD. The level of marker in a subject having FSHD or the propensity to develop such a condition may be altered by as little as 10%, 20%, 30%, or 40%, or by as much as 50%, 60%, 70%, 80%, or 90% or more relative to the level of such marker in a normal control. In general, levels of Markers listed in Table 2 or 4 are present at low or undetectable levels in a healthy subject (i.e., those who do not have and/or who will not develop FSHD). In one embodiment, a subject sample of a skeletal muscle (e.g., bicep) is collected prior to the onset of symptoms of FSHD or early on in the progression of FSHD.

The diagnostic methods described herein can be used individually or in combination with any other diagnostic method described herein for a more accurate diagnosis of the presence or severity of FSHD.

The diagnostic methods described herein can also be used to monitor and manage FSHD, or to reliably distinguish FSHD from other degenerative diseases or diseases having symptoms that are similar to or overlap with FSHD.

As indicated above, the invention provides methods for aiding a muscular dystrophy (e.g., FSHD) diagnosis using one or more markers, as specified herein. These markers can be used alone, in combination with other markers in any set, or with entirely different markers in aiding human muscular dystrophy (e.g., FSHD) diagnosis. The markers are differentially present in samples of a human FSHD patient and a normal subject (e.g., first degree relative of an FSHD subject) in whom FSHD is undetectable. Therefore, detection of one or more of these markers in a person would provide useful information regarding the probability that the person may have FSHD or have a propensity to develop FSHD.

The detection of one or more peptide marker is then correlated with a probable diagnosis of FSHD. In some embodiments, the detection of the mere presence of a marker (e.g., a marker listed in Table 2 or 4), without quantifying the amount thereof, is useful and can be correlated with a probable diagnosis of FSHD. The measurement of markers may also involve quantifying the markers to correlate the detection of markers with a probable diagnosis of FSHD. Thus, if the amount of the markers detected in a subject being tested is different compared to a control amount (i.e., higher or lower than the control), then the subject being tested has a higher probability of having FSHD.

The correlation may take into account the amount of the marker or markers in the sample compared to a control amount of the marker or markers (e.g., in normal subjects). A control can be, e.g., the average or median amount of marker present in comparable samples of normal subjects. The control amount is measured under the same or substantially similar experimental conditions as in measuring the test amount. As a result, the control can be employed as a reference standard, where each result can be compared to that standard, rather than re-running a control.

Accordingly, a marker profile may be obtained from a subject sample and compared to a reference marker profile, so that it is possible to classify the subject as having or not having FSHD. The correlation may take into account the presence or absence of the markers in a test sample and the frequency of detection of the same markers in a control. The correlation may take into account both of such factors to facilitate determination of FSHD status.

In certain embodiments of the invention, the methods further comprise managing subject treatment based on the status.

The markers of the present invention have a number of other uses. For example, they can be used to identify agents useful in methods of treating or ameliorating FSHD. In yet another example, the markers can be used in heredity studies. For instance, certain markers associated with FSHD may be genetically associated with the disease. This can be determined by, e.g., analyzing samples from a population of human subjects whose families have a history of FSHD. The results can then be compared with data obtained from, e.g., subjects whose families do not have a history of FSHD. The markers that are genetically linked may be used as a tool to determine if a subject whose family has a history of FSHD is pre-disposed to having FSHD.

While individual markers are useful diagnostic markers, in some instances, a combination of markers provides greater predictive value than a single marker alone. The detection of a plurality of markers (or absence thereof, as the case may be) in a sample can increase the percentage of true positive and true negative diagnoses and decrease the percentage of false positive or false negative diagnoses. Thus, preferred methods of the present invention comprise the measurement of more than one marker.

Microarrays

As reported herein, a number of markers (e.g., a marker listed in Table 2 or 4) have been identified that are associated with FSHD. Methods for assaying the expression of these polypeptides are useful for characterizing FSHD. In particular, the invention provides diagnostic methods and compositions useful for identifying a polypeptide expression profile that identifies a subject as having or having a propensity to develop FSHD. Such assays can be used to measure an alteration in the level of a polypeptide.

The polypeptides and nucleic acid molecules of the invention are useful as hybridizable array elements in a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Protein Microarrays

Proteins (e.g., proteins encoded by genes listed in Table 2 or 4) may be analyzed using protein microarrays. Such arrays are useful in high-throughput low-cost screens to identify alterations in the expression or post-translation modification of a polypeptide of the invention, or a fragment thereof. In particular, such microarrays are useful to identify a protein whose expression is altered in FSHD. In one embodiment, a protein microarray of the invention binds a marker present in a subject sample and detects an alteration in the level of the marker. Typically, a protein microarray features a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., antibodies that bind a marker of the invention) are spotted on a substrate using any convenient method known to the skilled artisan (e.g., by hand or by inkjet printer).

The protein microarray is hybridized with a detectable probe. Such probes can be polypeptide, nucleic acid molecules, antibodies, or small molecules. For some applications, polypeptide and nucleic acid molecule probes are derived from a biological sample taken from a patient, such as a homogenized tissue sample (e.g. a tissue sample obtained by muscle biopsy); or a cell isolated from a patient sample. Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Nucleic Acid Microarrays

To produce a nucleic acid microarray, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, as a tissue sample (e.g. a tissue sample obtained by muscle biopsy). For some applications, cultured cells or other tissue preparations may be used. The mRNA is isolated according to standard methods, and cDNA is produced and used as a template to make complementary RNA suitable for hybridization. Such methods are known in the art. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30 C., more preferably of at least about 37 C., and most preferably of at least about 42 C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30 C in 750 mM NaCl, 75 mM trisodium citrate, and 1% SDS. In a more preferred embodiment, hybridization will occur at 37 C. in 500 mM NaCl, 50 mM trisodium citrate, 1% SDS, 35% formamide, and 100 µg/ml denatured salmon sperm DNA (ssDNA). In a most preferred embodiment, hybridization will occur at 42 C in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25 C., more preferably of at least about 42° C., and most preferably of at least about 68 C. In a preferred embodiment, wash steps will occur at 25 C in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a most preferred embodiment, wash steps will occur at 68 C in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct nucleic acid sequences simultaneously (e.g., Heller et al., Proc. Natl. Acad. Sci. 94:2150-2155, 1997). Preferably, a scanner is used to determine the levels and patterns of fluorescence.

Diagnostic Kits

The invention provides kits for diagnosing or monitoring FSHD. In one embodiment, the kit includes a composition containing at least one agent that binds a polypeptide or polynucleotide whose expression is increased in FSHD. In another embodiment, the invention provides a kit that contains an agent that binds a nucleic acid molecule whose expression is altered in FSHD. In some embodiments, the kit comprises a sterile container which contains the binding agent; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the kit is provided together with instructions for using the kit to diagnose FSHD. The instructions will generally include information about the use of the composition for diagnosing a subject as having FSHD or having a propensity to develop FSHD. In other embodiments, the instructions include at least one of the following: description of the binding agent; warnings; indications; counter-indications; animal study data; clinical study data; and/or references. The instructions may be printed directly on the container (when present), or as a label applied to the container, or as a separate sheet, pamphlet, card, or folder supplied in or with the container.

Screening Assays

As discussed herein, the expression of genes listed in Tables 2 and 4 is altered in FSHD. Based on this discovery, compositions of the invention are useful for the high-throughput low-cost screening of candidate agents to identify those that modulate the expression of genes that are aberrantly expressed in FSHD. In one embodiment, the effects of candidate agents on genes expressed in Tables 2 and 4 are assayed using microarrays, cell compositions, and/or chimeric animals of the invention.

Those genes identified in Tables 2 or 4 whose expression is inappropriately increased in FSHD are targets for therapeutic intervention. The genes TRIM43 and PRAMEF1 are of particular interest. The inappropriate activation of one or more genes upregulated in FSHD likely contributes to the pathology observed in FSHD. Therefore, agents that reduce the expression of genes that are over-expressed in FSHD are useful in the methods of the invention. Such agents include, for example, inhibitory nucleic acids that reduce or eliminate the expression of such genes, as well as proteins (e.g., antibodies and fragments thereof) and small compounds that interfere with the expression or biological activity of the genes or the proteins that they encode. The present methods can be used to identify such agents.

Those genes identified in Table 2 or 4 whose expression is inappropriately decreased in FSHD are also targets for therapeutic intervention. Such agents include, for example, small compounds that increase the biological activity or expression of a gene listed in Table 2 or 4 or of the protein that gene encodes. In other embodiments, agents (e.g., expression vectors encoding proteins downregulated in FSHD) are useful to increase the expression of such genes, particularly in skeletal muscle. Such expression would be expected to ameliorate FSHD or symptoms associated with FSHD. The present methods can be used to identify such agents.

A number of methods are available for carrying out screening assays to identify candidate agents that reduce the expression of genes that are overexpressed in FSHD, or that increase the expression of a gene that is downregulated in FSHD. In one example, candidate agents are added at varying concentrations to the culture medium of cultured cells (e.g., FSHD paired cultures) expressing one of the nucleic acid sequences of the invention. Gene expression is then measured, for example, by microarray analysis, Northern blot analysis (Ausubel et al., supra), reverse transcriptase PCR, quantitative real-time PCR, or any other method known in the art using any appropriate fragment prepared from the nucleic acid molecule as a hybridization probe. The level of gene expression in the FSHD derived cells in the presence of the candidate agent is compared to the level measured in a control culture. In one embodiment, the control culture is a culture of FSHD derived cells that lack the agent. In another embodiment, the control culture is the paired culture of cells obtained from a first degree relative of the FSHD affected. An agent that normalizes or promotes the normalization of expression of aberrantly regulated genes is considered useful in the invention. Such an agent may be used, for example, as a therapeutic to treat FSHD in a human patient. An agent that "normalizes" the expression of an aberrantly regulated gene restores the expression of that gene to a level that is substantially normal. An agent that "promotes normalization" reduces the extent of the disregulation.

In one example, the effect of candidate agents is measured at the level of polypeptide production using the same general approach and standard immunological techniques, such as Western blotting or immunoprecipitation with an antibody specific for a polypeptide encoded by a gene listed in Table 2 or 4. For example, immunoassays may be used to detect or monitor the expression of at least one of the polypeptides of the invention in an organism. Polyclonal or monoclonal antibodies, (produced as described above) that are capable of binding to such a polypeptide may be used in any standard immunoassay format (e.g., ELISA, Western blot, or RIA assay) to measure the level of the polypeptide. In some embodiments, a agent that normalizes or promotes normalization of the expression or biological activity of an aberrantly regulated polypeptide is considered useful. Again, such an agent may be used, for example, as a therapeutic to delay, ameliorate, or treat FSHD disorder, or the symptoms of FSHD, in a human patient.

In yet another working example, candidate agents may be screened for those that specifically bind to a polypeptide encoded by a gene listed in Table 2 or 4. The efficacy of such a candidate agent is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate agent may be tested in vitro for its ability to specifically bind a polypeptide of the invention. In another embodiment, a candidate agent is tested for its ability to normalize or promote the normalization of the biological activity of a polypeptide described herein. The biological activity of a polypeptide may be assayed using any standard method.

In another example, a gene described herein (e.g., listed in Table 2 or 4) is expressed as a transcriptional or translational fusion with a detectable reporter, and expressed in an isolated cell (e.g., mammalian or insect cell) under the control of a heterologous promoter, such as an inducible promoter. The cell expressing the fusion protein is then contacted with a candidate agent, and the expression of the detectable reporter in that cell is compared to the expression of the detectable reporter in an untreated control cell. A candidate agent that alters (e.g., normalizes or promotes normalization) the expression of the detectable reporter is an agent that is useful for the treatment of FSHD. In preferred embodiments, the candidate agent increases the expression of a reporter gene fused to a gene that is downregulated in FSHD.

In one particular working example, a candidate agent that binds to a polypeptide encoded by a gene listed in Table 2 or 4 may be identified using a chromatography-based technique. For example, a recombinant polypeptide of the invention may be purified by standard techniques from cells engineered to express the polypeptide (e.g., those described above) and may be immobilized on a column. A solution of candidate agents is then passed through the column, and an agent specific for the polypeptide encoded by a nucleic acid molecule listed in Table 2 or 4 is identified on the basis of its ability to bind to the polypeptide and be immobilized on the column. To isolate the agent, the column is washed to remove non-specifically bound molecules, and the agent of interest is then released from the column and collected. Similar methods may be used to isolate an agent bound to a polypeptide microarray. Agents isolated by this method (or any other appropriate method) may, if desired, be further purified (e.g., by high performance liquid chromatography). In addition, these candidate agents may be tested for their ability to increase the activity of gene whose expression is downregulated in FSHD. Agents isolated by this approach may also be used, for example, as therapeutics to treat FSHD in a human patient. Agents that are identified as binding to a polypeptide of the invention with an affinity constant less than or equal to 10 mM are considered particularly useful in the invention. Alternatively, any in vivo protein interaction detection system, for example, any two-hybrid assay may be utilized.

Potential agonists and antagonists include organic molecules, peptides, peptide mimetics, polypeptides, nucleic acid molecules, and antibodies that bind to a nucleic acid sequence or polypeptide of the invention. (e.g., those listed in Table 2 or 4). For those nucleic acid molecules or polypeptides whose expression is decreased in a patient having FSHD, agonists would be particularly useful in the methods of the invention. For those nucleic acid molecules or polypeptides whose expression is increased in a patient having FSHD, antagonists would be particularly useful in the methods of the invention.

Each of the DNA sequences identified herein may be used in the discovery and development of a therapeutic agent for the treatment of FSHD. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra). Optionally, agents identified in any of the above-described assays may be confirmed as useful in cell culture or in a chimeric animal of the invention. Small molecules of the invention preferably have a molecular weight below 2,000 daltons, more preferably between 300 and 1,000 daltons, and most preferably between 400 and 700 daltons. It is preferred that these small molecules are organic molecules.

Test Agents and Extracts

In general, agents capable of normalizing or promoting the normalization of expression of a gene listed in Table 2 or 4 are identified from large libraries of both natural product or synthetic (or semi-synthetic) extracts or chemical libraries or from polypeptide or nucleic acid libraries (e.g., Table 2 or 4), according to methods known in the art. Those skilled in the field of drug discovery and development will understand that the precise source of test extracts or agents is not critical to the screening procedure(s) of the invention. Agents used in screens may include known agents (for example, known therapeutics used for other diseases or disorders). Alternatively, virtually any number of unknown chemical extracts or agents can be screened using the methods described herein. Examples of such extracts or agents include, but are not limited to, plant-, fungal-, prokaryotic- or animal-based extracts, fermentation broths, and synthetic agents, as well as modification of existing agents. Numerous methods are also available for generating random or directed synthesis (e.g., semi-synthesis or total synthesis) of any number of chemical agents, including, but not limited to, saccharide-, lipid-, peptide-, and nucleic acid-based agents. Synthetic agent libraries are commercially available from Brandon Associates (Merrimack, N.H.) and Aldrich Chemical (Milwaukee, Wis.). Alternatively, libraries of natural agents in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or agent is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to normalize or promote normalization of the activity of a polypeptide that is aberrantly regulated in FSHD, further fractionation of the positive lead extract is necessary to isolate chemical constituents responsible for the observed effect. Thus, the goal of the extraction, fractionation, and purification process is the careful characterization and identification of a chemical entity within the crude extract that increases the expression or activity of the polypeptide. Methods of fractionation and purification of such heterogenous extracts are known in the art. If desired, agents shown to be useful as therapeutics for the treatment of human FSHD are chemically modified according to methods known in the art.

Inhibitory Nucleic Acids

Inhibitory nucleic acid molecules are those oligonucleotides that inhibit the expression or activity of a polypeptide that is overexpressed in FSHD (e.g., a polypeptide encoded by a gene listed in Table 2 or 4). Such oligonucleotides include single and double stranded nucleic acid molecules (e.g., DNA, RNA, and analogs thereof) that bind a nucleic acid molecule that encodes a polypeptide that is overexpressed in FSHD (e.g., antisense molecules, siRNA, shRNA) as well as nucleic acid molecules that bind directly to the polypeptide to modulate its biological activity (e.g., aptamers).

MOE Gapmers

In one embodiment, the invention provides methods for characterizing the effects of RNaseH1-activating antisense oligonucleotides (ASO's) ("MOE gapmers") on markers of the invention. The RNaseH1 ASO chemistry provides for a 20 nucleotide phosphorothioate backbone (5-10-5 gapmer). In particular, the oligonucleotide comprises five nucleotides at each end with the 2'-O-(2-methoxyethyl) (MOE) modification and ten central deoxyribonucleotides for activation of RNase H1. In one embodiment, cells derived from an FSHD affected and paired control cells are contacted with ASO's targeting DUX4. The effect of the downregulation of DUX4 on markers of the invention (e.g., markers listed in Table 2 or 4) is assayed. In another embodiment, a marker of the invention (e.g., a marker upregulated in FSHD) is targeted, and the effect of such targeting is assessed on the levels of other markers of the invention.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an sirNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a gene can be used to design small interfering RNAs (siRNAs). The 21 to 25 nucleotide siRNAs may be used, for example, as therapeutics to treat FSHD.

The inhibitory nucleic acid molecules of the present invention may be employed as double-stranded RNAs for RNA interference (RNAi)-mediated knock-down of expression. In one embodiment, expression of a gene listed in Table 2 or 4 is reduced in a skeletal muscle cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs (shRNAs) comprise an RNA sequence having a stem-loop structure. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, other molecule, or some combination thereof.

As used herein, the term "small hairpin RNA" includes a conventional stem-loop shRNA, which forms a precursor miRNA (pre-miRNA). While there may be some variation in range, a conventional stem-loop shRNA can comprise a stem ranging from 19 to 29 bp, and a loop ranging from 4 to 30 bp. "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one can design and express artificial miRNAs based on the features of existing miRNA genes.

shRNAs can be expressed from DNA vectors to provide sustained silencing and high yield delivery into almost any cell type. In some embodiments, the vector is a viral vector. Exemplary viral vectors include retroviral, including lentiviral, adenoviral, baculoviral and avian viral vectors, and including such vectors allowing for stable, single-copy genomic integrations. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

Catalytic RNA molecules or ribozymes that include an antisense sequence of the present invention can be used to inhibit expression of a nucleic acid molecule in vivo (e.g., a nucleic acid molecule listed in Table 2 or 4). The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

For expression within cells, DNA vectors, for example plasmid vectors comprising either an RNA polymerase II or RNA polymerase III promoter can be employed. Expression of endogenous miRNAs is controlled by RNA polymerase II (Pol II) promoters and in some cases, shRNAs are most efficiently driven by Pol II promoters, as compared to RNA polymerase III promoters (Dickins et al., 2005, Nat. Genet. 39: 914-921). In some embodiments, expression of the shRNA can be controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Modified Nucleic Acids

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275:4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301;

5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a gene listed in Table 2 or 4. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$—, and —O—N(CH$_3$)—CH$_2$—CH$_2$—. In some embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, SCH$_3$, OCN, Cl, Br, CN, CF$_3$, OCF$_3$, SOCH$_3$, SO$_2$CH$_3$, ONO$_2$, NO$_2$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—CH$_2$CH$_2$OCH$_3$, also known as 2'-O-(2-methoxyethyl) or 2'-MOE). Another desirable modification is 2'-dimethylaminooxyethoxy (i.e., O(CH$_2$)$_2$ON(CH$_3$)$_2$), also known as 2'-DMAOE. Other modifications include, 2'-aminopropoxy (2'-OCH$_2$CH$_2$NH$_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-5-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Delivery of Polynucleotides

Naked polynucleotides, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Polynucleotide Therapy for FSHD

Polynucleotide therapy is one therapeutic approach for preventing or ameliorating FSHD associated with the reduced expression of a nucleic acid molecule listed in Table 2 or 4. Such nucleic acid molecules can be delivered to cells that lack sufficient, normal protein expression or biological activity. The nucleic acid molecules must be delivered to those cells in a form in which they can be taken up by the cells and so that sufficient levels of protein can be produced to increase protein expression or function in a patient having FSHD.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a full length gene (e.g., a nucleic acid molecule listed in Table 2 or 4), or a portion thereof, can be cloned into a retroviral vector and expression can be driven from its endogenous promoter, from a retroviral long terminal repeat, or from a promoter specific for a target cell type of interest (e.g., a skeletal muscle cell). Promoters useful in the methods of the invention include, for example, myoD.

Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer the gene of interest (e.g., nucleic acid molecules listed in Table 2 or 4) systemically or to a skeletal muscle.

Non-viral approaches can also be employed for the introduction of therapeutic agent to a cell of an FSHD affected. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in gene therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types, such as cells of the central nervous system or their associated glial cells, can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant polypeptide encoded by a gene downregulated in FSHD. In one embodiment, the protein is either administered directly to a disease-affected tissue (for example, by injection into the muscle) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgement of the person administering or supervising the administration of the compositions. Generally, between 0.1 mg and 100 mg, is administered per day to an adult in any pharmaceutically acceptable formulation.

Pharmaceutical Therapeutics

The invention provides a simple means for identifying agents (including nucleic acid molecules, inhibitory nucleic acid molecules, peptides, small molecules, and mimetics) capable of acting as therapeutics for the treatment of FSHD. Accordingly, a chemical entity discovered to have medicinal value using the methods described herein is useful as a drug or as information for structural modification of existing agents, e.g., by rational drug design.

For therapeutic uses, the agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of FSHD therapeutic in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of FSHD. An agent is administered at a dosage that controls the clinical or physiological symptoms of FSHD as determined by clinical evaluation or by a diagnostic method of the invention that assays the expression of a nucleic acid molecule listed in Table 2 or 4, or the biological activity of a polypeptide encoded by such a nucleic acid molecule.

Formulation of Pharmaceutical Compositions

The administration of an agent for the treatment of FSHD may be by any suitable means that results in a concentration of the therapeutic that, combined with other components, is effective in ameliorating, reducing, or stabilizing FSHD. The agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target FSHD by using carriers or chemical derivatives to deliver the therapeutic agent to a particular cell type (e.g., skeletal muscle cell) whose function is perturbed in FSHD. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the FSHD therapeutic is formulated with appropriate excipients into a pharmaceutical composition that, upon administration, releases the FSHD therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active therapeutic (s), the composition may include suitable parenterally acceptable carriers and/or excipients. The active therapeutic (s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra. Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

The present invention provides methods of treating FSHD or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to FSHD or a symptom thereof. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which muscular dystrophy may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to FSHD, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1

Microarray Analysis Identifies Genes that are Differentially Regulated in FSHD

Open muscle biopsy was performed on both the biceps and deltoid muscles of 6 FSHD affected and 5 unaffected subjects that are first degree relatives of the FSHD affected subjects. Characteristics of the donors are provided in Table 1.

TABLE 1

Clinical characteristics of FSHD subjects and unaffected donors.

| Donor* | Familial Relations | Gender | Age at Enrollment (yrs) | EcoRI/BlnI Allele | Deltoid Strength** | Biceps Strength |
|---|---|---|---|---|---|---|
| 07A | proband | F | 18 | 29 kb | 4+/5 at 90° | full |
| 07U | mother of proband | F | 49 | 34 kb (4qB), 53 kb (4qA) | full | full |
| 09A | proband | F | 31 | 25 kb | 5/5 at 45° | 4+/5 |
| 09U | mother of 09A | F | 57 | 47 kb | full | full |
| 12A | proband | M | 49 | 18 kb | 4+/5 at 90° | 4+/5 |

TABLE 1-continued

Clinical characteristics of FSHD subjects and unaffected donors.

| Donor* | Familial Relations | Gender | Age at Enrollment (yrs) | EcoRI/Blnl Allele | Deltoid Strength** | Biceps Strength |
|---|---|---|---|---|---|---|
| 12U | sister of 12A | F | 45 | >112 kb | full | full |
| 15A | proband | M | 67 | 28 kb | 5/5 at 90° | 5/5 |
| 15B | brother of 15A | M | 69 | 28 kb | full | full |
| 15V | sister of 15A | F | 60 | 107 kb | full | full |
| 21B | proband | F | 59 | 34 kb | 5/5 | 4+/5 |
| 21U | sister of 21B | F | 48 | 150 kb | full | full |

*Donors are designated by cohort (family) number (07, 09, etc.) followed by A, B for the FSHD donors or U, V for the unaffected 1st degree relative(s) of the FSHD subject(s) in the cohort. Each cohort was composed of at least one affected individual with genetically and clinically verified FSHD, and at least one unaffected first degree relative with unshortened D4Z4 alleles and normal strength.
**Muscle strength is presented using a modified MRC scale where 5/5 is full strength for right/left sides.

Molecular diagnosis of FSHD was confirmed by the University of Iowa Diagnostic Laboratories and indicated that each donor with a clinical diagnosis of FSHD also had a contracted 4q D4Z4 region in combination with a 4qA telomeric allele (Table 1).

Primary Cell Culture.

Primary muscle cell strains were established from open muscle biopsies following collagenase IV and dispase dissociation as previously described (Stadler et al., 2011). Cells were cultured at 37° C. in 5% $CO_2$ on 0.1% gelatin-coated dishes and propagated by daily feeding with HMP growth medium consisting of Ham's F10 medium (Cellgro) supplemented with 20% characterized fetal bovine serum (Hyclone), 0.5% chicken embryo extract, 1.2 mM $CaCl_2$, and 1% antibiotics/antimycotics (Cellgro). Cultures were incubated until cells reached 50-70% confluence, at which time cells were harvested after dissociation with TrypLE Express (Gibco), counted, and expanded for fluorescence-activated cell sorting (FACS) or frozen storage.

The initial primary cultures were enriched for myogenic cells by using a FacsAria instrument (BD Biosciences) to select cells based on positive staining with APC-conjugated anti-human CD56 (BD Biosciences). For FACS, cells were trypsinized, counted, and collected by centrifugation, after which $\sim 1 \times 10^6$ cells were resuspended in 0.1 ml 10% fetal bovine serum (Hyclone) in PBS and incubated with the CD56 antibody according to manufacturer's instructions. As a control, cells were incubated with APC-conjugated mouse IgG1 K isotype antibody (BD Biosciences). Cells were incubated for 30-60 min on ice, collected by centrifugation, washed twice with 10% fetal bovine serum in PBS, and resuspended in 0.5-1.0 ml 10% fetal bovine serum in PBS and subjected to FACS to select CD56-positive cells.

The CD56-positive populations of myogenic cells that were obtained by FACS were seeded on dishes coated with 0.1% gelatin (Sigma) and incubated at 37° C. and 5% $CO_2$, with each cell strain grown independently. Cells were propagated by daily feeding with HMP growth medium consisting of Ham's F10 medium (Cellgro) supplemented with 20% characterized FBS (Hyclone), 1% chicken embryo extract, 120 mM $CaCl_2$, and 1% antibiotics/antimycotics (Cellgro). Cultures were incubated until cells reached 50-70% confluence, at which time cells were harvested after dissociation with TrypLE Express (Gibco), counted, and used for expansion or for frozen storage. For all experiments described here, cultures were examined at 20-35 population doublings after the initial isolation, which was at least 10-15 population doublings prior to loss of proliferative capacity.

FIG. 1 provides a table showing cell lines produced using these methods.

Primary Cell Cultures for RNA Isolation.

To initiate cultures, CD56-positive cells were seeded at ~4000 cells/$cm^2$ and cultured with daily feeding with LHCN growth medium consisting of 4:1 DMEM:Medium 199 supplemented with 15% characterized FBS (Hyclone), 0.02M HEPES (Sigma-Aldrich), 0.03 µg/ml $ZnSO_4$ (Sigma-Aldrich), 1.4 ug/ml Vitamin B12 (Sigma-Aldrich), 0.055 ug/ml dexamethasone (Sigma-Aldrich), 1% antibiotics/antimycotics (Cellgro), 2.5 ng/ml hepatocyte growth factor (Chemicon International) and 10 ng/ml basic fibroblast growth factor (Millipore). To induce differentiation, cells were propagated by daily feeding with LHCN growth medium until ~95% confluent, at which time cultures were switched to a low serum differentiation medium (DM) consisting of 4:1 DMEM:Medium 199 supplemented with 2% horse serum (Hyclone), 2 mM L-glutamine (Gibco), 1% antibiotics/antimycotics (Cellgro), 10 mM HEPES (Gibco), and 1 mM sodium pyruvate (Gibco). For RNA isolation for microarray analysis, cultures were harvested at two different stages of culture: (1) after two days of proliferation in growth medium, at which point cells were sub-confluent (GM); (2) after four days in differentiation medium (DM). Cells were harvested by rinsing culture dishes 2× with PBS and removing the cells with cell lifters (Costar), after which the cells were collected by centrifugation, snap frozen in liquid nitrogen, and stored at −80° C.

RNA Isolation and Microarray Analysis.

Total RNA was isolated from frozen cell pellets using 1 ml TRIzol reagent (Invitrogen). RNA concentration was quantified with UV absorption at 260 nm using NanoDrop ND-1000 Spectrophotometer (Thermo Fisher Scientific) and the RNA integrity was assessed using the RNA 6000 Nano chip on the Agilent 2100 Bioanalyzer (Agilent Technologies). Gene expression profiling was carried out using the Affymetrix GeneChip Human Gene 1.0 ST arrays. The current format of these arrays interrogates 28,869 annotated genes in the human genome with approximately twenty six 25-mer oligonucleotide probes spread across the full length of the transcript. Microarray data was collected at Expression Analysis, Inc. (Durham, N.C.). Biotin-labeled target for the microarray experiment was prepared using 100 ng of total RNA and cDNA was synthesized using the GeneChip WT (Whole Transcript) Sense Target Labeling and Control Reagents kit as described by the manufacturer (Affymetrix). The sense cDNA was then fragmented by UDG (uracil DNA glycosylase) and APE 1 (apurinic/apyrimidic endonuclease 1) and biotin-labeled with TdT (terminal deoxynucleotidyl transferase) using the GeneChip WT Terminal labeling kit (Affymetrix). Hybridization was performed using 5 micrograms of biotinylated target, which was incubated with the Gene- Chip Human Gene 1.0 ST array (Affymetrix) at 45° C. for 16-20 hours. Following hybridization, non-specifically bound material was removed by washing and detection of specifically bound target was performed using the GeneChip Hybridization, Wash and Stain kit, and the GeneChip Fluidics Station 450 (Affymetrix). The arrays were scanned using the GeneChip Scanner 3000 7G (Affymetrix) and raw data was extracted from the scanned images and analyzed with the Affymetrix GeneChip Command Console Software (Affymetrix).

Microarray Data Analysis.

The raw array data was preprocessed and normalized using the Robust Multichip Average (RMA) method. This procedure includes background correction and quantile normalization of the arrays at the probe level, followed by robust summarization of expression at the transcript level. Differential expression between classes was calculated using linear models with the limma package from the Bioconductor project (Smyth, G. K. (2004). Linear models and empirical Bayes methods for assessing differential expression in microarray experiments. Statistical Applications in Genetics and Molecular Biology 3, No. 1, Article 3). The linear model used was "~0+Class:Muscle:Medium+Cohort", where Class, Muscle, and Medium are each two-level factors with levels FSHD & Control; Biceps & Deltoid; and GM & DM, respectively; and the factor Cohort has one level for each cohort. The interaction terms (denoted ":") for the three two-level factors model changes between FSHD and Control expression levels that may vary for each of the four combinations of muscle type and medium, and the additive Cohort factor models different baseline expression levels for samples from different cohorts. To control for multiple hypothesis testing false discovery rates (FDRs) were computed based on the p-values from empirical Bayes moderated t-statistics for differential expression. The reported results are based on only those probesets annotated with Entrez gene IDs, and in cases of multiple probesets with the same Entrez ID on only the probeset with the largest interquartile range; after this filtering probesets corresponding to 19,983 genes were left. FSHD typically affects biceps more severely than deltoid, and differences between FSHD and control cell-cultures were stronger in DM than in GM.

Table 2 lists 142 genes for which the expression difference between FSHD and control biceps in DM had p-value at most 0.001, which corresponded to an FDR of 0.15. The columns labeled AvsU.DM.B.pval and AvsU.DM.B. gives the p-value and FDR, respectively, and the column labeled AvsU.DM.B.lfc gives the log 2(fold-change) between FSHD and control expression levels, with positive scores indicating higher expression in FSHD samples relative to controls, and negative scores indicating lower expression in FSHD samples relative to controls (Table 2).

TABLE 2

| Probeset | SYMBOL | UNIGENE | ENTREZID | REFSEQ | GENENAME | AvsU.DM.B.lfc | AvsU.DM.B.pval | AvsU.DM.B.fdr |
|---|---|---|---|---|---|---|---|---|
| 7933733 | FAM13C | Hs.499704 | 220965 | NM_001001971.2 | family with sequence similarity 13, member C | −0.85 | 5.30E−07 | 0.011 |
| 8153065 | MIR30B | NA | 407030 | NR_029666.1 | microRNA 30b | −0.9 | 1.70E−06 | 0.017 |
| 8079753 | DAG1 | Hs.76111 | 1605 | NM_001165928.3 | dystroglycan 1 (dystrophin-associated glycoprotein 1) | −0.59 | 1.20E−05 | 0.071 |
| 7910923 | FMN2 | Hs.24889 | 56776 | NM_020066.4 | formin 2 | 0.77 | 1.40E−05 | 0.071 |
| 7927876 | TET1 | Hs.567594 | 80312 | NM_030625.2 | tet oncogene 1 | −0.65 | 1.80E−05 | 0.072 |
| 8075673 | RBFOX2 | Hs.282998 | 23543 | NM_001031695.2 | RNA binding protein, fox-1 homolog (C. elegans) 2 | −0.43 | 4.10E−05 | 0.1 |
| 7980891 | TC2N | Hs.510262 | 123036 | NM_001128595.1 | tandem C2 domains, nuclear | 0.72 | 5.20E−05 | 0.1 |
| 8126770 | CYP39A1 | Hs.387367 | 51302 | NM_016593.3 | cytochrome P450, family 39, subfamily A, polypeptide 1 | −0.51 | 6.60E−05 | 0.1 |
| 8054041 | TRIM43 | Hs.232026 | 129868 | NM_138800.1 | tripartite motif containing 43 | 2.59 | 7.30E−05 | 0.1 |
| 8034099 | MIR199A1 | NA | 406976 | NR_029586.1 | microRNA 199a-1 | 0.88 | 7.50E−05 | 0.1 |
| 8057578 | CALCRL | Hs.470882 | 10203 | NM_005795.5 | calcitonin receptor-like | −1.17 | 8.40E−05 | 0.1 |
| 7898537 | PAX7 | Hs.113253 | 5081 | NM_001135254.1 | paired box 7 | −0.75 | 8.40E−05 | 0.1 |
| 8084100 | USP13 | Hs.175322 | 8975 | NM_003940.2 | ubiquitin specific peptidase 13 (isopeptidase T-3) | −0.75 | 8.40E−05 | 0.1 |
| 7994463 | ATP2A1 | Hs.657344 | 487 | NM_004320.4 | ATPase, Ca++ transporting, cardiac muscle, fast twitch 1 | −1.82 | 8.70E−05 | 0.1 |
| 7958174 | TXNRD1 | Hs.728817 | 7296 | NM_001093771.2 | thioredoxin reductase 1 | 0.49 | 8.80E−05 | 0.1 |
| 7982000 | SNORD116-26 | NA | 100033438 | NR_003340.2 | small nucleolar RNA, C/D box 116-26 | −0.78 | 9.10E−05 | 0.1 |
| 7973580 | FITM1 | Hs.128060 | 161247 | NM_203402.2 | fat storage-inducing transmembrane protein 1 | −0.72 | 9.90E−05 | 0.1 |
| 7928661 | MBL1P | Hs.102310 | 8512 | NR_002724.2 | mannose-binding lectin (protein A) 1, pseudogene | −0.67 | 1.00E−04 | 0.1 |
| 8053984 | ANKRD23 | Hs.643430 | 200539 | NM_144994.7 | ankyrin repeat domain 23 | −0.45 | 0.00011 | 0.1 |
| 7941761 | RHOD | Hs.15114 | 29984 | NM_014578.3 | ras homolog gene family, member D | 0.45 | 0.00011 | 0.1 |
| 8072015 | ADRBK2 | Hs.657494 | 157 | NM_005160.3 | adrenergic, beta, receptor kinase 2 | −0.78 | 0.00012 | 0.1 |
| 8027674 | ZNF302 | Hs.436350 | 55900 | NM_001012320.1 | zinc finger protein 302 | −0.36 | 0.00012 | 0.1 |
| 8120961 | MRAP2 | Hs.370055 | 112609 | NM_138409.2 | melanocortin 2 receptor accessory protein 2 | −0.93 | 0.00013 | 0.1 |

TABLE 2-continued

| Probeset | SYMBOL | UNIGENE | ENTREZID | REFSEQ | GENENAME | AvsU.DM.B.lfc | AvsU.DM.B.pval | AvsU.DM.B.fdr |
|---|---|---|---|---|---|---|---|---|
| 7960865 | SLC2A3 | Hs.419240 | 6515 | NM_006931.2 | solute carrier family 2 (facilitated glucose transporter), member 3 | 0.64 | 0.00013 | 0.1 |
| 7947052 | IGSF22 | Hs.434152 | 283284 | NM_173588.3 | immunoglobulin superfamily, member 22 | −0.58 | 0.00014 | 0.1 |
| 8093665 | GRK4 | Hs.32959 | 2868 | NM_001004056.1 | G protein-coupled receptor kinase 4 | −0.46 | 0.00014 | 0.1 |
| 8162132 | C9orf153 | Hs.632073 | 389766 | NM_001010907.1 | chromosome 9 open reading frame 153 | −0.52 | 0.00014 | 0.1 |
| 8008664 | AKAP1 | Hs.463506 | 8165 | NM_003488.3 | A kinase (PRKA) anchor protein 1 | −0.64 | 0.00015 | 0.11 |
| 8101086 | NAAA | Hs.437365 | 27163 | NM_001042402.1 | N-acylethanolamine acid amidase | 0.52 | 0.00016 | 0.11 |
| 7915261 | TRIT1 | Hs.356554 | 54802 | NM_017646.4 | tRNA isopentenyltransferase 1 | −0.48 | 0.00016 | 0.11 |
| 8058570 | C2orf67 | Hs.282260 | 151050 | NM_152519.2 | chromosome 2 open reading frame 67 | −0.56 | 0.00018 | 0.11 |
| 7912595 | PRAMEF13 | Hs.531192 | 400736 | NM_001024661.1 | PRAME family member 13 | 1.52 | 0.00019 | 0.11 |
| 7978932 | SOS2 | Hs.291533 | 6655 | NM_006939.2 | son of sevenless homolog 2 (Drosophila) | −0.27 | 0.00019 | 0.11 |
| 8023121 | ST8SIA5 | Hs.465025 | 29906 | NM_013305.4 | ST8 alpha-N-acetyl-neuraminide alpha-2,8-sialyltransferase 5 | −0.61 | 0.00021 | 0.12 |
| 7934945 | PANK1 | Hs.376351 | 53354 | NM_138316.3 | pantothenate kinase 1 | −0.66 | 0.00021 | 0.12 |
| 7979483 | C14orf39 | Hs.335754 | 317761 | NM_174978.2 | chromosome 14 open reading frame 39 | −0.79 | 0.00022 | 0.12 |
| 7923978 | CD34 | Hs.374990 | 947 | NM_001025109.1 | CD34 molecule | 0.79 | 0.00023 | 0.12 |
| 7920552 | KCNN3 | Hs.490765 | 3782 | NM_001204087.1 | potassium intermediate/small conductance calcium-activated channel, subfamily N, member 3 | −0.88 | 0.00024 | 0.12 |
| 8082003 | EAF2 | Hs.477325 | 55840 | NM_018456.4 | ELL associated factor 2 | −0.69 | 0.00024 | 0.12 |
| 8024518 | ZNF555 | Hs.47712 | 148254 | NM_001172775.1 | zinc finger protein 555 | −0.82 | 0.00026 | 0.12 |
| 8151074 | PDE7A | Hs.527119 | 5150 | NM_002603.3 | phosphodiesterase 7A | −0.61 | 0.00026 | 0.12 |
| 8130071 | C15orf29 | Hs.633566 | 79768 | NM_024713.2 | chromosome 15 open reading frame 29 | −0.76 | 0.00027 | 0.12 |
| 8123584 | MYLK4 | Hs.127830 | 340156 | NM_001012418.3 | myosin light chain kinase family, member 4 | −1.18 | 0.00028 | 0.12 |
| 7906764 | HSPA6 | Hs.654614 | 3310 | NM_002155.3 | heat shock 70 kDa protein 6 (HSP70B') | 0.49 | 0.00029 | 0.12 |
| 7897987 | PRAMEF2 | Hs.104991 | 65122 | NM_023014.1 | PRAME family member 2 | 1.59 | 0.00029 | 0.12 |
| 7926679 | KIAA1217 | Hs.445885 | 56243 | NM_001098500.1 | KIAA1217 | −0.58 | 0.00031 | 0.12 |
| 8163733 | CDK5RAP2 | Hs.269560 | 55755 | NM_001011649.2 | CDK5 regulatory subunit associated protein 2 | −0.4 | 0.00032 | 0.12 |
| 8050443 | SMC6 | Hs.526728 | 79677 | NM_001142286.1 | structural maintenance of chromosomes 6 | −0.5 | 0.00033 | 0.12 |
| 7947110 | E2F8 | Hs.523526 | 79733 | NM_024680.3 | E2F transcription factor 8 | −1.38 | 0.00033 | 0.12 |
| 8073943 | ZBED4 | Hs.475208 | 9889 | NM_014838.2 | zinc finger, BED-type containing 4 | −0.36 | 0.00034 | 0.12 |
| 7958884 | OAS1 | Hs.524760 | 4938 | NM_001032409.1 | 2',5'-oligoadenylate synthetase 1, 40/46 kDa | 0.63 | 0.00035 | 0.12 |
| 8133477 | GTF2IRD1 | Hs.647056 | 9569 | NM_001199207.1 | GTF2I repeat domain containing 1 | −0.51 | 0.00035 | 0.12 |
| 7944955 | PKNOX2 | Hs.278564 | 63876 | NM_022062.2 | PBX/knotted 1 homeobox 2 | −0.62 | 0.00036 | 0.12 |
| 8020068 | ANKRD12 | Hs.464585 | 23253 | NM_001083625.2 | ankyrin repeat domain 12 | −0.43 | 0.00037 | 0.12 |
| 7983704 | GLDN | Hs.526441 | 342035 | NM_181789.2 | gliomedin | −0.45 | 0.00037 | 0.12 |
| 8131803 | IL6 | Hs.654458 | 3569 | NM_000600.3 | interleukin 6 (interferon, beta 2) | 1.12 | 0.00037 | 0.12 |
| 7909730 | KCNK2 | Hs.497745 | 3776 | NM_001017424.2 | potassium channel, subfamily K, member 2 | 1.18 | 0.00037 | 0.12 |
| 7908397 | RGS13 | Hs.497220 | 6003 | NM_002927.4 | regulator of G-protein signaling 13 | −1.02 | 0.00037 | 0.12 |
| 8072170 | KREMEN1 | Hs.229335 | 83999 | NM_001039570.2 | kringle containing transmembrane protein 1 | −0.53 | 0.00037 | 0.12 |
| 8002020 | TPPP3 | Hs.534458 | 51673 | NM_015964.2 | tubulin polymerization- | −0.61 | 0.00039 | 0.12 |

TABLE 2-continued

| Probeset | SYMBOL | UNIGENE | ENTREZID | REFSEQ | GENENAME | AvsU.DM.B.lfc | AvsU.DM.B.pval | AvsU.DM.B.fdr |
|---|---|---|---|---|---|---|---|---|
| | | | | | promoting protein family member 3 | | | |
| 7897978 | PRAMEF1 | Hs.454859 | 65121 | NM_023013.2 | PRAME family member 1 | 1.33 | 0.00039 | 0.12 |
| 7909545 | TRAF5 | Hs.523930 | 7188 | NM_001033910.2 | TNF receptor-associated factor 5 | −0.64 | 0.00039 | 0.12 |
| 8094441 | SLC34A2 | Hs.479372 | 10568 | NM_001177998.1 | solute carrier family 34 (sodium phosphate), member 2 | 2.23 | 4.00E−04 | 0.12 |
| 8137670 | PDGFA | Hs.535898 | 5154 | NM_002607.5 | platelet-derived growth factor alpha polypeptide | −0.58 | 4.00E−04 | 0.12 |
| 8086482 | ZNF445 | Hs.250481 | 353274 | NM_181489.5 | zinc finger protein 445 | −0.31 | 0.00041 | 0.12 |
| 7964646 | PPM1H | Hs.435479 | 57460 | NM_020700.1 | protein phosphatase, Mg2+/Mn2+ dependent, 1H | −0.42 | 0.00041 | 0.12 |
| 8027312 | ZNF429 | Hs.572567 | 353088 | NM_001001415.2 | zinc finger protein 429 | −0.58 | 0.00042 | 0.12 |
| 7969815 | CLYBL | Hs.655642 | 171425 | NM_206808.2 | citrate lyase beta like | −0.57 | 0.00043 | 0.12 |
| 8099302 | MIR95 | NA | 407052 | NR_029511.1 | microRNA 95 | −1 | 0.00045 | 0.12 |
| 7971653 | DLEU2 | Hs.547964 | 8847 | NR_002612.1 | deleted in lymphocytic leukemia 2 (non-protein coding) | −0.53 | 0.00045 | 0.12 |
| 8069991 | TCP10L | Hs.728804 | 140290 | NM_144659.5 | t-complex 10 (mouse)-like | −0.4 | 0.00047 | 0.12 |
| 7970111 | ARHGEF7 | Hs.508738 | 8874 | NM_001113511.1 | Rho guanine nucleotide exchange factor (GEF) 7 | −0.4 | 0.00047 | 0.12 |
| 7995440 | FLJ44674 | Hs.514338 | 400535 | XR_041153.1 | FLJ44674 protein | 0.35 | 5.00E−04 | 0.12 |
| 7898211 | DDI2 | Hs.718857 | 84301 | NM_032341.4 | DNA-damage inducible 1 homolog 2 (S. cerevisiae) | −0.48 | 5.00E−04 | 0.12 |
| 8163109 | C9orf4 | Hs.347537 | 23732 | NM_014334.2 | chromosome 9 open reading frame 4 | 0.4 | 0.00052 | 0.12 |
| 7918552 | C1orf183 | Hs.193406 | 55924 | NM_019099.4 | chromosome 1 open reading frame 183 | −0.43 | 0.00052 | 0.12 |
| 7960850 | SLC2A14 | Hs.655169 | 144195 | NM_153449.2 | solute carrier family 2 (facilitated glucose transporter), member 14 | 0.49 | 0.00053 | 0.12 |
| 8050658 | ATAD2B | Hs.467862 | 54454 | NM_017552.2 | ATPase family, AAA domain containing 2B | −0.33 | 0.00053 | 0.12 |
| 8124502 | ZNF184 | Hs.158174 | 7738 | NM_007149.2 | zinc finger protein 184 | −0.35 | 0.00053 | 0.12 |
| 8060813 | MCM8 | Hs.597484 | 84515 | NM_032485.4 | minichromosome maintenance complex component 8 | −0.39 | 0.00053 | 0.12 |
| 8097086 | MYOZ2 | Hs.381047 | 51778 | NM_016599.4 | myozenin 2 | −1.2 | 0.00054 | 0.12 |
| 8044008 | IL1RL2 | Hs.659863 | 8808 | NM_003854.2 | interleukin 1 receptor-like 2 | 0.38 | 0.00054 | 0.12 |
| 8054664 | ZC3H8 | Hs.418416 | 84524 | NM_032494.2 | zinc finger CCCH-type containing 8 | −0.4 | 0.00055 | 0.12 |
| 8097256 | FGF2 | Hs.284244 | 2247 | NM_002006.4 | fibroblast growth factor 2 (basic) | 0.88 | 0.00056 | 0.12 |
| 8100312 | LRRC66 | Hs.661450 | 339977 | NM_001024611.1 | leucine rich repeat containing 66 | −0.77 | 0.00056 | 0.12 |
| 8102352 | PITX2 | Hs.643588 | 5308 | NM_000325.5 | paired-like homeodomain 2 | −0.53 | 0.00056 | 0.12 |
| 8015590 | STAT5B | Hs.595276 | 6777 | NM_012448.3 | signal transducer and activator of transcription 5B | −0.54 | 0.00056 | 0.12 |
| 8069348 | PCNT | Hs.474069 | 5116 | NM_006031.5 | pericentrin | −0.34 | 0.00057 | 0.12 |
| 8136235 | CPA1 | Hs.2879 | 1357 | NM_001868.2 | carboxypeptidase A1 (pancreatic) | −0.4 | 0.00058 | 0.12 |
| 7968883 | C13orf31 | Hs.210586 | 144811 | NM_001128303.1 | chromosome 13 open reading frame 31 | 0.94 | 0.00058 | 0.12 |
| 7950955 | TRIM49 | Hs.534218 | 57093 | NM_020358.2 | tripartite motif containing 49 | 1.68 | 0.00058 | 0.12 |
| 7957126 | KCNMB4 | Hs.525529 | 27345 | NM_014505.5 | potassium large conductance calcium-activated channel, subfamily M, beta member 4 | −0.82 | 0.00059 | 0.12 |
| 8102862 | MAML3 | Hs.586165 | 55534 | NM_018717.4 | mastermind-like 3 (Drosophila) | −0.54 | 0.00059 | 0.12 |
| 7951781 | C11orf71 | Hs.715083 | 54494 | NM_019021.3 | chromosome 11 open reading frame 71 | −0.37 | 6.00E−04 | 0.12 |
| 7909768 | SPATA17 | Hs.171130 | 128153 | NM_138796.2 | spermatogenesis associated 17 | −0.49 | 0.00061 | 0.12 |

TABLE 2-continued

| Probeset | SYMBOL | UNIGENE | ENTREZID | REFSEQ | GENENAME | AvsU.DM.B.lfc | AvsU.DM.B.pval | AvsU.DM.B.fdr |
|---|---|---|---|---|---|---|---|---|
| 8094778 | UCHL1 | Hs.518731 | 7345 | NM_004181.4 | ubiquitin carboxyl-terminal esterase L1 (ubiquitin thiolesterase) | 0.77 | 0.00061 | 0.12 |
| 8164580 | PTGES | Hs.146688 | 9536 | NM_004878.4 | prostaglandin E synthase | 0.94 | 0.00061 | 0.12 |
| 8104163 | LRRC14B | Hs.683662 | 389257 | NM_001080478.1 | leucine rich repeat containing 14B | −0.57 | 0.00062 | 0.12 |
| 8036406 | ZNF571 | Hs.590944 | 51276 | NM_016536.3 | zinc finger protein 571 | −0.41 | 0.00062 | 0.12 |
| 8128087 | GABRR1 | Hs.99927 | 2569 | NM_002042.4 | gamma-aminobutyric acid (GABA) receptor, rho 1 | −0.63 | 0.00063 | 0.12 |
| 8028219 | ZNF420 | Hs.444992 | 147923 | NM_144689.3 | zinc finger protein 420 | −0.39 | 0.00064 | 0.13 |
| 8057771 | STAT4 | Hs.80642 | 6775 | NM_003151.3 | signal transducer and activator of transcription 4 | 0.67 | 0.00067 | 0.13 |
| 8058350 | ICA1L | Hs.516629 | 130026 | NM_138468.4 | islet cell autoantigen 1.69 kDa-like | −0.46 | 0.00068 | 0.13 |
| 8018922 | CYTH1 | Hs.191215 | 9267 | NM_004762.2 | cytohesin 1 | −0.47 | 0.00068 | 0.13 |
| 7968637 | CCNA1 | Hs.417050 | 8900 | NM_001111045.1 | cyclin A1 | 2.12 | 0.00073 | 0.14 |
| 7974771 | C14orf135 | Hs.509499 | 64430 | NM_022495.5 | chromosome 14 open reading frame 135 | −0.37 | 0.00076 | 0.14 |
| 7907790 | CEP350 | Hs.413045 | 9857 | NM_014810.4 | centrosomal protein 350 kDa | −0.44 | 0.00076 | 0.14 |
| 8030823 | IGLON5 | Hs.546636 | 402665 | NM_001101372.1 | IgLON family member 5 | 0.45 | 0.00077 | 0.14 |
| 7917996 | LRRC39 | Hs.44277 | 127495 | NM_144620.3 | leucine rich repeat containing 39 | −1.23 | 0.00078 | 0.14 |
| 7905986 | FDPS | Hs.335918 | 2224 | NM_001135821.1 | farnesyl diphosphate synthase | 0.59 | 0.00079 | 0.14 |
| 8097867 | KIAA0922 | Hs.205572 | 23240 | NM_001131007.1 | KIAA0922 | −0.4 | 0.00079 | 0.14 |
| 8120300 | C6orf142 | Hs.449276 | 90523 | NM_138569.2 | chromosome 6 open reading frame 142 | −1.71 | 0.00079 | 0.14 |
| 8068220 | C21orf49 | Hs.54725 | 54067 | NR_024622.1 | chromosome 21 open reading frame 49 | −0.43 | 8.00E−04 | 0.14 |
| 8037298 | CD177 | Hs.232165 | 57126 | NM_020406.2 | CD177 molecule | 0.83 | 8.00E−04 | 0.14 |
| 8148501 | PTP4A3 | Hs.43666 | 11156 | NM_007079.2 | protein tyrosine phosphatase type IVA, member 3 | −0.93 | 0.00081 | 0.14 |
| 7954012 | LOH12CR1 | Hs.720779 | 118426 | NM_058169.3 | loss of heterozygosity, 12, chromosomal region 1 | −0.43 | 0.00084 | 0.14 |
| 8108708 | PCDHB7 | Hs.203830 | 56129 | NM_018940.2 | protocadherin beta 7 | −0.37 | 0.00085 | 0.14 |
| 8116595 | WRNIP1 | Hs.236828 | 56897 | NM_020135.2 | Werner helicase interacting protein 1 | −0.31 | 0.00085 | 0.14 |
| 7934434 | MYOZ1 | Hs.238756 | 58529 | NM_021245.3 | myozenin 1 | −1.55 | 0.00085 | 0.14 |
| 8024909 | KDM4B | Hs.654816 | 23030 | NM_015015.2 | lysine (K)-specific demethylase 4B | −0.26 | 0.00086 | 0.14 |
| 8144812 | PCM1 | Hs.491148 | 5108 | NM_006197.3 | pericentriolar material 1 | −0.33 | 0.00086 | 0.14 |
| 7933092 | ZNF248 | Hs.528423 | 57209 | NM_021045.2 | zinc finger protein 248 | −0.5 | 0.00086 | 0.14 |
| 7928705 | TSPAN14 | Hs.310453 | 81619 | NM_001128309.1 | tetraspanin 14 | −0.62 | 0.00086 | 0.14 |
| 8151457 | HEY1 | Hs.234434 | 23462 | NM_001040708.1 | hairy/enhancer-of-split related with YRPW motif 1 | −0.58 | 0.00087 | 0.14 |
| 7934442 | SYNPO2L | Hs.645273 | 79933 | NM_001114133.1 | synaptopodin 2-like | −0.78 | 0.00088 | 0.14 |
| 8033241 | CD70 | Hs.501497 | 970 | NM_001252.3 | CD70 molecule | 0.32 | 0.00088 | 0.14 |
| 7921955 | RXRG | Hs.26550 | 6258 | NM_006917.4 | retinoid X receptor, gamma | −0.58 | 0.00089 | 0.14 |
| 8167603 | CLCN5 | Hs.166486 | 1184 | NM_000084.3 | chloride channel 5 | −0.57 | 9.00E−04 | 0.14 |
| 8089647 | KIAA2018 | Hs.632570 | 205717 | NM_001009899.2 | KIAA2018 | −0.4 | 0.00091 | 0.14 |
| 8139160 | FAM183B | Hs.144075 | 340286 | NR_028347.1 | acyloxyacyl hydrolase (neutrophil) | 0.35 | 0.00091 | 0.14 |
| 7957379 | MYF5 | Hs.178023 | 4617 | NM_005593.2 | myogenic factor 5 | −0.91 | 0.00094 | 0.14 |
| 8144082 | C7orf13 | Hs.647014 | 129790 | NR_026865.1 | chromosome 7 open reading frame 13 | −0.39 | 0.00095 | 0.14 |
| 7986004 | ZNF774 | Hs.55307 | 342132 | NM_001004309.2 | zinc finger protein 774 | −0.28 | 0.00095 | 0.14 |
| 8045198 | CFC1B | Hs.503733 | 653275 | NM_001079530.1 | cripto, FRL-1, cryptic family 1B | 0.26 | 0.00096 | 0.14 |
| 8125289 | TNXA | Hs.708061 | 7146 | NR_001284.2 | tenascin XA pseudogene | 1.87 | 0.00097 | 0.14 |
| 7915277 | MYCL1 | Hs.437922 | 4610 | NM_001033081.2 | v-myc myelocytomatosis viral oncogene homolog 1, lung carcinoma derived (avian) | −0.77 | 0.00098 | 0.14 |

TABLE 2-continued

| Probeset | SYMBOL | UNIGENE | ENTREZID | REFSEQ | GENENAME | AvsU.DM.B.lfc | AvsU.DM.B.pval | AvsU.DM.B.fdr |
|---|---|---|---|---|---|---|---|---|
| 8002303 | NQO1 | Hs.406515 | 1728 | NM_000903.2 | NAD(P)H dehydrogenase, quinone 1 | 0.67 | 0.001 | 0.15 |
| 8033362 | INSR | Hs.465744 | 3643 | NM_000208.2 | insulin receptor | −0.59 | 0.001 | 0.15 |
| 8025672 | SLC44A2 | Hs.534560 | 57153 | NM_001145056.1 | solute carrier family 44, member 2 | −0.35 | 0.001 | 0.15 |
| 7965510 | TMCC3 | Hs.370410 | 57458 | NM_020698.2 | transmembrane and coiled-coil domain family 3 | −0.42 | 0.001 | 0.15 |
| 8118644 | RPS18 | Hs.627414 | 6222 | NM_022551.2 | ribosomal protein S18 | 0.34 | 0.001 | 0.15 |
| 7940824 | NAA40 | Hs.523753 | 79829 | NM_024771.2 | N(alpha)-acetyltransferase 40, NatD catalytic subunit, homolog (S. cerevisiae) | −0.33 | 0.001 | 0.15 |

Example 2

A Humanized Mouse Model of FSHD

Both FSHD- and control-derived myoblasts from multiple cohorts (described in Homma et al., European Journal of Human Genetics (2012) 20, 404-410) engrafted and formed human muscle fibers after 30 days in vivo. All mouse experiments were performed using BBRI IACUC-approved protocols. Nonobese diabetic Rag1 and IL2rγ null (NOD-Rag1 null IL2r null or RAG, Jax stock number 007799) mice were used as recipients for human cell transplantations. Adult muscle, composed of multinucleated terminally differentiated myofibers, has a very low rate of cellular turnover under normal conditions. However, it has a remarkable capacity to regenerate in response to injury due to the presence of quiescent satellite cells. A regenerating muscle, which is in the process of incorporating newly differentiating cells, provides a favourable environment to receive a cell graft. Recipient tibialis anterior (TA) muscles were injected with 10 µM cardiotoxin to induce a muscle degeneration/regeneration cycle. $1\times10^6$ FSHD myoblasts (from five different family cohorts), maintained in culture between 15 and 20 population doublings, were injected into surgically-exposed TA muscles 6 hours after cardiotoxin injection; following surgery, mice were monitored for recovery from anaesthesia and provided analgesics as required. Mice were sacrificed 4 weeks after transplantation and injected TA muscles, as well as non-injected gastrocnemius muscles were dissected and frozen in nitrogen-cooled isopentane. Entire muscle samples were cut into 10 µm transverse cryostat sections and analyzed by immunofluorescence.

Visualization of engrafted fibers was performed via immunofluorescence using antibodies against the human specific sarcolemmal protein spectrin and the human specific nuclear protein lamin A/C. As shown in FIG. 1, immunofluorescence using human specific antibodies demonstrated high engraftment efficiency. To date, 36 xenografted mice have been generated and investigated. Histological analyses have confirmed that injected human FSHD myoblasts participate in the regeneration of murine muscle to form "humanized" fibers within the host TA. Quantifications have revealed that engraftment rates of greater than 100,000 human nuclei can be achieved in host muscle. These engraftments are of a sufficient magnitude to conduct morphological and molecular phenotype analyses of xenografted muscles. It is hypothesized that prior irradiation of host mice enriches engraftment of human myoblasts.

Example 3

DUX4-fl Expressing FSHD Cells Engraft

Five cell strains (described in Homma et al., European Journal of Human Genetics (2012) 20, 404-410) were used for engraftment studies. Recent breakthroughs in the field suggest that DUX4, a gene identified inside D4Z4 repeats, is inappropriately expressed in the muscles of patients with FSHD. The disease could arise though a toxic gain of function. The precise molecular and cellular pathological mechanism involving DUX4 remains to be uncovered. Recent studies described the detection of two DUX4 transcripts, a long form (or full-length, fl) and a short form, and while the role of the short form is still unclear, the long form was specifically detected in FSHD samples, suggesting a central role in the pathogenic mechanism.

Based on engraftability and expression of DUX4-fl, cell strain selection for engraftment was refined to consist of three strains derived from the biceps of patients affected by FSHD, and three cell strains from corresponding unaffected first degree relatives. DUX4-fl transcript and protein were detected in cultured, differentiated myotubes for each of the three FSHD cell strains, and was absent in each control. Two control cell strains possessed at least one permissive allele for the disease (4qA), but repressed DUX4 transcription. The third control strain did not contain the permissive allele (i.e. was genotyped as 4qB/4qB), and was therefore an ideal negative control for these studies.

Current theory predicts that DUX4 is actively transcribed in an average of 1 out of a 1,000 FSHD-derived nuclei at a given time. Recent engraftment trials have established that over 100,000 human myonuclei can be integrated with murine muscle. Adapting current theory to the invention's xenograft model, DUX4 might be expressed in greater than 100 nuclei in sizeable xenografts. This represents an amount of DUX4 mRNA detectable using 55 cycles of nested PCR; therefore, DUX4 expression at these levels should be detectable in xenografts from FSHD-derived myoblasts. Currently the expression of DUX4 at the mRNA and/or protein level is being assessed in FSHD- and control-transplanted TAs.

Example 4

Xenograft Integration with the Murine Skeletal Muscle Environment

Innervation of Human Fibers

Injecting cultured human myoblasts into murine skeletal muscle imposes a drastic environmental change. The ability of human myoblasts to assimilate successfully with host muscle is one important feature of a disease model. Immunohistological assays have confirmed that injected myoblasts successfully adapted to the murine microenvironment and integrated with the host muscle. Innervation of engrafted fibers by the nervous system of the host is important to prevent atrophy. Immunohistology studies using antibodies against neurofilament and Synaptic Vesicle protein 2 (SV2) were used to visualize afferent murine neurons in transverse sections. SV2 immunofluorescence at the pre-synaptic cleft was coupled with bungarotoxin-rhodamine staining at corresponding post-synaptic acetylcholine receptors to demonstrate an active neuromuscular junction (FIG. 2). Neuromuscular junction dispersion was observed throughout the muscle in specific patterns, directly innervating fibers in their vicinity without appearing to discriminate between mouse and human. Neuromuscular junctions on human and mouse fibers had no noticeable morphological differences. It is likely that resulting human fibers are successfully integrating with the murine musculature and nervous system.

Example 5

Xenograft Integration with Murine Skeletal Muscle Environment: Satellite Cell Pool Replenishment The ability of injected cells to contribute to long-term muscle regeneration is dependent upon their inclusion into the satellite cell pool of host muscle. Satellite cells are muscle progenitor cells located beneath the basal lamina of myofibers. They are activated in response to damage, causing them to proliferate and fuse to form new myofibers during the repair process. Satellite cells can be identified by the expression of the transcription factor PAX7 and their anatomical location beneath the basal lamina. Using antibodies against these distinct features coupled with human LaminA/C, human nuclei that express PAX7 were identified. This indicates that these cells have assumed a satellite cell identity (FIG. 3).

Example 6

Development of a Tracking Strategy to Follow the Transplant Over Time

In vivo imaging provides a powerful tool to track the growth and survival of implanted muscle cells over time. Lentiviral particles are highly efficient at infection and stable integration of a gene of interest into a cell system. Lentiviral particles expressing a firefly luciferase (Luc) reporter gene provide a simple, long-term cell tracking system. Live small animal in vivo imaging techniques can then be performed to follow the destiny of transplanted Luc+ cells over time. These techniques have been used successfully to track the evolution of muscle cell transplantations. Accordingly, a commercial lentiviral vector carrying a luciferase reporter gene under the control of a CMV promoter (SABiosciences, FIG. 4) was used to develop stable Luc+ FSHD and control myoblast cell lines.

To develop cell lines that could be tracked in vivo following engraftment, FSHD and their matching control cells were seeded on day 0 and lentivirus infection was performed on day 2 according to Manufacturer's directions. Cells were transduced using a 4-hour infection with a Multiplicity of Infection (MOI) of 50. Cells were further amplified and maintained in culture under proliferative conditions where they showed normal signs of proliferation and differentiation. In vitro luciferase assays demonstrated luciferase activity, confirming development of cell models that can be used to track the destiny of the engrafted cells in vivo using bioluminescence imaging techniques.

In short, these results demonstrate the successful engraftment of FSHD cells into murine muscle with high efficiency as well as the development of a method to track the implanted cells in vivo. Live whole animal imaging experiments will be carried out to investigate how engrafted FSHD cells survive and regenerate compared to controls, and to identify biomarkers specific to FSHD.

Luciferase-expressing FSHD cells are engrafted into injured TA muscles, and their growth and differentiation assayed over time in vivo using Bioluminescence Imaging (BLI). Cell number is assessed as the bioluminescence signal derived from constitutive luciferase activity, and the linearity, sensitivity, and reproducibility of the bioluminescence assay for quantifying cell numbers will be first validated both in vitro and in vivo.

For BLI studies, cell-transplanted animals are anesthetized prior to receiving an intraperitoneal injection of luciferin (15 mg/ml at a dose of 130 mg/kg body weight recommended) and assayed in an imaging chamber with a Xenogen device. Images are acquired continuously for 30 minutes, and the same mice are imaged repeatedly over time once a month for up to 6 months. It has been shown that the dynamics of muscle cell behavior during muscle repair can be followed using this imaging technique. In vivo BLI of same mice imaged repeatedly over time has established the ability of transplanted satellite cells to respond to serial injury with successive waves of progenitor expansion and regeneration of muscle fibers. The magnitude of the regeneration response to sequential cardiotoxin injection, as monitored by imaging luciferase activity, reflects the persistence and renewal of stem cells over time. The relative regenerative responses of FSHD versus control muscles over time will test whether satellite cell regenerative capacity is impaired as an FSHD disease mechanism.

Live in vivo imaging technologies provide a unique technology to evaluate the role of satellite cell regenerative potential and muscle fiber survival in FSHD disease progression. In addition to engraftment studies of affected FSHD subjects, gene expression and regeneration and survival are evaluated in xenografts of myogenic cells from non-manifesting FSHD subjects (i.e. individuals with shortened D4Z4 arrays but no detectable signs of muscle weakness). While cell culture studies have suggested that these non-manifesting cells behave similarly to cells from subjects with clinically diagnosed FSHD (e.g. expression of DUX4-fl), it is possible that their in vivo characteristics will show reduced pathology, providing opportunities to investigate modifiers of disease progression.

Example 7

RNaseH1-Active Antisense Oligonucleotides (ASOs)

As indicated in Tables 2 and 4, certain markers are increased in subjects with FSHD relative to the levels of those markers in first degree unaffected subjects. Therapeutic effects are achieved by reducing the levels or biological activity of markers whose expression is upregulated in FSHD. In particular the invention provides targeted for degradation using RNaseH1-activating antisense oligonucleotides (ASO's) ("MOE gapmers"). The RNaseH1 ASO chemistry provides for a 20 nucleotide phosphorothioate backbone (5-10-5 gapmer). In particular, the oligonucleotide comprises five nucleotides at each end with the 2'-O-(2-methoxyethyl) (MOE) modification and ten central deoxyribonucleotides for activation of RNase H1.

For screening purposes, cell cultures of the invention are contacted with ASOs and the cells assayed for an amelioration of FSHD phenotype. In particular, the cells are assayed for an increase in the biological function of the cell or for an increase in the levels of one or more markers down-regulated in FSHD. In another embodiment, ASOs are administered to a chimeric mouse comprising a human FSHD cell. The chimeric mouse is then assayed for an increase in the biological activity of a human FSHD cell or an increase in the level of expression of a marker down-regulated in FSHD. In one embodiment, 25 mg/kg of the ASOs are administered by sub-cutaneous injection at least about 2× per week for 4 weeks or more.

In particular embodiments, the effects of ASOs on cells or chimeric mice of the invention are assayed using live cell imaging, muscle fiber turnover, or biomarker expression. In one embodiment, nude mice are treated to eliminate or reduce the number of muscle stem cells and/or differentiated muscle cell fibers and muscle stem cell replacement of muscle fiber turnover is assayed.

Example 8

Validation with qPCR

Of the 142 genes identified as candidate biomarkers in the microarray study described above, 18 genes (9 of which were up-regulated in FSHD vs. control myotubes and 9 which were down-regulated in FSHD vs. control myotubes) have now been evaluated on a larger collection of samples using quantitative real-time PCR (qPCR). The samples are derived from four of the five families from the microarray study and four additional families. Clinical information for the samples is given in Table 3. The qPCR experiments were performed using the BioMark 96.96 Dynamic Array (Fluidigm) platform with TaqMan Gene Expression Assays (Applied Biosystems).

TABLE 3

Samples used in qPCR study.

| Subject | Familial relations | Gender | Age | EcoRI/ BlnI (kb) | Deltoid strength (R, L) | Biceps strength (R, L) |
|---|---|---|---|---|---|---|
| 01A | proband | M | 42 | >40, 18 | 4+, 5 | 4+, 3− |
| 01U | brother of 01A | M | 46 | >40, >40 | 5, 5 | 5, 5 |
| 03A | proband | F | 40 | >40, 20 | 5, 5 | 4+, 4+ |
| 03U | sister of 03A | F | 42 | 157, 80 | 5, 5 | 5, 5 |
| 05A | proband | F | 55 | 67, 25 | 5, 5 | 5, 5 |
| 05C | brother of 05A | M | 49 | 67, 25 | 5, 5 | 5, 5 |
| 05V | son of 05A | M | 18 | 67 | 5, 5 | 5, 5 |
| 09A | proband | F | 31 | >112, 25 | 5, 5 | 4+, 4+ |
| 09U | mother of 09A | F | 57 | >112, 47 | 5, 5 | 5, 5 |
| 12A | daughter of 12B | F | 22 | 63, 18 | 4+, 4+ | 4+, 4+ |
| 12U | daughter of 12B | F | 24 | >112, >112 | 5, 5 | 5, 5 |
| 15A | proband | M | 66 | >112, 28 | 5, 5 | 4+, 4+ |
| 15V | sister of 15A | F | 60 | >145, 107 | 5, 5 | 5, 5 |
| 16A | proband | F | 56 | 97, 20 | 5−, 5− | 4−, 4+ |
| 16U | sister of 16A | F | 60 | 97, 93, 56 | 5, 5 | 5, 5 |
| 21B | daughter of 21A | F | 59 | 26, 40 | 5, 5 | 4+, 4+ |

TABLE 3-continued

Samples used in qPCR study.

| Subject | Familial relations | Gender | Age | EcoRI/ BlnI (kb) | Deltoid strength (R, L) | Biceps strength (R, L) |
|---|---|---|---|---|---|---|
| 21U | daughter of 21A | F | 48 | 142, 63 | 5, 5 | 5, 5 |

The 18 genes assessed with qPCR are listed in Table 4 below, along with their log(base 2) fold-change (LFC) between FSHD and control myotubes and the associated statistical significance (P-value) of this difference using qPCR. Table 2 also includes columns for the LFC and P-value from the original microarray study for comparison.

TABLE 4

Genes tested with qPCR.

| Gene | LFC (qPCR) | P-value (qPCR) | LFC (microarray) | P-value (microarray) |
|---|---|---|---|---|
| PRAMEF1 | 15.36* | 0.008* | 1.33 | 3.90E-04 |
| TRIM43 | 12.77* | 0.008* | 2.59 | 7.30E-05 |
| SLC34A2 | 11.30* | 0.008* | 2.23 | 4.00E-04 |
| TRIM49 | 11.72* | 0.008* | 1.68 | 5.80E-04 |
| TC2N | 2.96 | 0.002 | 0.72 | 5.20E-05 |
| DAG1 | −0.73 | 0.002 | −0.59 | 1.20E-05 |
| PAX7 | −1.79 | 0.027 | −0.75 | 8.40E-05 |
| CLYBL | −0.5 | 0.03 | −0.57 | 4.30E-04 |
| MYF5 | −1.72 | 0.068 | −0.91 | 9.40E-04 |
| ZNF445 | −0.35 | 0.069 | −0.31 | 4.10E-04 |
| ATP2A1 | −1.94 | 0.076 | −1.82 | 8.70E-05 |
| CD34 | 3.29 | 0.082 | 0.79 | 2.30E-04 |
| MRAP2 | −0.88 | 0.129 | −1.93 | 1.30E-04 |
| NAAA | 0.36 | 0.154 | 0.52 | 1.60E-04 |
| CALCRL | −0.36 | 0.342 | −1.17 | 8.40E-05 |
| HSPA6 | 0.83 | 0.38 | 0.49 | 2.90E-04 |
| SPATA17 | −0.04 | 0.763 | −0.49 | 6.10E-04 |
| CD177 | 0.09 | 0.88 | 0.83 | 8.00E-04 |

Log (base 2) fold-change (LFC) for FSHD vs. control myotubes and the associated p-values are shown for qPCR and also for the original microarray study. Negative values indicate that the gene is downregulated in FSHD.
Asterisks (*) in qPCR columns indicate that the transcript was not detected in at least one sample. In these cases the LFC may be inaccurate and a non-parametric sign test rather than a t-test was used for computing the p-value.

Cycle threshold (Ct) values for each gene in each sample were computed as the median Ct value of three technical qPCR replicates, and were then normalized by additive scaling of all Cts for each sample so that the average Ct of three reference genes M6PR, HPRT1, and PPIA was identical across samples (and equal to the un-normalized mean of these three genes across all samples). Transcripts of four genes (PRAMEF1, TRIM43, SLC34A2, TRIM49, highlighted in Table 4) were not detected with qPCR in one or more of the samples. In these cases the normalized Ct value was set to 40, which represents $2^{0.67}=1.6$-fold lower transcript abundance than the highest observed Ct of 39.33. The LFC estimates may be inaccurate for these genes, and these estimates are flagged with asterisks in the LFC column. Also, because this treatment of non-detected transcripts may violate the assumption of normality in t-tests, non-parametric sign tests were used on the paired (by family) differences between FSHD and control myotubes for these cases, indicated by asterisks in the p-value column. Multiple FSHD samples in a single family were replaced by their median value. In this test non-detected transcripts are considered to have lower expression than detected transcripts, but results do not otherwise depend on the precise Ct value assigned the non-detected transcripts. For genes that were detected in all the samples, p-values are bases on t-tests of the contrast FSHD vs. control from linear models with additive fixed effects for FSHD status and for family. This generalized a usual paired t-test by accommodating families with more than one FSHD subject.

All 9 genes that were up-regulated in FSHD in the microarray study were also upregulated in the qPCR study (positive LFC in both cases), and all 9 genes that were downregulated in FSHD in the microarray study were also down-regulated in the qPCR study (positive LFC in both cases). This overall concordance is directionally of change is significantly better than random (p=3.8e-6 by binomial test), and 6 of the genes individually showed significant differences between FSHD and control myotubes in the qPCR study at the p<0.01 level. Note that in the microarray analysis, to moderate the effect of outliers when ranking the more-than 20,000 genes, a statistical model with a pooled estimate of variance across the myoblasts and myotubes derived from biceps and deltoid biopsies was used, which further shrunk estimates of variance across different genes towards a common mean (by use of empirical Bayes moderated t-statistics). In the present qPCR analysis self-contained statistical tests were performed on myotubes derived from biceps, with no reference to myotube or deltoid samples, and sharing of information across genes. These factors may explain why more of the genes did not attain p<0.01 in the qPCR study.

Note that for each of the six genes with p<0.01 in the qPCR study (PRAMEF1, TRIM43, SLC34A2, TRIM49, TC2N, and DAG1) the FSHD vs. control paired differences showed the same direction for all of the cohorts: For the first five of these genes, each FSHD sample had a lower Ct value (higher expression) than its paired control sample, and for DAG1 each FSHD sample had a higher Ct value (lower expression) than its paired control sample. A stronger result held for PRAME1, TRIM43 and SLC34A2: for these three genes each FSHD sample had a lower Ct value (higher expression) than all of the control samples, not just the sample from the paired first-degree relative. This property is appealing for a biomarker since scores can then be assigned to individuals without the requirement of first-degree relatives as controls. However, the margin between the highest Ct values of FSHD samples and lowest Ct value of control samples was fairly small for these genes (0.56 Ct for TRIM43, 1.06 Cts for SLC34A2, 1.68 Cts for PRAMEF1).

It was then tested whether the difference of Ct values between two genes would provide discrimination between the FSHD and control samples with a larger margin, and thus more likely to generalize to other samples. The use of a simple difference rather than a more complex combination involving more genes makes the test simpler, and also removes the reliance on the choice of "housekeeping" gene(s), as these terms would cancel out so the difference is self-normalizing. The precise cutoffs for biomarkers would still depend on qPCR primers and efficiency of qPCR reactions, however, so should be recalibrated if these change.

Because the genes in the qPCR were selected on the basis of differential expression in the microarray study, assessing discriminants using the samples present in the microarrays will be biased. Moreover, searching over all pairs of genes introduces multiple hypotheses and the potential for overfitting. To address these issues, the pair of genes to use, and the cutoff on their difference to use as a discriminant, were selected based only on the qPCR data for the eight samples present in the microarray, so that the qPCR data for the nine samples not present in the microarray study could serve as an independent validation set. By examining all pairs of the 18 genes with qPCR data, the difference (Ct for PRAMEF1)−(Ct for PAX7) provided the maximum margin between FSHD and control samples, of 4.49 Cts. (Non-detected transcripts were assigned Ct of 40 during this maximization, and in application of the discriminant rule.)

The midpoint of the gap between FSHD and control samples for this difference was 7.05, yielding the discriminant rule of: classify as FSHD if (Ct for PRAMEF1)−(Ct for PAX7)<7.05, and classify as control otherwise. This rule correctly classified all nine samples (five FSHD and four control) that were not represented in the microarray experiment (and hence played no role in selecting the genes PRAMEF1 or PAX7, or the cutoff of 7.05). This is significantly better than random guessing (p=0.002 by binomial test). The margin between FSHD and control samples was slightly reduced when these additional nine samples were included, but was still 3.32 Ct, roughly twice the best margin (1.68) for Cts of any single gene when normalized by the reference genes M6PR, HPRT1, and PPIA.

Note the there are other pairwise differences that give larger margins that 1.68, and in the above we have focused just on the single maximal example chosen using a subset of the samples to avoid multiple-hypothesis testing on the validation samples. Other pairs with large margin are typically differences between one gene up-regulated in FSHD vs. controls and one gene down regulated in FSHD vs. control.

Example 9

Using FSHD Biomarkers to Identify and Evaluate the Efficacy of Antisense Oligonucleotide-Morpholino Drugs Using FSHD Myogenic Cells and Xenograft Muscles Antisense oligonucleotides conjugated to morpholinos are developed as inhibitors of the expression of FSHD disease genes, using cultured FSHD myogenic cells (prepared as described above in Example 1 and in Homma et al.) and FSHD xenograft muscle derived by engraftment and differentiation of FSHD myogenic cells into regenerating mouse muscles as described above. Antisense oligonucleotide mopholinos are designed that have nucleotide sequences designed to disrupt translation initiation, polyadenylation, and/or RNA splicing to knockdown expression of targeted FSHD disease mRNAs and block production of their encoded disease proteins. Specific antisense oligonucleotide drugs will first be tested by introduction into FSHD myogenic cells by electroporation or transfection with EndoPorter (Gene Tools). Drug-treated FSHD and control cells are monitored for evidence of cytotoxicity and changes in cell morphology, myofiber differentiation, and the expression of muscle protein biomarkers (desmin, MyoD, myogenin, MyHC). The efficacy of selected antisense oligonucleotides to block expression of targeted FSHD disease gene RNAs and proteins is evaluated by qPCR and immunoblotting assays. The efficacy of the antisense oligonucleotides as candidate FSHD drugs is evaluated by quantitative assays of the expression of FSHD disease biomarkers using qPCR, as established above. Promising candidate antisense FSHD drugs are identified by their activities to restore expression of FSHD biomarkers to levels produced by control cells derived from unaffected individuals.

Promising candidates are then tested in FSHD xenograft muscles by localized muscle injection and electroporation or systemic injection of antisense oligonucleotides, followed by qPCR assays of the expression of FSHD biomarkers and evaluation of hepatotoxic and immunostimulatory side effects over the time course of treatment. Antisense drugs with promising therapeutic value are identified by their activities to restore expression of FSHD biomarkers in both FSHD cells and xenograft muscles to levels observed in control myogenic cells and xenograft muscles derived from unaffected individuals.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A chimeric mouse comprising human cells derived from an FSHD affected subject or a first degree relative thereof, wherein the human cells replace 25-50% or more of the cells present in a skeletal muscle of the mouse.

2. The mouse of claim 1, wherein the human cells replace cells present in the tibialis anterior.

3. A set of chimeric mice comprising one mouse comprising human cells derived from an FSHD affected subject, wherein the human cells replace 25-50% or more of the cells present in a skeletal muscle of the mouse, and at least one mouse comprising human cells derived from a first degree relative of the FSHD affected subject, wherein the human cells replace 25-50% or more of the cells present in a skeletal muscle of the mouse.

4. A method of identifying an agent that ameliorates FSHD in a subject in need thereof, the method comprising administering the agent to the chimeric mouse of claim 1, and comparing the level of expression of a nucleic acid molecule of Table 2 or 4 in a human cell of the mouse relative to the level in an untreated control cell, wherein an agent that normalizes expression in said cell is identified as ameliorating FSHD.

5. The mouse of claim 1, wherein the human cells are enriched for myogenic cells.

6. The mouse of claim 1, wherein the human cells are isolated by selecting for cells positive for human CD 56.

7. The mouse of claim 1, wherein the human cells are skeletal muscle cells, muscle stem cells, or differentiated muscle fiber.

8. The mouse of claim 1, wherein the human cells are obtained from skeletal muscle biopsies.

9. The mouse of claim 8, wherein the biopsy is of a bicep or deltoid muscle.

10. The method of claim 4, wherein the nucleic acid molecule is selected from the group consisting of PRAMEF1, TRIM43, SLC34A2, TRIM49, TC2N, CD34, NAAA, HSPA6, and CD177.

11. A chimeric mouse created by a method comprising injecting a skeletal muscle of a mouse with at least or about $1 \times 10^6$ human FSHD myoblasts derived from an FSHD affected subject or a first degree relative thereof.

12. The chimeric mouse of claim 11, wherein the myoblasts are derived from skeletal muscle.

13. The chimeric mouse of claim 11, wherein the myoblasts are derived from a bicep or deltoid muscle.

14. A chimeric mouse comprising an engraftment in a skeletal muscle of at least or about 100,000 human nuclei derived from an FSHD affected subject or a first degree relative thereof.

15. The chimeric mouse of claim 14, wherein the nuclei are derived from skeletal muscle.

16. The chimeric mouse of claim 14, wherein the nuclei are derived from a bicep or deltoid muscle.

* * * * *